US012746077B2

(12) United States Patent
Jourdan et al.

(10) Patent No.: US 12,746,077 B2
(45) Date of Patent: Sep. 29, 2026

(54) SYSTEM WITH REMOVABLE HUBS FOR MANUAL AND ROBOTIC PROCEDURE

(71) Applicant: Imperative Care, Inc., Campbell, CA (US)

(72) Inventors: Theodore Jourdan, Mt. Pleasant, SC (US); Lilip Lau, Los Altos, CA (US); Robert Hitchcock, Los Gatos, CA (US); Craig Mar, Fremont, CA (US)

(73) Assignee: Imperative Care, Inc., Campbell, CA (US)

( * ) Notice: Subject to any disclaimer, the term of this patent is extended or adjusted under 35 U.S.C. 154(b) by 226 days.

(21) Appl. No.: 18/545,687

(22) Filed: Dec. 19, 2023

(65) Prior Publication Data

US 2024/0197418 A1 Jun. 20, 2024

Related U.S. Application Data

(60) Provisional application No. 63/434,040, filed on Dec. 20, 2022.

(51) Int. Cl.
*A61B 34/30* (2016.01)
*A61B 17/00* (2006.01)
(Continued)

(52) U.S. Cl.
CPC .............. *A61B 34/30* (2016.02); *A61B 17/00* (2013.01); *A61B 17/22* (2013.01); *A61B 34/71* (2016.02);
(Continued)

(58) Field of Classification Search
CPC ......... A61B 34/30; A61B 17/00; A61B 17/22; A61B 34/71; A61B 2017/00022;
(Continued)

(56) References Cited

U.S. PATENT DOCUMENTS 1,286,033 A 11/1918 Lambeth
4,819,653 A 4/1989 Marks
(Continued)

FOREIGN PATENT DOCUMENTS

AU 2006268156 4/2012
CN 102462533 5/2012
(Continued)

OTHER PUBLICATIONS

US 12,076,032 B1, 09/2024, Teigen et al. (withdrawn)
(Continued)

*Primary Examiner* — Sohana Tanju Khayer
(74) *Attorney, Agent, or Firm* — Knobbe, Martens, Olson & Bear, LLP

(57) ABSTRACT

A system for performing a vascular procedure includes a robotic drive system and one or more hub assemblies operatively coupled to the robotic drive system, each of the one or more hub assemblies including a mount, a hub removably coupled to the mount, and an interventional device coupled to the hub. For each of the one or more hub assemblies, the mount is configured to be driven by the robotic drive system to drive the interventional device within a vasculature of a patient, the hub is configured to be uncoupled from the mount while the interventional device is positioned within the vasculature of the patient, and the hub is configured to be manually manipulated to navigate the interventional device to a vascular site while the hub is uncoupled from the mount.

20 Claims, 35 Drawing Sheets

(51) Int. Cl.

| | |
|---|---|
| ***A61B 17/22*** | (2006.01) |
| ***A61B 34/00*** | (2016.01) |
| ***A61B 34/20*** | (2016.01) |
| ***A61M 25/00*** | (2006.01) |
| ***A61M 25/01*** | (2006.01) |
| ***A61M 25/09*** | (2006.01) |
| *A61B 90/00* | (2016.01) |

(52) U.S. Cl.

CPC .... *A61M 25/0097* (2013.01); *A61M 25/0116* (2013.01); *A61M 25/0127* (2013.01); *A61M 25/09041* (2013.01); *A61B 2017/00022* (2013.01); *A61B 2017/00115* (2013.01); *A61B 2017/00477* (2013.01); *A61B 2017/00876* (2013.01); *A61B 2017/22038* (2013.01); *A61B 2017/22079* (2013.01); *A61B 2034/2059* (2016.02); *A61B 2034/2061* (2016.02); *A61B 2034/301* (2016.02); *A61B 2090/064* (2016.02); *A61B 2090/066* (2016.02); *A61B 2090/3966* (2016.02)

(58) Field of Classification Search

CPC ........... A61B 2017/00115; A61B 2017/00477; A61B 2017/00876; A61B 2017/22038; A61B 2017/22079; A61B 2034/2059; A61B 2034/2061; A61B 2034/301; A61B 2090/064; A61B 2090/066; A61B 2090/3966; A61M 25/0097; A61M 25/0116; A61M 25/0127; A61M 25/09041

See application file for complete search history.

(56) References Cited

U.S. PATENT DOCUMENTS

| | | | |
|---|---|---|---|
| 4,925,444 | A | 5/1990 | Orkin |
| 5,037,404 | A | 8/1991 | Gold et al. |
| 5,120,317 | A | 6/1992 | Luther |
| 5,131,391 | A | 7/1992 | Sakai et al. |
| 5,380,268 | A | 1/1995 | Wheeler |
| 5,638,818 | A | 6/1997 | Diab et al. |
| 5,766,184 | A | 6/1998 | Matsuno |
| 5,817,031 | A | 10/1998 | Masuo |
| 5,882,333 | A | 3/1999 | Schaer et al. |
| 5,989,208 | A | 11/1999 | Nita |
| 6,096,004 | A | 8/2000 | Meglan et al. |
| 6,375,471 | B1 | 4/2002 | Wendlandt et al. |
| 6,400,971 | B1 | 6/2002 | Firanov et al. |
| 6,547,766 | B1 | 4/2003 | Fitz |
| 6,726,675 | B1 | 4/2004 | Beyar |
| 6,821,287 | B1 | 11/2004 | Jang |
| 7,172,572 | B2 | 2/2007 | Diamond |
| 7,192,433 | B2 | 3/2007 | Osypka et al. |
| 7,214,230 | B2 | 5/2007 | Brock et al. |
| 7,251,552 | B2 | 7/2007 | Schmeisser |
| 7,331,967 | B2 | 2/2008 | Lee et al. |
| 7,379,790 | B2 | 5/2008 | Toth et al. |
| D572,615 | S | 7/2008 | Gerold |
| 7,556,611 | B2 | 7/2009 | Kolenbrander et al. |
| 7,567,233 | B2 | 7/2009 | Garibaldi et al. |
| 7,608,083 | B2 | 10/2009 | Lee et al. |
| 7,615,042 | B2 | 11/2009 | Beyar et al. |
| 7,727,185 | B2 | 6/2010 | Weitzner |
| 7,747,960 | B2 | 6/2010 | Garibaldi et al. |
| 7,756,308 | B2 | 7/2010 | Viswanathan |
| 7,761,133 | B2 | 7/2010 | Viswanathan et al. |
| 7,766,894 | B2 | 8/2010 | Weitzner et al. |
| 7,789,874 | B2 | 9/2010 | Yu et al. |
| D626,250 | S | 10/2010 | Wenderow et al. |
| 7,818,076 | B2 | 10/2010 | Viswanathan |
| 7,831,294 | B2 | 11/2010 | Viswanathan |
| 7,850,640 | B2 | 12/2010 | Williams et al. |
| 7,850,642 | B2 | 12/2010 | Moll et al. |
| 7,853,306 | B2 | 12/2010 | Viswanathan et al. |
| 7,884,727 | B2 | 2/2011 | Tran |
| 7,886,743 | B2 | 2/2011 | Cooper et al. |
| 7,887,549 | B2 | 2/2011 | Wenderow et al. |
| 7,909,798 | B2 | 3/2011 | Osypka |
| 7,951,243 | B2 | 5/2011 | Boyle, Jr. et al. |
| 7,955,316 | B2 | 6/2011 | Weitzner et al. |
| 7,963,288 | B2 | 6/2011 | Rosenberg et al. |
| D641,797 | S | 7/2011 | Chen |
| 8,004,229 | B2 | 8/2011 | Nowlin et al. |
| 8,021,326 | B2 | 9/2011 | Moll et al. |
| RE42,804 | E | 10/2011 | Dedig et al. |
| 8,052,636 | B2 | 11/2011 | Moll et al. |
| 8,083,753 | B2 | 12/2011 | Solar et al. |
| 8,108,069 | B2 | 1/2012 | Stahler et al. |
| 8,114,032 | B2 | 2/2012 | Ferry et al. |
| 8,123,726 | B2 | 2/2012 | Searfoss et al. |
| 8,131,379 | B2 | 3/2012 | Hauck |
| 8,137,317 | B2 | 3/2012 | Osypka |
| 8,146,874 | B2 | 4/2012 | Yu |
| 8,165,684 | B2 | 4/2012 | Putz et al. |
| 8,190,238 | B2 | 5/2012 | Moll et al. |
| 8,220,468 | B2 | 7/2012 | Cooper et al. |
| 8,242,972 | B2 | 8/2012 | Garibaldi et al. |
| 8,244,824 | B2 | 8/2012 | Garibaldi et al. |
| 8,257,302 | B2 | 9/2012 | Beyar et al. |
| 8,262,671 | B2 | 9/2012 | Osypka |
| 8,281,807 | B2 | 10/2012 | Trombley et al. |
| 8,307,693 | B2 | 11/2012 | Uram et al. |
| D674,484 | S | 1/2013 | Murphy et al. |
| 8,343,096 | B2 | 1/2013 | Kirschenman et al. |
| 8,343,098 | B2 | 1/2013 | Nystrom et al. |
| 8,377,077 | B2 | 2/2013 | Reis |
| 8,390,438 | B2 | 3/2013 | Olson et al. |
| 8,399,871 | B2 | 3/2013 | Beyar et al. |
| 8,403,909 | B2 | 3/2013 | Spohn et al. |
| D680,645 | S | 4/2013 | Murphy et al. |
| 8,409,172 | B2 | 4/2013 | Moll et al. |
| 8,467,853 | B2 | 6/2013 | Hunter et al. |
| D685,468 | S | 7/2013 | Murphy et al. |
| 8,480,618 | B2 | 7/2013 | Wenderow et al. |
| 8,498,691 | B2 | 7/2013 | Moll et al. |
| 8,506,555 | B2 | 8/2013 | Morales |
| 8,521,331 | B2 | 8/2013 | Itkowitz |
| 8,529,582 | B2 | 9/2013 | Devengenzo et al. |
| 8,540,698 | B2 | 9/2013 | Spohn et al. |
| 8,551,084 | B2 | 10/2013 | Hauck et al. |
| 8,603,068 | B2 | 12/2013 | Weitzner et al. |
| 8,613,730 | B2 | 12/2013 | Hieb et al. |
| 8,617,102 | B2 | 12/2013 | Moll et al. |
| 8,620,473 | B2 | 12/2013 | Diolaiti et al. |
| 8,671,817 | B1 | 3/2014 | Bogusky |
| 8,672,880 | B2 | 3/2014 | Cohen et al. |
| 8,679,150 | B1 | 3/2014 | Janardhan |
| 8,684,953 | B2 | 4/2014 | Cabiri |
| 8,684,962 | B2 | 4/2014 | Kirschenman et al. |
| 8,694,157 | B2 | 4/2014 | Wenderow et al. |
| 8,740,840 | B2 | 6/2014 | Foley et al. |
| 8,747,358 | B2 | 6/2014 | Trombley et al. |
| 8,790,297 | B2 | 7/2014 | Bromander et al. |
| 8,799,792 | B2 | 8/2014 | Garibaldi et al. |
| 8,800,881 | B2 | 8/2014 | Biset et al. |
| 8,801,661 | B2 | 8/2014 | Moll et al. |
| 8,806,359 | B2 | 8/2014 | Garibaldi et al. |
| 8,827,948 | B2 | 9/2014 | Romo |
| 8,828,021 | B2 | 9/2014 | Wenderow et al. |
| 8,833,293 | B2 | 9/2014 | Horn |
| 8,840,628 | B2 | 9/2014 | Green et al. |
| 8,852,162 | B2 | 10/2014 | Williams et al. |
| 8,852,167 | B2 | 10/2014 | Trombley et al. |
| 8,852,184 | B2 | 10/2014 | Kucklick |
| 8,876,726 | B2 | 11/2014 | Amit et al. |
| 8,894,610 | B2 | 11/2014 | Macnamara et al. |
| 8,905,969 | B2 | 12/2014 | Nystrom et al. |
| 8,939,963 | B2 | 1/2015 | Rogers et al. |
| 8,961,491 | B2 | 2/2015 | Uber et al. |
| 8,968,333 | B2 | 3/2015 | Yu et al. |
| 8,974,408 | B2 | 3/2015 | Wallace et al. |
| 8,974,420 | B2 | 3/2015 | Searfoss et al. |

(56) References Cited

U.S. PATENT DOCUMENTS

| | | | |
|---|---|---|---|
| 8,979,871 | B2 | 3/2015 | Tye |
| 8,986,246 | B2 | 3/2015 | Foley et al. |
| 9,005,271 | B2 | 4/2015 | Ivancev |
| 9,056,200 | B2 | 6/2015 | Uber et al. |
| 9,066,740 | B2 | 6/2015 | Carlson et al. |
| 9,070,486 | B2 | 6/2015 | Guerrera et al. |
| 9,095,681 | B2 | 8/2015 | Wenderow et al. |
| 9,101,379 | B2 | 8/2015 | Au et al. |
| 9,111,016 | B2 | 8/2015 | Besson et al. |
| 9,132,949 | B2 | 9/2015 | Bidet et al. |
| 9,138,566 | B2 | 9/2015 | Cabiri |
| 9,168,356 | B2 | 10/2015 | Wenderow et al. |
| 9,186,046 | B2 | 11/2015 | Ramamurthy et al. |
| 9,199,033 | B1 | 12/2015 | Cowan et al. |
| 9,205,227 | B2 | 12/2015 | Cohen et al. |
| 9,206,309 | B2 | 12/2015 | Appleby |
| 9,220,568 | B2 | 12/2015 | Bromander et al. |
| 9,233,225 | B2 | 1/2016 | Hebert |
| 9,241,768 | B2 | 1/2016 | Sandhu et al. |
| 9,242,252 | B2 | 1/2016 | Eberle et al. |
| 9,259,526 | B2 | 2/2016 | Barron et al. |
| 9,295,527 | B2 | 3/2016 | Kirschenman et al. |
| 9,314,306 | B2 | 4/2016 | Yu |
| 9,314,307 | B2 | 4/2016 | Richmond et al. |
| 9,314,310 | B2 | 4/2016 | Kirschenman et al. |
| 9,314,311 | B2 | 4/2016 | Wenderow et al. |
| 9,314,594 | B2 | 4/2016 | Kirschenman |
| 9,315,663 | B2 | 4/2016 | Appleby |
| 9,320,479 | B2 | 4/2016 | Wenderow et al. |
| 9,320,573 | B2 | 4/2016 | Sandhu et al. |
| 9,333,324 | B2 | 5/2016 | Cohen et al. |
| 9,345,859 | B2 | 5/2016 | Blacker |
| 9,351,735 | B2 | 5/2016 | Nagano et al. |
| 9,375,729 | B2 | 6/2016 | Eberle et al. |
| 9,402,977 | B2 | 8/2016 | Wenderow et al. |
| 9,408,669 | B2 | 8/2016 | Kokish et al. |
| 9,427,515 | B1 | 8/2016 | Nystrom |
| 9,427,562 | B2 | 8/2016 | Blacker |
| D766,902 | S | 9/2016 | Bellinghausen |
| 9,439,736 | B2 | 9/2016 | Olson |
| 9,447,890 | B2 | 9/2016 | Jennings et al. |
| 9,452,276 | B2 | 9/2016 | Duindam et al. |
| 9,452,277 | B2 | 9/2016 | Blacker |
| 9,474,857 | B2 | 10/2016 | Riley et al. |
| 9,480,797 | B1 | 11/2016 | Swantner et al. |
| 9,488,971 | B2 | 11/2016 | Yip et al. |
| 9,498,291 | B2 | 11/2016 | Gilbert et al. |
| 9,510,912 | B2 | 12/2016 | Bencteux et al. |
| 9,517,305 | B2 | 12/2016 | Uram et al. |
| 9,532,840 | B2 | 1/2017 | Wong et al. |
| 9,533,121 | B2 | 1/2017 | Pacheco et al. |
| 9,545,497 | B2 | 1/2017 | Wenderow et al. |
| 9,549,783 | B2 | 1/2017 | Zirps |
| 9,566,201 | B2 | 2/2017 | Yu |
| 9,566,414 | B2 | 2/2017 | Wong et al. |
| 9,572,481 | B2 | 2/2017 | Duindam et al. |
| 9,585,806 | B2 | 3/2017 | Herrig |
| 9,586,029 | B2 | 3/2017 | Shekalim et al. |
| 9,603,573 | B2 | 3/2017 | Leininger et al. |
| 9,623,209 | B2 | 4/2017 | Wenderow et al. |
| 9,629,595 | B2 | 4/2017 | Walker et al. |
| 9,636,479 | B2 | 5/2017 | Bencteux et al. |
| 9,687,304 | B2 | 6/2017 | Bencteux et al. |
| 9,700,698 | B2 | 7/2017 | Pacheco et al. |
| 9,707,377 | B2 | 7/2017 | Cohen et al. |
| 9,717,552 | B2 | 8/2017 | Cosman |
| 9,744,305 | B2 | 8/2017 | Cowan et al. |
| 9,750,576 | B2 | 9/2017 | Murphy et al. |
| 9,750,953 | B2 | 9/2017 | Kalafut |
| 9,764,114 | B2 | 9/2017 | Murphy et al. |
| 9,770,301 | B2 | 9/2017 | Bencteux et al. |
| 9,782,130 | B2 | 10/2017 | Hauck et al. |
| 9,782,564 | B2 | 10/2017 | Zirps et al. |
| 9,789,285 | B1 | 10/2017 | Blacker |
| D803,837 | S | 11/2017 | Kumar |
| 9,814,534 | B2 | 11/2017 | Wenderow et al. |
| 9,825,455 | B2 | 11/2017 | Sandhu et al. |
| 9,827,410 | B2 | 11/2017 | Cowan et al. |
| 9,828,157 | B2 | 11/2017 | Roesler |
| 9,833,293 | B2 | 12/2017 | Wenderow et al. |
| 9,839,481 | B2 | 12/2017 | Blumenkranz et al. |
| 9,855,101 | B2 | 1/2018 | Wenderow et al. |
| 9,943,321 | B2 | 4/2018 | Nita |
| 9,943,958 | B2 | 4/2018 | Blacker et al. |
| 9,949,799 | B2 | 4/2018 | Hingwe et al. |
| 9,962,229 | B2 | 5/2018 | Blacker et al. |
| 9,981,109 | B2 | 5/2018 | Blacker et al. |
| 9,993,614 | B2 | 6/2018 | Pacheco et al. |
| 9,993,615 | B2 | 6/2018 | Blacker |
| 9,999,751 | B2 | 6/2018 | Pacheco et al. |
| 10,010,699 | B2 | 7/2018 | Cohen et al. |
| 10,029,072 | B2 | 7/2018 | Hebert |
| 10,046,140 | B2 | 8/2018 | Kokish et al. |
| 10,052,761 | B2 | 8/2018 | Langenfeld et al. |
| 10,071,224 | B2 | 9/2018 | Hebert |
| 10,071,225 | B2 | 9/2018 | Hebert |
| 10,085,805 | B1 | 10/2018 | Blacker |
| 10,086,167 | B2 | 10/2018 | Hebert |
| 10,105,486 | B2 | 10/2018 | Trombley et al. |
| 10,111,703 | B2 | 10/2018 | Cosman, Jr. |
| 10,123,843 | B2 | 11/2018 | Wong et al. |
| 10,123,844 | B2 | 11/2018 | Nowlin et al. |
| 10,124,149 | B2 | 11/2018 | Hebert |
| 10,130,427 | B2 | 11/2018 | Tanner et al. |
| 10,138,025 | B2 | 11/2018 | Nakamura |
| 10,145,747 | B1 | 12/2018 | Lin et al. |
| 10,149,698 | B2 | 12/2018 | Wulfman et al. |
| 10,178,995 | B2 | 1/2019 | Cragg |
| 10,183,147 | B2 | 1/2019 | Yang et al. |
| 10,201,314 | B2 | 2/2019 | Frederick et al. |
| 10,207,315 | B2 | 2/2019 | Appleby |
| 10,231,788 | B2 | 3/2019 | Olson et al. |
| 10,238,456 | B2 | 3/2019 | Murphy et al. |
| 10,245,112 | B2 | 4/2019 | Kottenstette et al. |
| 10,258,285 | B2 | 4/2019 | Hauck et al. |
| 10,271,910 | B2 | 4/2019 | Wenderow et al. |
| 10,299,867 | B2 | 5/2019 | Wenderow et al. |
| D850,447 | S | 6/2019 | Fulghum |
| 10,307,061 | B2 | 6/2019 | Cohen |
| 10,307,570 | B2 | 6/2019 | Blacker |
| 10,322,277 | B2 | 6/2019 | Nystrom |
| 10,342,606 | B2 | 7/2019 | Cosman |
| 10,342,953 | B2 | 7/2019 | Wenderow et al. |
| 10,363,062 | B2 | 7/2019 | Spencer et al. |
| 10,363,109 | B2 | 7/2019 | Dachs, II et al. |
| 10,368,951 | B2 | 8/2019 | Moll et al. |
| 10,391,234 | B2 | 8/2019 | Sams et al. |
| 10,420,537 | B2 | 9/2019 | Salahieh et al. |
| 10,426,557 | B2 | 10/2019 | Amiri et al. |
| 10,426,559 | B2 | 10/2019 | Graetzel et al. |
| 10,426,926 | B2 | 10/2019 | Blacker et al. |
| 10,449,007 | B2 | 10/2019 | Deboeuf et al. |
| 10,456,556 | B2 | 10/2019 | Cabiri |
| 10,512,514 | B2 | 12/2019 | Nowlin et al. |
| 10,522,250 | B2 | 12/2019 | Spohn et al. |
| 10,531,883 | B1 | 1/2020 | Deville et al. |
| 10,531,929 | B2 | 1/2020 | Widenhouse et al. |
| 10,537,400 | B2 | 1/2020 | Dachs, II et al. |
| 10,539,478 | B2 | 1/2020 | Lin et al. |
| 10,549,071 | B2 | 2/2020 | Falb et al. |
| 10,549,084 | B2 | 2/2020 | Sokolov et al. |
| 10,555,780 | B2 | 2/2020 | Tanner et al. |
| 10,556,092 | B2 | 2/2020 | Yu et al. |
| 10,561,821 | B2 | 2/2020 | Wenderow et al. |
| 10,568,539 | B2 | 2/2020 | Kowshik et al. |
| 10,568,700 | B2 | 2/2020 | Donhowe et al. |
| 10,583,276 | B2 | 3/2020 | Zirps |
| 10,588,656 | B2 | 3/2020 | Trosper et al. |
| 10,589,018 | B2 | 3/2020 | Uber et al. |
| D881,234 | S | 4/2020 | Capela |
| 10,611,391 | B1 | 4/2020 | Klem et al. |
| 10,639,098 | B2 | 5/2020 | Cosman |
| 10,647,007 | B2 | 5/2020 | Cordoba et al. |
| 10,653,863 | B1 | 5/2020 | Blacker et al. |

(56) References Cited

U.S. PATENT DOCUMENTS

| | | | |
|---|---|---|---|
| 10,660,814 | B2 | 5/2020 | Soundararajan et al. |
| 10,661,453 | B2 | 5/2020 | Koenig et al. |
| 10,687,903 | B2 | 6/2020 | Lewis et al. |
| 10,695,140 | B2 | 6/2020 | Overmyer et al. |
| 10,695,533 | B2 | 6/2020 | Deboeuf et al. |
| 10,695,536 | B2 | 6/2020 | Weitzner et al. |
| 10,709,510 | B2 | 7/2020 | Kottenstette |
| 10,709,512 | B2 | 7/2020 | Bajo et al. |
| 10,716,726 | B2 | 7/2020 | Bergman et al. |
| 10,722,253 | B2 | 7/2020 | Deville et al. |
| 10,729,825 | B2 | 8/2020 | Boyle, Jr. et al. |
| 10,736,706 | B2 | 8/2020 | Scheib |
| 10,737,061 | B2 | 8/2020 | Parmar |
| 10,744,302 | B2 | 8/2020 | Pacheco et al. |
| 10,765,303 | B2 | 9/2020 | Graetzel et al. |
| 10,765,486 | B2 | 9/2020 | Bajo et al. |
| 10,779,775 | B2 | 9/2020 | Bergman et al. |
| 10,779,895 | B2 | 9/2020 | Wenderow et al. |
| 10,783,993 | B2 | 9/2020 | Spohn et al. |
| 10,799,305 | B2 | 10/2020 | Murphy et al. |
| 10,806,905 | B2 | 10/2020 | Asmus |
| 10,813,713 | B2 | 10/2020 | Koch et al. |
| 10,814,102 | B2 | 10/2020 | Laby et al. |
| D901,018 | S | 11/2020 | Swen |
| 10,820,951 | B2 | 11/2020 | Soundararajan et al. |
| 10,820,954 | B2 | 11/2020 | Marsot et al. |
| 10,827,913 | B2 | 11/2020 | Ummalaneni et al. |
| 10,828,463 | B2 | 11/2020 | Blacker |
| 10,835,153 | B2 | 11/2020 | Rafii-Tari et al. |
| 10,835,329 | B2 | 11/2020 | Wenderow et al. |
| 10,835,668 | B2 | 11/2020 | Novickoff et al. |
| 10,849,702 | B2 | 12/2020 | Hsu et al. |
| 10,864,629 | B2 | 12/2020 | Guerrera et al. |
| 10,874,468 | B2 | 12/2020 | Wallace et al. |
| 10,881,472 | B2 | 1/2021 | Sen et al. |
| 10,881,474 | B2 | 1/2021 | Blacker et al. |
| 10,881,765 | B2 | 1/2021 | Igarashi |
| 10,898,082 | B2 | 1/2021 | Sandgaard |
| 10,898,288 | B2 | 1/2021 | Dachs, II et al. |
| 10,900,771 | B2 | 1/2021 | Kottenstette et al. |
| 10,912,624 | B2 | 2/2021 | Prentakis et al. |
| 10,912,924 | B2 | 2/2021 | Park et al. |
| 10,945,904 | B2 | 3/2021 | de Jesus Ruiz et al. |
| 10,953,206 | B2 | 3/2021 | Blacker |
| 10,959,789 | B2 | 3/2021 | Yi et al. |
| 10,959,792 | B1 | 3/2021 | Huang et al. |
| 10,987,179 | B2 | 4/2021 | Ummalaneni et al. |
| 10,987,491 | B2 | 4/2021 | Wenderow et al. |
| 10,994,102 | B2 | 5/2021 | Blacker |
| 11,007,118 | B2 | 5/2021 | Cowan et al. |
| 11,007,348 | B2 | 5/2021 | Blacker |
| 11,040,147 | B2 | 6/2021 | Wagner |
| 11,045,274 | B2 | 6/2021 | Dachs, II et al. |
| 11,052,226 | B2 | 7/2021 | Salahieh et al. |
| 11,058,508 | B2 | 7/2021 | Scheib et al. |
| 11,076,924 | B2 | 8/2021 | Kim et al. |
| 11,078,945 | B2 | 8/2021 | Grout et al. |
| 11,083,842 | B2 | 8/2021 | Chassot |
| 11,083,873 | B2 | 8/2021 | Hebert |
| 11,083,882 | B2 | 8/2021 | Schrauder et al. |
| 11,096,712 | B2 | 8/2021 | Teigen et al. |
| 11,104,012 | B2 | 8/2021 | Cordoba et al. |
| 11,109,919 | B2 | 9/2021 | Murphy et al. |
| 11,109,920 | B2 | 9/2021 | Al-Jadda et al. |
| 11,109,921 | B2 | 9/2021 | Kottenstette et al. |
| 11,110,217 | B2 | 9/2021 | O'Brien et al. |
| 11,114,918 | B2 | 9/2021 | Zirps |
| 11,129,602 | B2 | 9/2021 | Wong et al. |
| 11,141,566 | B2 | 10/2021 | Cabiri |
| 11,147,950 | B2 | 10/2021 | Destrebecq et al. |
| 11,179,213 | B2 | 11/2021 | Huang et al. |
| 11,179,546 | B2 | 11/2021 | Martin |
| 11,185,455 | B2 | 11/2021 | Cagle et al. |
| 11,191,893 | B2 | 12/2021 | Capone et al. |
| 11,197,683 | B1 | 12/2021 | Teigen et al. |
| 11,207,147 | B2 | 12/2021 | Diamond et al. |
| 11,209,300 | B2 | 12/2021 | Johnson |
| 11,213,356 | B2 | 1/2022 | Tanner et al. |
| 11,213,362 | B2 | 1/2022 | Sharon et al. |
| 11,213,654 | B2 | 1/2022 | Murphy et al. |
| 11,234,779 | B2 | 2/2022 | Fuerst et al. |
| 11,234,781 | B2 | 2/2022 | Penny et al. |
| 11,234,784 | B2 | 2/2022 | Alden |
| 11,241,291 | B2 | 2/2022 | Sharon et al. |
| 11,259,881 | B2 | 3/2022 | Garcia Kilroy et al. |
| 11,266,424 | B2 | 3/2022 | Hofmann et al. |
| 11,291,515 | B2 | 4/2022 | Sharon et al. |
| 11,298,198 | B2 | 4/2022 | Fournier et al. |
| 11,304,668 | B2 | 4/2022 | Wenderow et al. |
| 11,318,618 | B2 | 5/2022 | Desai |
| 11,331,157 | B2 | 5/2022 | Russell et al. |
| 11,337,712 | B2 | 5/2022 | Teigen et al. |
| 11,337,764 | B2 | 5/2022 | Deboeuf et al. |
| 11,357,586 | B2 | 6/2022 | Huang et al. |
| 11,357,597 | B2 | 6/2022 | Jhaveri et al. |
| 11,359,156 | B2 | 6/2022 | Long et al. |
| 11,376,086 | B2 | 7/2022 | McGrogan et al. |
| 11,389,360 | B2 | 7/2022 | Koenig et al. |
| 11,395,665 | B2 | 7/2022 | Yang et al. |
| 11,400,214 | B2 | 8/2022 | Porter |
| 11,406,402 | B2 | 8/2022 | Deville et al. |
| 11,413,101 | B2 | 8/2022 | Sen et al. |
| 11,413,431 | B2 | 8/2022 | Blacker |
| 11,419,977 | B2 | 8/2022 | Cowan et al. |
| 11,426,246 | B2 | 8/2022 | Asadian et al. |
| 11,432,835 | B2 | 9/2022 | Shaffer et al. |
| 11,432,840 | B2 | 9/2022 | Grothe et al. |
| 11,448,327 | B2 | 9/2022 | Heffner et al. |
| 11,464,587 | B2 | 10/2022 | Yu et al. |
| 11,464,589 | B1 | 10/2022 | Roh et al. |
| 11,472,030 | B2 | 10/2022 | Ho et al. |
| 11,478,329 | B2 | 10/2022 | Gee et al. |
| 11,490,911 | B2 | 11/2022 | Panian |
| 11,491,313 | B2 | 11/2022 | Fischel |
| 11,497,481 | B2 | 11/2022 | Penny et al. |
| 11,497,523 | B2 | 11/2022 | Trosper et al. |
| 11,497,568 | B2 | 11/2022 | Ho et al. |
| 11,510,736 | B2 | 11/2022 | Rafii-Tari et al. |
| D976,399 | S | 1/2023 | Carmi |
| 11,547,426 | B2 | 1/2023 | Deville et al. |
| 11,547,511 | B2 | 1/2023 | Asadian et al. |
| 11,564,649 | B2 | 1/2023 | Kedmi-Shahar et al. |
| 11,571,267 | B2 | 2/2023 | Gonenc et al. |
| 11,576,743 | B2 | 2/2023 | Venkataraman et al. |
| 11,577,382 | B2 | 2/2023 | Cagle et al. |
| 11,589,931 | B2 | 2/2023 | Desai et al. |
| 11,607,108 | B2 | 3/2023 | Yu et al. |
| 11,628,024 | B2 | 4/2023 | Kapadia |
| 11,633,247 | B2 | 4/2023 | Johnson et al. |
| 11,642,181 | B2 | 5/2023 | Nobles et al. |
| 11,653,905 | B2 | 5/2023 | Wong et al. |
| 11,660,151 | B2 | 5/2023 | Schena |
| 11,660,437 | B2 | 5/2023 | Verma |
| 11,672,602 | B2 | 6/2023 | Monteverde et al. |
| 11,678,943 | B2 | 6/2023 | Zhou et al. |
| 11,678,948 | B2 | 6/2023 | Vargas et al. |
| 11,684,759 | B2 | 6/2023 | Hayzelden |
| 11,690,985 | B2 | 7/2023 | Calhoun et al. |
| 11,696,808 | B2 | 7/2023 | Blacker et al. |
| 11,696,810 | B2 | 7/2023 | Asadian et al. |
| 11,701,196 | B2 | 7/2023 | Scheib et al. |
| 11,703,604 | B2 | 7/2023 | Dissertori et al. |
| 11,712,805 | B2 | 8/2023 | Zhou et al. |
| 11,713,376 | B2 | 8/2023 | Leroux et al. |
| 11,717,356 | B2 | 8/2023 | Amiri et al. |
| 11,717,640 | B2 | 8/2023 | Fantuzzi et al. |
| 11,723,739 | B2 | 8/2023 | Asadian et al. |
| 11,723,744 | B2 | 8/2023 | Ergueta Tejerina et al. |
| 11,730,499 | B1 | 8/2023 | Thio et al. |
| 11,737,821 | B2 | 8/2023 | Algawi et al. |
| 11,744,989 | B2 | 9/2023 | Blacker |
| 11,759,269 | B2 | 9/2023 | Zhou et al. |
| 11,764,873 | B2 | 9/2023 | Burla et al. |
| 11,765,360 | B2 | 9/2023 | Schroers et al. |

(56) References Cited

U.S. PATENT DOCUMENTS

| | | | |
|---|---|---|---|
| 11,766,786 | B2 | 9/2023 | Cordoba et al. |
| 11,780,092 | B2 | 10/2023 | Desai et al. |
| 11,785,938 | B2 | 10/2023 | Clavien et al. |
| 11,786,329 | B2 | 10/2023 | Fuerst et al. |
| 11,789,315 | B1 | 10/2023 | Yu et al. |
| 11,793,500 | B2 | 10/2023 | Vargas |
| 11,793,597 | B2 | 10/2023 | Vargas et al. |
| 11,801,365 | B2 | 10/2023 | Blacker et al. |
| 11,813,203 | B2 | 11/2023 | Timm et al. |
| 11,819,295 | B2 | 11/2023 | Wenderow et al. |
| 11,832,904 | B2 | 12/2023 | Wenderow et al. |
| 11,844,580 | B2 | 12/2023 | Sen et al. |
| 11,844,732 | B2 | 12/2023 | Klem et al. |
| 11,883,119 | B2 | 1/2024 | Sen et al. |
| 11,883,245 | B2 | 1/2024 | Fathollahi Ghezelghieh et al. |
| 11,890,024 | B2 | 2/2024 | Panian |
| 11,890,432 | B2 | 2/2024 | Awad et al. |
| 11,896,325 | B2 | 2/2024 | Clark et al. |
| 11,903,669 | B2 | 2/2024 | Cope et al. |
| 11,906,009 | B2 | 2/2024 | Klem |
| 11,910,997 | B2 | 2/2024 | Fuerst et al. |
| 11,911,120 | B2 | 2/2024 | Freiin von Kapri et al. |
| 11,911,910 | B2 | 2/2024 | Gonenc et al. |
| 11,918,240 | B2 | 3/2024 | Deville et al. |
| 11,918,312 | B2 | 3/2024 | Yu |
| 11,918,423 | B2 | 3/2024 | Kottenstette et al. |
| 11,931,901 | B2 | 3/2024 | Murphy et al. |
| D1,021,103 | S | 4/2024 | Swen |
| 11,998,290 | B2 | 6/2024 | Murphy et al. |
| 12,004,829 | B2 | 6/2024 | Searfoss et al. |
| 12,005,589 | B2 | 6/2024 | Rea et al. |
| 12,035,989 | B2 | 7/2024 | Clark et al. |
| 12,046,363 | B2 | 7/2024 | Shrivastava et al. |
| D1,038,990 | S | 8/2024 | Inwood |
| 12,059,161 | B2 | 8/2024 | Deville et al. |
| 12,059,225 | B2 | 8/2024 | Zhou et al. |
| D1,043,739 | S | 9/2024 | Hernandez |
| 12,076,036 | B2 | 9/2024 | Baron et al. |
| 12,076,099 | B2 | 9/2024 | Shrivastava et al. |
| 12,076,497 | B2 | 9/2024 | Fantuzzi et al. |
| 12,076,505 | B2 | 9/2024 | Haubert |
| 12,082,982 | B2 | 9/2024 | Jhaveri et al. |
| 12,087,024 | B2 | 9/2024 | Djelouah et al. |
| 12,102,290 | B2 | 10/2024 | Sharon et al. |
| 12,114,940 | B2 | 10/2024 | Garcia Kilroy et al. |
| 12,117,624 | B2 | 10/2024 | Fuerst et al. |
| 12,133,700 | B2 | 11/2024 | Miller et al. |
| 12,133,702 | B2 | 11/2024 | Nowlin et al. |
| 12,133,965 | B2 | 11/2024 | Chassot et al. |
| 12,137,990 | B2 | 11/2024 | Walker et al. |
| 12,138,004 | B2 | 11/2024 | Cone et al. |
| 12,138,130 | B2 | 11/2024 | Garbus et al. |
| 12,144,564 | B2 | 11/2024 | Barbagli et al. |
| 12,144,569 | B2 | 11/2024 | Cone et al. |
| 12,144,575 | B2 | 11/2024 | Torabi |
| 12,150,660 | B1 | 11/2024 | Teigen et al. |
| 12,150,796 | B2 | 11/2024 | Wenderow et al. |
| 12,156,666 | B2 | 12/2024 | Trosper et al. |
| 12,156,667 | B2 | 12/2024 | Trosper et al. |
| 12,156,711 | B2 | 12/2024 | Liao et al. |
| 12,157,238 | B2 | 12/2024 | Fredrickson et al. |
| 12,161,419 | B2 | 12/2024 | Fuerst et al. |
| 12,171,505 | B2 | 12/2024 | Barbagli et al. |
| 12,171,543 | B2 | 12/2024 | Duindam et al. |
| 12,177,411 | B2 | 12/2024 | Culman |
| 12,178,387 | B2 | 12/2024 | McDowall et al. |
| 12,178,399 | B2 | 12/2024 | Itkowitz et al. |
| 12,178,526 | B2 | 12/2024 | McKenney et al. |
| 12,178,534 | B2 | 12/2024 | Asadian et al. |
| 12,185,947 | B2 | 1/2025 | Hart |
| 12,191,031 | B2 | 1/2025 | Azizian et al. |
| 12,201,484 | B2 | 1/2025 | Itkowitz et al. |
| 12,201,485 | B2 | 1/2025 | McDowall et al. |
| 12,212,240 | B2 | 1/2025 | Schulz |
| D1,072,942 | S | 4/2025 | Yu |
| 12,350,415 | B2 | 7/2025 | Kumar et al. |
| 12,377,206 | B2 | 8/2025 | Bartholomew et al. |
| 12,383,668 | B2 | 8/2025 | Batarilo et al. |
| 12,396,741 | B2 | 8/2025 | Blacker |
| 12,397,099 | B2 | 8/2025 | Aaron et al. |
| 12,419,501 | B2 | 9/2025 | Canale et al. |
| D1,102,447 | S | 11/2025 | Bartholomew et al. |
| 12,508,093 | B2 | 12/2025 | Lee et al. |
| D1,119,865 | S | 3/2026 | Shad |
| 2002/0019608 | A1 | 2/2002 | Mason |
| 2002/0091372 | A1 | 7/2002 | Cragg et al. |
| 2002/0113501 | A1 | 8/2002 | Doi |
| 2002/0192113 | A1 | 12/2002 | Uffenheimer et al. |
| 2003/0071285 | A1 | 4/2003 | Tsukernik |
| 2003/0100849 | A1 | 5/2003 | Jang |
| 2003/0105451 | A1 | 6/2003 | Westlund et al. |
| 2003/0114739 | A1 | 6/2003 | Fuimaono et al. |
| 2003/0125673 | A1 | 7/2003 | Houde et al. |
| 2004/0068248 | A1 | 4/2004 | Mooney et al. |
| 2004/0097805 | A1 | 5/2004 | Verard et al. |
| 2004/0143225 | A1 | 7/2004 | Callan |
| 2005/0027236 | A1 | 2/2005 | Douk |
| 2005/0077225 | A1 | 4/2005 | Usher et al. |
| 2005/0107667 | A1 | 5/2005 | Danitz |
| 2005/0165276 | A1 | 7/2005 | Belson et al. |
| 2005/0277912 | A1 | 12/2005 | John |
| 2006/0000864 | A1 | 1/2006 | Yoshie |
| 2006/0009737 | A1 | 1/2006 | Whiting |
| 2006/0011501 | A1 | 1/2006 | Itou et al. |
| 2006/0095022 | A1 | 5/2006 | Moll et al. |
| 2006/0146010 | A1 | 7/2006 | Schneider |
| 2006/0200026 | A1 | 9/2006 | Wallace et al. |
| 2006/0200191 | A1 | 9/2006 | Zadno-Azizi |
| 2007/0060879 | A1 | 3/2007 | Weitzner |
| 2007/0060915 | A1 | 3/2007 | Kucklick |
| 2007/0106208 | A1 | 5/2007 | Uber et al. |
| 2007/0142824 | A1 | 6/2007 | Devengenzo |
| 2007/0179473 | A1 | 8/2007 | Masters et al. |
| 2007/0270639 | A1 | 11/2007 | Long |
| 2008/0027464 | A1 | 1/2008 | Moll et al. |
| 2008/0086051 | A1 | 4/2008 | Voegele |
| 2008/0234631 | A1 | 9/2008 | Reis |
| 2008/0255505 | A1 | 10/2008 | Carlson et al. |
| 2008/0262513 | A1 | 10/2008 | Stahler et al. |
| 2008/0319387 | A1 | 12/2008 | Amisar et al. |
| 2009/0012464 | A1 | 1/2009 | Martin |
| 2009/0076445 | A1 | 3/2009 | Furnish |
| 2009/0082722 | A1 | 3/2009 | Munger et al. |
| 2009/0131955 | A1 | 5/2009 | Wenderow et al. |
| 2009/0153374 | A1 | 6/2009 | Maw |
| 2009/0171332 | A1 | 7/2009 | Bonneau |
| 2009/0204078 | A1 | 8/2009 | Mitchell et al. |
| 2009/0247943 | A1 | 10/2009 | Kirschenman et al. |
| 2009/0247993 | A1 | 10/2009 | Kirschenman et al. |
| 2009/0254083 | A1 | 10/2009 | Wallace et al. |
| 2009/0259200 | A1 | 10/2009 | Lampropoulos |
| 2009/0264785 | A1 | 10/2009 | Causevic et al. |
| 2010/0069833 | A1 | 3/2010 | Wenderow et al. |
| 2010/0175701 | A1 | 7/2010 | Reis et al. |
| 2010/0204712 | A1 | 8/2010 | Mallaby |
| 2010/0204713 | A1 | 8/2010 | Ruiz Morales |
| 2010/0280363 | A1 | 11/2010 | Skarda et al. |
| 2010/0286756 | A1 | 11/2010 | Dorn |
| 2010/0305502 | A1 | 12/2010 | Ferry et al. |
| 2011/0004223 | A1 | 1/2011 | Leeflang |
| 2011/0015484 | A1 | 1/2011 | Alvarez et al. |
| 2011/0028894 | A1 | 2/2011 | Foley et al. |
| 2011/0144658 | A1 | 6/2011 | Wenderow et al. |
| 2011/0166447 | A1 | 7/2011 | Windolf |
| 2011/0238010 | A1 | 9/2011 | Kirschenman |
| 2011/0288544 | A1 | 11/2011 | Verin et al. |
| 2011/0313318 | A1 | 12/2011 | Rule et al. |
| 2012/0071822 | A1 | 3/2012 | Romo |
| 2012/0071895 | A1 | 3/2012 | Stahler et al. |
| 2012/0154431 | A1 | 6/2012 | Fram |
| 2012/0172798 | A1 | 7/2012 | Miller et al. |
| 2012/0179032 | A1 | 7/2012 | Bromander et al. |
| 2012/0232476 | A1 | 9/2012 | Bhat |
| 2012/0245595 | A1 | 9/2012 | Kesavadas et al. |

(56) References Cited

U.S. PATENT DOCUMENTS

2012/0316458 A1 12/2012 Rahman
2013/0030408 A1 1/2013 Piferi
2013/0035537 A1 2/2013 Wallace
2013/0053704 A1 2/2013 Bernak et al.
2013/0096551 A1 4/2013 Govari et al.
2013/0131499 A1 5/2013 Chan et al.
2013/0214912 A1 8/2013 Beyar et al.
2013/0231678 A1 9/2013 Wenderow
2014/0058321 A1 2/2014 Wenderow et al.
2014/0066900 A1 3/2014 Blacker
2014/0088411 A1 3/2014 Suehara
2014/0150782 A1 6/2014 Vazales
2014/0163364 A1 6/2014 Perers
2014/0216250 A1 8/2014 Meyer
2014/0228762 A1 8/2014 Capone
2014/0243742 A1 8/2014 Pacheco et al.
2014/0276016 A1 9/2014 Stigall
2014/0276233 A1 9/2014 Murphy
2014/0276389 A1* 9/2014 Walker .................. A61B 34/30 604/95.01
2014/0276948 A1 9/2014 Zirps
2014/0318702 A1 10/2014 Tegg
2015/0005738 A1 1/2015 Blacker
2015/0005745 A1 1/2015 Bergman et al.
2015/0073391 A1 3/2015 Hutchins et al.
2015/0088002 A1 3/2015 Podhajsky
2015/0157252 A1 6/2015 Sabesan
2015/0265807 A1 9/2015 Park
2015/0272683 A1 10/2015 Yang et al.
2015/0314105 A1 11/2015 Gasparyan
2015/0320478 A1 11/2015 Cosman, Jr.
2015/0320479 A1 11/2015 Cosman, Jr.
2015/0320480 A1 11/2015 Cosman, Jr.
2015/0320481 A1 11/2015 Cosman, Jr.
2015/0327875 A1 11/2015 Look
2015/0374483 A1 12/2015 Janardhan
2016/0058513 A1 3/2016 Giorgi
2016/0067448 A1 3/2016 Blacker et al.
2016/0074057 A1 3/2016 Jezierski et al.
2016/0082502 A1 3/2016 Appleby
2016/0178519 A1 6/2016 Zupkofska
2016/0184032 A1 6/2016 Romo
2016/0310702 A1 10/2016 Cabiri
2016/0331944 A1 11/2016 Tai
2016/0367214 A1 12/2016 Myklebust
2016/0374590 A1 12/2016 Wong et al.
2017/0000576 A1 1/2017 Zirps
2017/0014998 A1 1/2017 Langenfeld et al.
2017/0020627 A1 1/2017 Tesar et al.
2017/0027653 A1 2/2017 Kirschenman
2017/0080141 A1 3/2017 Lauer
2017/0135773 A1 5/2017 Lohmeier et al.
2017/0143416 A1 5/2017 Guler et al.
2017/0224224 A1 8/2017 Yu
2017/0252025 A1 9/2017 Cabiri et al.
2017/0281054 A1 10/2017 Stever et al.
2017/0281288 A1 10/2017 Au
2017/0311908 A1 11/2017 Kariv et al.
2017/0317937 A1 11/2017 Dillon
2017/0333000 A1 11/2017 Nystrom et al.
2017/0348060 A1 12/2017 Blacker
2017/0348511 A1 12/2017 Burkholz
2018/0126122 A1 5/2018 Cabiri
2018/0153477 A1 6/2018 Nagale et al.
2018/0161001 A1 6/2018 Seip
2018/0168751 A1 6/2018 Yi et al.
2018/0185104 A1 7/2018 Olson et al.
2018/0199916 A1 7/2018 Sugihara et al.
2018/0250086 A1 9/2018 Grubbs
2018/0360398 A1 12/2018 Wenderow et al.
2019/0008360 A1 1/2019 Peh et al.
2019/0008591 A1 1/2019 Desai
2019/0030324 A1 1/2019 Grace et al.
2019/0076640 A1 3/2019 Bhatnagar et al.
2019/0111237 A1 4/2019 Cabiri et al.
2019/0133666 A1 5/2019 Johnson
2019/0167367 A1 6/2019 Walker et al.
2019/0209026 A1 7/2019 Han et al.
2019/0231373 A1 8/2019 Quick
2019/0254690 A1 8/2019 Cabiri et al.
2019/0254754 A1 8/2019 Johnson
2019/0255297 A1 8/2019 Fischell et al.
2019/0269368 A1 9/2019 Hauck et al.
2019/0274809 A1 9/2019 Kapec
2019/0301913 A1 10/2019 Johnson
2019/0304108 A1 10/2019 Carrell et al.
2019/0336227 A1 11/2019 Murphy et al.
2019/0336674 A1 11/2019 Schermeier
2019/0365485 A1 12/2019 Kottenstette et al.
2019/0380825 A1 12/2019 Perkins et al.
2020/0008891 A1 1/2020 Wenderow et al.
2020/0008896 A1 1/2020 Cone et al.
2020/0009354 A1 1/2020 Wenderow et al.
2020/0016371 A1 1/2020 Blacker
2020/0028181 A1 1/2020 Arugula et al.
2020/0054399 A1 2/2020 Duindam
2020/0054403 A1 2/2020 Zhou et al.
2020/0085528 A1 3/2020 Olson et al.
2020/0129740 A1 4/2020 Kottenstette et al.
2020/0163726 A1 5/2020 Tanner et al.
2020/0170630 A1 6/2020 Wong et al.
2020/0233263 A1* 7/2020 Liu ...................... G09G 3/3258
2020/0242767 A1 7/2020 Zhao et al.
2020/0282186 A1 9/2020 Blacker et al.
2020/0289219 A1 9/2020 Denlinger et al.
2020/0297444 A1 9/2020 Camarillo et al.
2020/0297973 A1 9/2020 Blacker et al.
2020/0306064 A1 10/2020 Perkins et al.
2020/0316340 A1 10/2020 Wenderow et al.
2020/0324084 A1 10/2020 Falb et al.
2020/0338308 A1 10/2020 Saber et al.
2020/0345979 A1 11/2020 Loh et al.
2020/0352494 A1 11/2020 Gable et al.
2020/0368494 A1 11/2020 Parmar
2020/0375671 A1 12/2020 Wenderow et al.
2020/0376249 A1 12/2020 Lockhart
2020/0390503 A1 12/2020 Casas et al.
2020/0397451 A1* 12/2020 Feltyberger .... A61B 17/320758
2020/0405408 A1 12/2020 Shelton, IV et al.
2020/0405410 A1 12/2020 Shelton, IV et al.
2020/0405950 A1 12/2020 Burren
2021/0007816 A1 1/2021 Huang et al.
2021/0022816 A1 1/2021 DeBuys et al.
2021/0030492 A1 2/2021 Wenderow et al.
2021/0031007 A1 2/2021 Alexander
2021/0045622 A1 2/2021 Petroff et al.
2021/0046284 A1 2/2021 Mauch
2021/0060767 A1 3/2021 Guerrera et al.
2021/0068852 A1 3/2021 Spence
2021/0077211 A1 3/2021 Blacker et al.
2021/0093406 A1 4/2021 Blacker et al.
2021/0100627 A1 4/2021 Soper
2021/0100980 A1 4/2021 Blacker
2021/0106346 A1 4/2021 Wallace
2021/0106393 A1 4/2021 Simi et al.
2021/0145532 A1 5/2021 Tucker et al.
2021/0178032 A1 6/2021 Hsu et al.
2021/0178036 A1 6/2021 Nazarifar et al.
2021/0186534 A1 6/2021 Hunt et al.
2021/0192759 A1 6/2021 Lang
2021/0196242 A1 7/2021 Perez
2021/0196413 A1 7/2021 Inoue
2021/0212792 A1 7/2021 Shelton et al.
2021/0220064 A1 7/2021 Kottenstette et al.
2021/0228841 A1 7/2021 Falb et al.
2021/0244434 A1 8/2021 Popa et al.
2021/0247396 A9 8/2021 Penny et al.
2021/0251472 A1 8/2021 Baez
2021/0259884 A1 8/2021 Heeren et al.
2021/0282863 A1 9/2021 Rafii-Tari et al.
2021/0282867 A1 9/2021 Tegg et al.
2021/0282875 A1 9/2021 Sharon et al.
2021/0282893 A1 9/2021 Leo et al.
2021/0290310 A1 9/2021 Laby et al.

(56) References Cited

U.S. PATENT DOCUMENTS

| | | | |
|---|---|---|---|
| 2021/0290320 | A1 | 9/2021 | Mao et al. |
| 2021/0290324 | A1 | 9/2021 | Mintz et al. |
| 2021/0290327 | A1 | 9/2021 | Yates et al. |
| 2021/0298847 | A1 | 9/2021 | Mao et al. |
| 2021/0298850 | A1 | 9/2021 | Huang et al. |
| 2021/0298857 | A1 | 9/2021 | Zheng et al. |
| 2021/0298954 | A1 | 9/2021 | Alvarez et al. |
| 2021/0305639 | A1 | 9/2021 | Ho et al. |
| 2021/0315596 | A1 | 10/2021 | Buck et al. |
| 2021/0353129 | A1 | 11/2021 | Roelle et al. |
| 2021/0361366 | A1 | 11/2021 | Murphy et al. |
| 2021/0369370 | A1 | 12/2021 | Malanoski |
| 2021/0378696 | A1 | 12/2021 | Yang et al. |
| 2021/0393338 | A1 | 12/2021 | Graetzel et al. |
| 2021/0401527 | A1 | 12/2021 | Hassan |
| 2022/0031415 | A1 | 2/2022 | Vargas et al. |
| 2022/0040450 | A1 | 2/2022 | Haubert |
| 2022/0047344 | A1 | 2/2022 | Stepanauskas |
| 2022/0047849 | A1 | 2/2022 | Yee et al. |
| 2022/0096120 | A1 | 3/2022 | Bajo et al. |
| 2022/0125533 | A1 | 4/2022 | Falb |
| 2022/0167984 | A1 | 6/2022 | Shelton, IV |
| 2022/0168000 | A1 | 6/2022 | Naglretter et al. |
| 2022/0168001 | A1 | 6/2022 | Naglretter et al. |
| 2022/0168002 | A1 | 6/2022 | Naglretter et al. |
| 2022/0168049 | A1 | 6/2022 | Tanner et al. |
| 2022/0211452 | A1 | 7/2022 | Clark et al. |
| 2022/0233263 | A1* | 7/2022 | Canale ............... A61M 25/0113 |
| 2022/0233264 | A1 | 7/2022 | Klem |
| 2022/0233820 | A1 | 7/2022 | Clark et al. |
| 2022/0241490 | A1 | 8/2022 | Marass |
| 2022/0313375 | A1 | 10/2022 | Zhang et al. |
| 2022/0323096 | A1 | 10/2022 | Naglretter et al. |
| 2022/0331509 | A1 | 10/2022 | Buck et al. |
| 2022/0370161 | A1 | 11/2022 | Yu |
| 2022/0370706 | A1 | 11/2022 | Meganck |
| 2022/0378522 | A1 | 12/2022 | Zemlok et al. |
| 2023/0000563 | A1 | 1/2023 | Bell et al. |
| 2023/0035508 | A1 | 2/2023 | Clark et al. |
| 2023/0035946 | A1 | 2/2023 | Kapadia |
| 2023/0043432 | A1 | 2/2023 | Kapadia |
| 2023/0046468 | A1 | 2/2023 | Lau et al. |
| 2023/0047098 | A1 | 2/2023 | Lau et al. |
| 2023/0048055 | A1 | 2/2023 | Lau et al. |
| 2023/0048388 | A1 | 2/2023 | Lau et al. |
| 2023/0052862 | A1 | 2/2023 | Lau et al. |
| 2023/0061728 | A1 | 3/2023 | Davis et al. |
| 2023/0098497 | A1 | 3/2023 | Laby |
| 2023/0107693 | A1 | 4/2023 | Walker et al. |
| 2023/0116327 | A1 | 4/2023 | Walker et al. |
| 2023/0116700 | A1 | 4/2023 | Yu et al. |
| 2023/0117715 | A1 | 4/2023 | Ho et al. |
| 2023/0126545 | A1 | 4/2023 | Liu et al. |
| 2023/0202040 | A1 | 6/2023 | Lin et al. |
| 2023/0209018 | A1 | 6/2023 | Alexanderson et al. |
| 2023/0218816 | A1 | 7/2023 | Germain et al. |
| 2023/0218861 | A1 | 7/2023 | Altshuler |
| 2023/0310100 | A1 | 10/2023 | Wenderow et al. |
| 2023/0347110 | A1 | 11/2023 | Wenderow et al. |
| 2023/0355299 | A1 | 11/2023 | Cosman |
| 2023/0380914 | A1 | 11/2023 | Meglan et al. |
| 2023/0380915 | A1 | 11/2023 | Hundertmark |
| 2024/0000524 | A1 | 1/2024 | Gregory |
| 2024/0001101 | A1 | 1/2024 | Wallin et al. |
| 2024/0016557 | A1 | 1/2024 | Hung et al. |
| 2024/0016560 | A1 | 1/2024 | Canale et al. |
| 2024/0019042 | A1 | 1/2024 | Lim |
| 2024/0032949 | A1 | 2/2024 | Yang et al. |
| 2024/0033016 | A1 | 2/2024 | Yang et al. |
| 2024/0033017 | A1 | 2/2024 | Yang et al. |
| 2024/0033018 | A1 | 2/2024 | Yang et al. |
| 2024/0033019 | A1 | 2/2024 | Lau et al. |
| 2024/0033486 | A1 | 2/2024 | Lau et al. |
| 2024/0041480 | A1 | 2/2024 | Bartholomew |
| 2024/0042124 | A1 | 2/2024 | Bartholomew |
| 2024/0042142 | A1 | 2/2024 | Bartholomew |
| 2024/0122612 | A1 | 4/2024 | Bartholomew |
| 2024/0130809 | A1 | 4/2024 | Scheunert et al. |
| 2024/0138862 | A1 | 5/2024 | Beach |
| 2024/0138946 | A1 | 5/2024 | Swoyer |
| 2024/0148458 | A1 | 5/2024 | Bailey |
| 2024/0165415 | A1 | 5/2024 | Grosskopf et al. |
| 2024/0180635 | A1 | 6/2024 | Lau et al. |
| 2024/0180640 | A1 | 6/2024 | Lau et al. |
| 2024/0180641 | A1 | 6/2024 | Lau et al. |
| 2024/0180642 | A1 | 6/2024 | Lau et al. |
| 2024/0180643 | A1 | 6/2024 | Lau et al. |
| 2024/0180650 | A1 | 6/2024 | Lau et al. |
| 2024/0180651 | A1 | 6/2024 | Lau et al. |
| 2024/0180652 | A1 | 6/2024 | Lau et al. |
| 2024/0180653 | A1 | 6/2024 | Lau et al. |
| 2024/0180654 | A1 | 6/2024 | Lau et al. |
| 2024/0180658 | A1 | 6/2024 | Lau et al. |
| 2024/0180659 | A1 | 6/2024 | Lau et al. |
| 2024/0181207 | A1 | 6/2024 | Lau et al. |
| 2024/0181208 | A1 | 6/2024 | Lau et al. |
| 2024/0181213 | A1 | 6/2024 | Lau et al. |
| 2024/0181214 | A1 | 6/2024 | Lau et al. |
| 2024/0181224 | A1 | 6/2024 | Lau et al. |
| 2024/0181298 | A1 | 6/2024 | Lau et al. |
| 2024/0183382 | A1 | 6/2024 | Lau et al. |
| 2024/0197416 | A1 | 6/2024 | Gonzalez |
| 2024/0198039 | A1 | 6/2024 | Wainwright et al. |
| 2024/0198051 | A1 | 6/2024 | Jourdan |
| 2024/0207570 | A1 | 6/2024 | Mar |
| 2025/0032201 | A1 | 1/2025 | Bartholomew et al. |
| 2025/0099089 | A1 | 3/2025 | Chookhach |
| 2025/0177692 | A1 | 6/2025 | Yee et al. |
| 2025/0195835 | A1 | 6/2025 | Totten |
| 2025/0261956 | A1 | 8/2025 | Ray et al. |
| 2025/0319243 | A1 | 10/2025 | Mar |
| 2025/0352717 | A1 | 11/2025 | Bartholomew |
| 2025/0375256 | A1 | 12/2025 | Berry |
| 2025/0375592 | A1 | 12/2025 | Dan |
| 2026/0041414 | A1 | 2/2026 | Schorr |

FOREIGN PATENT DOCUMENTS

| | | | |
|---|---|---|---|
| CN | 103976766 | | 8/2014 |
| CN | 104042259 | | 9/2014 |
| CN | 203935213 | | 11/2014 |
| CN | 204428157 | | 7/2015 |
| CN | 105534599 | | 5/2016 |
| CN | 105616008 | | 6/2016 |
| CN | 105640648 | | 6/2016 |
| CN | 105662586 | | 6/2016 |
| CN | 105662588 | | 6/2016 |
| CN | 105662589 | | 6/2016 |
| CN | 105796179 | | 7/2016 |
| CN | 205598007 | | 9/2016 |
| CN | 106691414 | | 5/2017 |
| CN | 107307909 | | 11/2017 |
| CN | 107349514 | | 11/2017 |
| CN | 107374737 | | 11/2017 |
| CN | 107374738 | | 11/2017 |
| CN | 107374739 | | 11/2017 |
| CN | 107374740 | | 11/2017 |
| CN | 107374741 | | 11/2017 |
| CN | 107550570 | | 1/2018 |
| CN | 107684459 | | 2/2018 |
| CN | 107744405 | | 3/2018 |
| CN | 107744406 | | 3/2018 |
| CN | 107744616 | | 3/2018 |
| CN | 107811624 | | 3/2018 |
| CN | 108158656 | | 6/2018 |
| CN | 108175504 | | 6/2018 |
| CN | 207970143 | | 10/2018 |
| CN | 207979770 | | 10/2018 |
| CN | 207979771 | | 10/2018 |
| CN | 207980153 | | 10/2018 |
| CN | 109567947 | | 4/2019 |
| CN | 208693445 | | 4/2019 |
| CN | 109730779 | A | 5/2019 |
| CN | 109821137 | A | 5/2019 |

(56) References Cited

FOREIGN PATENT DOCUMENTS

| | | | |
|---|---|---|---|
| CN | 208989133 | | 6/2019 |
| CN | 209136865 | | 7/2019 |
| CN | 209137698 | | 7/2019 |
| CN | 110151310 | A | 8/2019 |
| CN | 110236679 | | 9/2019 |
| CN | 209713130 | | 12/2019 |
| CN | 211271130 | | 12/2019 |
| CN | 210056225 | | 2/2020 |
| CN | 111035453 | | 4/2020 |
| CN | 111110353 | | 5/2020 |
| CN | 111110354 | | 5/2020 |
| CN | 111407416 | | 7/2020 |
| CN | 111437033 | | 7/2020 |
| CN | 111449752 | | 7/2020 |
| CN | 210962301 | | 7/2020 |
| CN | 111658154 | | 9/2020 |
| CN | 111772801 | | 10/2020 |
| CN | 211610046 | | 10/2020 |
| CN | 211723416 | U | 10/2020 |
| CN | 111916214 | | 11/2020 |
| CN | 111931626 | | 11/2020 |
| CN | 111933268 | | 11/2020 |
| CN | 112017516 | | 12/2020 |
| CN | 212089719 | | 12/2020 |
| CN | 212089720 | | 12/2020 |
| CN | 112546396 | | 3/2021 |
| CN | 112546397 | | 3/2021 |
| CN | 112587241 | | 4/2021 |
| CN | 213465314 | | 6/2021 |
| CN | 113303913 | | 8/2021 |
| CN | 113304393 | | 8/2021 |
| CN | 113693733 | | 11/2021 |
| EP | 1 776 057 | | 11/2009 |
| EP | 2 124 705 | | 5/2019 |
| FR | 3118406 | | 7/2022 |
| WO | WO 2000/18290 | | 4/2000 |
| WO | WO 2007/102134 | | 9/2007 |
| WO | WO 2008/057887 | | 10/2008 |
| WO | WO 2013/103885 | | 7/2013 |
| WO | WO 2016/191307 | | 12/2016 |
| WO | WO 2017/220010 | | 12/2017 |
| WO | WO 2019/222641 | | 11/2019 |
| WO | WO 2020/031147 | | 2/2020 |
| WO | WO 2020/061240 | | 3/2020 |
| WO | WO 2020/123671 | | 6/2020 |
| WO | WO 2020/130924 | | 6/2020 |
| WO | WO 2021/004255 | | 6/2020 |
| WO | WO 2020/142340 | | 7/2020 |
| WO | WO 2021/011551 | | 7/2020 |
| WO | WO 2020/167749 | | 8/2020 |
| WO | WO 2020/263630 | | 12/2020 |
| WO | WO 2021/011533 | | 1/2021 |
| WO | WO 2021/011554 | | 1/2021 |
| WO | WO 2021/015990 | | 1/2021 |
| WO | WO 2021/126698 | | 6/2021 |
| WO | WO 2021/127426 | | 6/2021 |
| WO | WO 2021/148797 | | 7/2021 |
| WO | WO 2021/183444 | | 9/2021 |
| WO | WO 2021/184444 | | 9/2021 |
| WO | WO 2022/048984 | | 3/2022 |
| WO | WO 2022/115717 | | 6/2022 |
| WO | WO 2022/154979 | | 7/2022 |
| WO | WO 2023/110598 | | 6/2023 |

OTHER PUBLICATIONS

US 12,108,960 B1, 10/2024, Teigen et al. (withdrawn)

Bao et al., Apr. 2018, Operation evaluation in-human of a novel remote-controlled vascular interventional robot, Biomedical Microdevices, 20(2):34.

Bao et al., Feb. 2018, A cooperation of catheters and guidewires-based novel remote-controlled vascular interventional robot, Biomedical Microdevices, 20(1):20.

Bell, Apr. 4, 2019, Coding for Empathy, https://www.youtube.com/watch?v=13tzbxofDVc, screenshot of video.

Bency et al., Apr. 25, 2019, Neural Path Planning: Fixed Time, Near-Optimal Path Generation via Oracle Imitation, arXiv:1904.11102v1 [cs.RO], 8 pp.

Bergman et al., 2020, Robotic-assisted percutaneous coronary intervention, Handbook of Robotic and Image-Guided Surgery, doi: https.//doi.org/10.1016/B978-0-12-814245-5.00020-7.

Chen et al., Feb. 14, 2020, Deep learning robotic guidance for autonomous vascular access, Nature Machine Intelligence, https://doi.org/10.1038/s42256-020-0148-7, 12 pp.

Das et al., Feb. 21, 2019, Learning-Based Proxy Collision Detection for Robot Motion Planning Applications, arXiv:1902.08164v1 [cs.RO], 19 pp.

Das et al., May 29, 2020, Stochastic Modeling of Distance to Collision for Robot Manipulators, arXiv:2005.14391v1 [cs.RO], 8 pp.

Evard, Jun. 2018, Catheter localization utilizing a sensor-enabled guidewire design of a proof-of-concept system, Masters' Thesis, California Polytechnic State University, San Luis Obispo, 186 pp.

Fagogenis et al., Apr. 2019, Autonomous Robotic Intracardiac Catheter Navigation Using Haptic Vision, Science Robotics, 4(29):1-12.

Guo et al., Apr. 13, 2018, Study on real-time force feedback for a master-slave interventional surgical robotic system, Biomedical Microdevices, 20(2):37, 12 pp.

Guo et al., May 20, 2020, Machine learning-based operation skills assessment with vascular difficulty index for vascular intervention surgery, Medical & Biological Engineering & Computing, https://doi.org/10.1007/s11517-020-02195-9, 15 pp.

Guo et al., Oct. 16, 2020, An Improved Visual Auxiliary Algorithm for the Vascular Interventional Surgical Robot based on Neural Network, Proceedings of 2020 IEEE International Conference on Mechatronics and Automation, http://www.guolab.org/Papers/2020/ICMA2020-329.pdf, pp. 1923-1928.

Jiang et al., 2018, Initial clinical trial of robot of endovascular treatment with force feedback and cooperating of catheter and guidewire, Applied Bionics and Biomechanics, vol. 2018, Article ID 9735979, 10 pp.

Johnson et al., Aug. 12, 2020, Dynamically Constrained Motion Planning Networks for Non-Holonomic Robots, arXiv:2008.05112v1 [cs.RO}, 7 pp.

Kagiyama et al., Jul. 31, 2019, First experience of robotic-assisted percutaneous coronary intervention in Japan, Intern Med Advance Publication, doi: Oct. 2016/internalmedicine.3272-19.

Kuang et al., Apr. 2020, Vibration-Based Multi-Axis Force Sensing: Design, Characterization, and Modeling, IEEE Robotics and Automation Letters, 5(2):3082-3089.

Li et al., 2022, An endovascular catheterization robotic system using collaborative operation with magnetically controlled haptic force feedback, Micromachines, 13:505.

Li et al., Jan. 17, 2021, MPC-MPNet: Model-Predictive Motion Planning Networks for Fast, Near-Optimal Planning Under Kinodynamic Constraints, arXiv:2101.06798v1 [cs.RO], 8 pp.

Liu et al., 2021, Animal experiment of a novel neurointerventional surgical robotic system with master-slave mode, Applied Bionics and Biomechanics, vol. 2021, Article ID 8836268, 8 pp.

Qureshi et al., Feb. 2021, Motion Planning Networks: Bridging the Gap Between Learning-Based and Classical Motion Planners, IEEE Transactions on Robotics, 37(1), 19 pp.

Qureshi et al., Jul. 3, 2021, Constrained Motion Planning Networks X, arXiv:2010.08702v2 [cs.RO), 20 pp.

Qureshi et al., Oct. 25-29, 2020, Neural Manipulation Planning on Constraint Manifolds, IEEE Robotics and Automation Letters, 5(4), 8 pp.

Richter et al., Apr. 2021, Autonomous Robotic Suction to Clear the Surgical Field for Hemostasis Using Image-Based Blood Flow Detection, IEEE Robotics and Automation Letters, 6(2), 8 pp.

Sapsalev et al., 2016, Structural model of a magnetic coupling, 17th International Conference of Young Specialists on Micro/Nanotechnologies and Electron Devices EDM 2016, pp. 555-558.

Schreiber et al., Sep. 15, 2020, ARCSnake: An Archimedes Screw-Propelled, Reconfigurable Serpentine Robot for Complex Environments, 2020 IEEE International Conference on Robotics and Automation (ICRA), 6 pp.

(56) References Cited

OTHER PUBLICATIONS

Sganga et al., Sep. 15, 2018, OffsetNet: Deep Learning for Localization in the Lung using Rendered Images, arXiv:1809.05645v1 [cs.CV], 7 pp.
Sganga, May 22, 2020, Webinar: Autonomous Surgical Robots, https://www.youtube.com/watch?v=QRO2KnfGlgo, screenshot of video.
Wang et al., Feb. 3, 2018, Online measuring and evaluation of guidewire inserting resistance forlrobotic interventional surgery systems, Microsystem Technologies, https://doi/org/10.1007/s00542-018-03750-4.
Wilcox et al., Jan. 2020, SOLAR-GP: Sparse Online Locally Adaptive Regression Using Gaussian Processes for Bayesian Robot Model Learning and Control, EEE Robotics and Automation Letters, 5(2), 8 pp.
Yip et al., 2017, Autonomous Control of Continuum Robot Manipulators for Complex Cardiac Ablation Tasks, Journal of Medical Robotics Research, 2(1),: 1750002-1-1750002-13.
Yip et al., Jul. 10, 2017, Robot Autonomy for Surgery, https://arxiv.org/pdf/1707.03080.pdf, 33 pp.
Zhao et al., Apr. 2, 2018, Operating force information on-line acquisition of a novel slave manipulator for vascular interventional surgery, Biomedical Microdevices, 20(2):33, 13 pp.
Zhou et al., 2021, ADRC-based control method for the vascular intervention master-slave surgical robotic system, Micromachines, 12:1439.
International Search Report and Written Opinion dated May 28, 2024 in application No. PCT/US2023/084825.

* cited by examiner

SYSTEM WITH REMOVABLE HUBS FOR MANUAL AND ROBOTIC PROCEDURE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57. The present application claims priority to U.S. Provisional Patent Application No. 63/434,040, filed Dec. 20, 2022, titled METHOD OF PERFORMING A ROBOTIC AND MANUAL NEUROVASCULAR PROCEDURE, the entire content of which is incorporated by reference herein for all purposes and forms a part of this specification.

BACKGROUND

Field

The present application relates to vascular procedures, and more particularly, to systems and methods of performing robotic and manual vascular procedures.

Description of the Related Art

A variety of neurovascular procedures can be accomplished via a transvascular access, including thrombectomy, diagnostic angiography, embolic coil deployment and stent placement. However, the delivery of neurovascular care is limited or delayed by a variety of challenges. For example, there are not enough trained interventionalists and centers to meet the current demand for neuro interventions. Neuro interventions are difficult, with complex set up requirements and demands on the surgeon's dexterity. With two hands, the surgeon must exert precise control over 3-4 coaxial catheters plus manage the fluoroscopy system and patient position.

Long, tortuous anatomy, requires delicate, precise maneuvers. Inadvertent catheter motion can occur due to energy storage and release caused by frictional interplay between coaxial shafts and the patient's vasculature. Supra-aortic access necessary to reach the neurovasculature is challenging to achieve, especially Type III arches. Once supra-aortic access is achieved, adapting the system for neurovascular treatments is time consuming and requires guidewire and access catheter removal and addition of a procedure catheter (and possibly one or more additional catheters) to the stack.

Thus, there remains a need for a supra-aortic access and neurovascular site access system that addresses some or all these challenges and increases the availability of neurovascular procedures. Preferably, the system is additionally capable of driving devices further distally through the supra-aortic access to accomplish procedures in the intracranial vessels.

SUMMARY

There is provided a method of performing a neurovascular procedure. The method includes providing a multi-catheter assembly including a first subset of interventional devices and a second subset of interventional devices detachably couplable to the first subset of interventional devices, coupling the first subset of interventional devices to a robotic drive system, and robotically driving the multi-catheter assembly to achieve supra-aortic access while the second subset of interventional devices is coupled to the first subset of interventional devices. The method includes uncoupling the second subset of interventional devices from the first subset of interventional devices, manually driving the second subset of interventional devices to a neurovascular site, and performing a neurovascular procedure using the second subset of interventional devices.

The first subset of interventional devices can include an access catheter. Coupling the first subset of interventional devices to the drive system can include magnetically coupling a hub of the access catheter to a first drive magnet. The first subset of interventional devices can include a guidewire. The second subset of interventional devices can include a procedure catheter and a guide catheter. The neurovascular procedure can include a neurovascular thrombectomy. The procedure catheter can be detachably couplable to the access catheter or a hub of the access catheter via a luer lock or a hemostatic valve. Uncoupling the second subset of interventional devices from the first subset of interventional devices can include uncoupling the procedure catheter from the access catheter or the hub of the access catheter. The guide catheter can be detachably couplable to the procedure catheter via a luer lock or a hemostatic valve. The method can include uncoupling the guide catheter from the procedure catheter. The method can include proximally removing the access catheter prior to performing the neurovascular procedure using the procedure catheter. The second subset of interventional devices can include a guidewire. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a clot retriever. The procedure catheter can be a balloon catheter. The procedure catheter can be a catheter to facilitate percutaneous valve repair or replacement. The procedure catheter can be an ablation catheter.

There is also provided a system for performing a vascular procedure. The system includes a robotic drive system and one or more hub assemblies. The one or more hub assemblies are operatively coupled to the robotic drive system. Each of the one or more hub assemblies include a mount, a hub, and an interventional device. The hubs are removably coupled to the mounts. The interventional devices are coupled to the hubs. For each of the one or more hub assemblies, the mount is configured to be driven by the robotic drive system to drive the interventional device within a vasculature of a patient. For each of the one or more hub assemblies, the hub is configured to be uncoupled from the mount while the interventional device is positioned within the vasculature of the patient. For each of the one or more hub assemblies, the hub is configured to be manually manipulated to navigate the interventional device to a vascular site while the hub is uncoupled from the mount.

The robotic drive system may further include a drive table and one or more hub adapters axially movable within the drive table. Each of the one or more hub assemblies may be positioned to move axially along the drive table and may be magnetically coupled to a corresponding one of the one or more hub adapters. The mount of each of the one or more hub assemblies may be configured to magnetically couple to the corresponding one of the one or more hub adapters. The interventional device of at least one of the one or more hub assemblies may be configured to perform a vascular procedure. The vascular procedure may include a neurovascular thrombectomy. One or more hub assemblies can include a first hub assembly, a second hub assembly, a third hub assembly, and a fourth assembly. Interventional devices of the one or more hub assemblies can be coaxially nested. The one or more hub assemblies can include one or more of an access catheter hub assembly having an access catheter, a guidewire hub assembly having a guidewire, a procedure catheter hub assembly having a procedure catheter, and a guide catheter hub assembly having a guide catheter. At least one of the one or more hub assemblies can be configured to receive an additional interventional device therethrough. The hub of the at least one of the one or more hub assemblies can be configured to receive an additional interventional device therethrough.

There is also provided a method of performing a vascular procedure. The method includes coupling a plurality of hub assemblies to a robotic drive system, the plurality of hub assemblies including a first hub assembly including a first mount, a first hub removably coupled to the first mount, and a first interventional device coupled to the first hub, and a second hub assembly including a second mount, a second hub removably coupled to the second mount, and a second interventional device coupled to the second hub. The method includes robotically driving the first hub assembly and the second hub assembly to drive the first interventional device and the second interventional device within a vasculature of a patient, and uncoupling the second hub from the second mount while the second interventional device is positioned within the vasculature of the patient.

Robotically driving the first hub assembly and the second hub assembly to drive the first interventional device and the second interventional device within a vasculature of a patient can include driving the first interventional device and the second interventional device to achieve supra-aortic access. The method can further include manually driving the second hub while the second hub is uncoupled from the second mount to drive the second interventional device to a vascular site. The method can further include inserting a third interventional device through a lumen of the second interventional device and manually driving the third interventional device into the vasculature of the patient. The method can further include performing a vascular procedure using the third interventional device. The vascular procedure can be a neurovascular thrombectomy. The third interventional device can be a stent retriever or a stent retriever catheter. The first interventional device can be a guide catheter and the second interventional device can be a procedure catheter configured to extending within a lumen of the procedure catheter. Uncoupling the second hub from the second mount can be performed while the procedure catheter is positioned within the lumen of the guide catheter and while the first hub is coupled to the first mount. Coupling the plurality of hub assemblies to the robotic drive system can include magnetically coupling the first mount to a first hub adapter through a sterile barrier and magnetically coupling a second hub adapter to a second mount through the sterile barrier. The first interventional device can be a procedure catheter and the second interventional device can be a guide catheter, wherein the procedure catheter can be positioned within the lumen of the guide catheter while driving the first hub assembly and the second hub assembly, wherein the method further includes withdrawing the procedure catheter from the lumen of the guide catheter prior to uncoupling the second hub from the second mount. The method can further include inserting a third interventional device through a lumen of the guide catheter after the second hub is detached from the first hub and manually driving the third interventional device into the vasculature of the patient.

A system for performing a vascular procedure including a robotic drive system, a multi-catheter assembly. The multi-catheter assembly includes a first subset of interventional devices and a second subset of interventional devices. The first subset of interventional devices is coupled to the robotic drive system and the second subject of interventional devices is removably coupled to the first subset of interventional devices. The multi-catheter assembly is configured to be robotically driven by the robotic drive system to achieve supra-aortic access while the second subset of interventional devices is coupled to the first subset of interventional devices. The second subset of interventional devices is configured to be manually driven to a vascular site while the second subset of interventional devices is uncoupled from the first subset of interventional devices.

The second subset of interventional devices can be configured to perform a vascular procedure. The vascular procedure can include a vascular thrombectomy. The first subset of interventional devices can be coaxially nested with the second subset of interventional devices. The first subset of interventional devices can include an access catheter and a guidewire. The second subset of interventional devices can include a procedure catheter and a guide catheter. The procedure catheter is detachably couplable to the access catheter or a hub of the access catheter via a luer lock or a hemostatic valve. The second subset of interventional devices can be uncoupled from the first subset of interventional devices by uncoupling the procedure catheter from the access catheter or the hub of the access catheter. The guide catheter can be detachably couplable to the procedure catheter via a luer lock or a hemostatic valve. The procedure catheter can be an aspiration catheter. The procedure catheter can be an embolic deployment catheter. The procedure catheter can be a stent deployment catheter, a flow diverter deployment catheter, a stent retriever catheter, a clot retriever, a balloon catheter, a catheter to facilitate percutaneous valve repair or replacement, an ablation catheter, and/or a coil delivery catheter. The first subset of interventional devices can be coupled to the drive system via a magnetically coupling.

There is also provided a method of performing a vascular procedure. The method includes providing a multi-catheter assembly, coupling a first subset of interventional devices to a robotic drive system; robotically driving the multi-catheter assembly to achieve supra-aortic access while a second subset of interventional devices is coupled to a first subset of interventional devices; uncoupling the second subset of interventional devices from the first subset of interventional devices; manually driving the second subset of interventional devices to a procedure site; and performing a vascular procedure using the second subset of interventional devices. The multi-catheter assembly includes the first subset of interventional devices and the second subset of interventional devices. The second subset of interventional devices is detachably couplable to the first subset of interventional devices.

The first subset of interventional devices can include an access catheter. Coupling the first subset of interventional devices to the drive system can include magnetically coupling a hub of the access catheter to a first drive magnet. The first subset of interventional devices can include a guidewire. The second subset of interventional devices can include a procedure catheter and a guide catheter. The vascular procedure can include a neurovascular thrombectomy. The procedure catheter can be detachably couplable to the access catheter or a hub of the access catheter via a luer lock or a hemostatic valve. Uncoupling the second subset of interventional devices from the first subset of interventional devices can include uncoupling the procedure catheter from the access catheter or the hub of the access catheter. The guide catheter can be detachably couplable to the procedure catheter via a luer lock or a hemostatic valve. The method can further include uncoupling the guide catheter from the procedure catheter. The method can further include proximally removing the access catheter prior to performing the vascular procedure using the procedure catheter. The second subset of interventional devices can include a guidewire. The procedure catheter can be an aspiration catheter, an embolic deployment catheter, a stent deployment catheter, a flow diverter deployment catheter, a diagnostic angiographic catheter, a stent retriever catheter, a clot retriever, a balloon catheter, a catheter to facilitate percutaneous valve repair or replacement, an ablation catheter, and/or a coil delivery catheter.

DETAILED DESCRIPTION

In certain embodiments, a system is provided for advancing a guide catheter from a femoral artery or radial artery access into the ostium of one of the great vessels at the top of the aortic arch, thereby achieving supra-aortic access. A surgeon can then take over and advance interventional devices into the cerebral vasculature via the robotically placed guide catheter.

In some implementations, the system may additionally be configured to robotically gain intra-cranial vascular access and to perform an aspiration thrombectomy or other neuro vascular procedure.

A drive table can be positioned over or alongside the patient, and configured to axially advance, retract, and in some cases rotate and/or laterally deflect two or three or more different (e.g., concentrically or side by side oriented) intravascular devices. The hub is moveable along a path along the surface of the drive table to advance or retract the interventional device as desired. Each hub may also contain mechanisms to rotate or deflect the device as desired, and is connected to fluid delivery tubes (not shown) of the type conventionally attached to a catheter hub. Each hub can be in electrical communication with an electronic control system, either via hard wired connection, RF wireless connection or a combination of both.

Each hub is independently movable across the surface of a sterile field barrier membrane carried by the drive table. Each hub is releasably magnetically coupled to a unique drive carriage on the table side of the sterile field barrier. The drive system independently moves each hub in a proximal or distal direction across the surface of the barrier, to move the corresponding interventional device proximally or distally within the patient's vasculature.

The carriages on the drive table, which magnetically couple with the hubs to provide linear motion actuation, are universal. Functionality of the catheters/guidewire are provided based on what is contained in the hub and the shaft designs. This allows flexibility to configure the system to do a wide range of procedures using a wide variety of interventional devices on the same drive table. Additionally, the interventional devices and methods disclosed herein can be readily adapted for use with any of a wide variety of other drive systems (e.g., any of a wide variety of robotic surgery drive systems).

Figure 1:
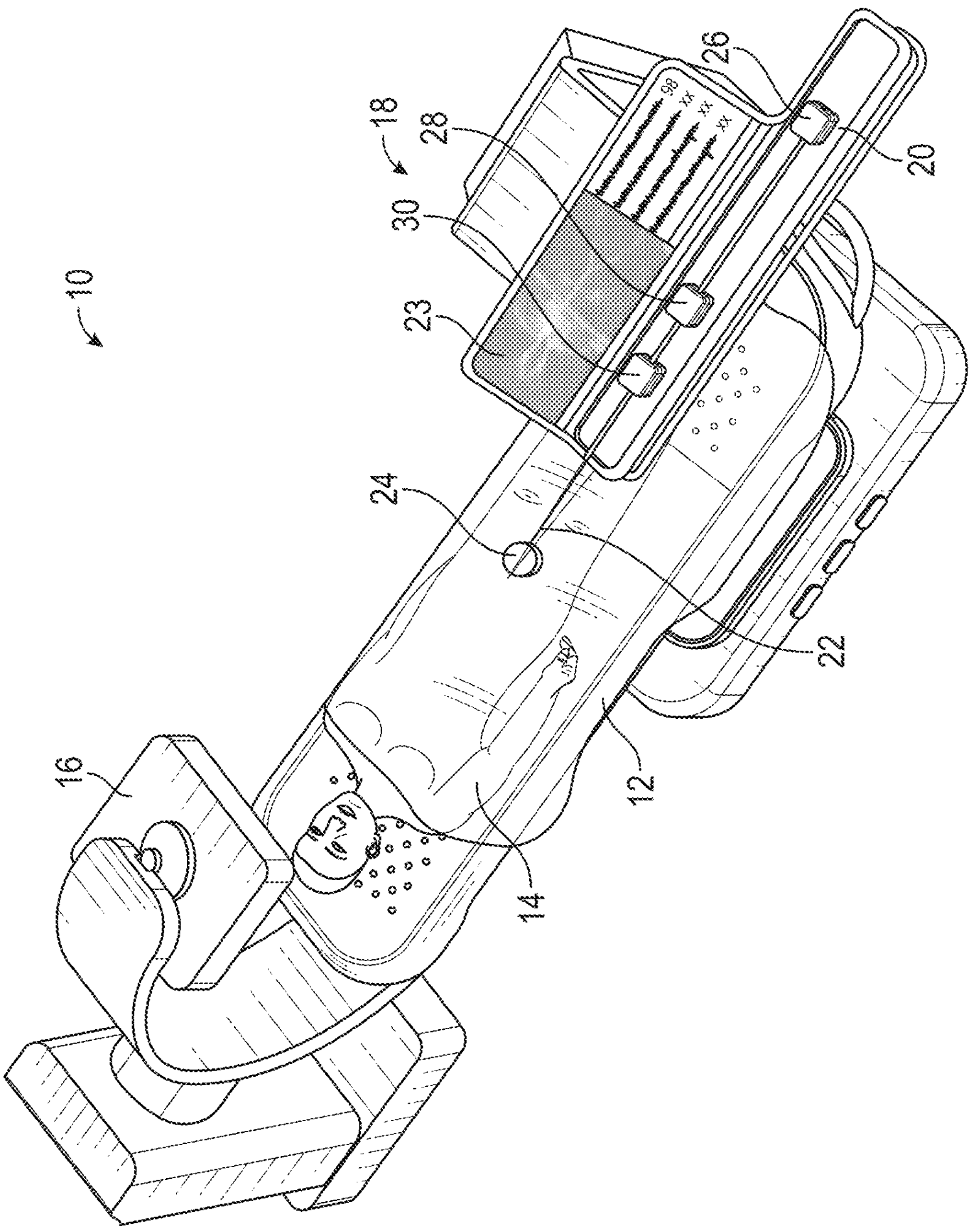
FIG. 1 is a schematic perspective view of an interventional setup having an imaging system, a patient support table, and a robotic drive system in accordance with the present disclosure.

FIG. 1 is a schematic perspective view of an interventional setup 10 having a patient support table 12 for supporting a patient 14. An imaging system 16 may be provided, along with a robotic interventional device drive system 18 in accordance with the present disclosure.

The drive system 18 may include a support table 20 for supporting, for example, a guidewire hub 26, an access catheter hub 28 and a guide catheter hub 30. In the present context, the term 'access' catheter can be any catheter having a lumen with at least one distally facing or laterally facing distal opening, that may be utilized to aspirate thrombus, provide access for an additional device to be advanced therethrough or therealong, or to inject saline or contrast media or therapeutic agents.

More or fewer interventional device hubs may be provided depending upon the desired clinical procedure. For example, in certain embodiments, a diagnostic angiogram procedure may be performed using only a guidewire hub 26 and an access catheter hub 28 for driving a guidewire and an access catheter (in the form of a diagnostic angiographic catheter), respectively. Multiple interventional devices 22 extend between the support table 20 and (in the illustrated example) a femoral access point 24 on the patient 14. Depending upon the desired procedure, access may be achieved by percutaneous or cut down access to any of a variety of arteries or veins, such as the femoral artery or radial artery. Although disclosed herein primarily in the context of neuro vascular access and procedures, the robotic drive system and associated interventional devices can readily be configured for use in a wide variety of additional medical interventions, in the peripheral and coronary arterial and venous vasculature, gastrointestinal system, lymphatic system, cerebral spinal fluid lumens or spaces (such as the spinal canal, ventricles, and subarachnoid space), pulmonary airways, treatment sites reached via trans ureteral or urethral or fallopian tube navigation, or other hollow organs or structures in the body (for example, in intra-cardiac or structural heart applications, such as valve repair or replacement, or in any endoluminal procedures).

A display 23 such as for viewing fluoroscopic images, catheter data (e.g., fiber Bragg grating fiber optics sensor data or other force or shape sensing data) or other patient data may be carried by the support table 20 and or patient support 12. Alternatively, the physician input/output interface including display 23 may be remote from the patient, such as behind radiation shielding, in a different room from the patient, or in a different facility than the patient.

In the illustrated example, a guidewire hub 26 is carried by the support table 20 and is moveable along the table to advance a guidewire into and out of the patient 14. An access catheter hub 28 is also carried by the support table 20 and is movable along the table to advance the access catheter into and out of the patient 14. The access catheter hub may also be configured to rotate the access catheter in response to manipulation of a rotation control, and may also be configured to laterally deflect a deflectable portion of the access catheter, in response to manipulation of a deflection control.

Figure 2:
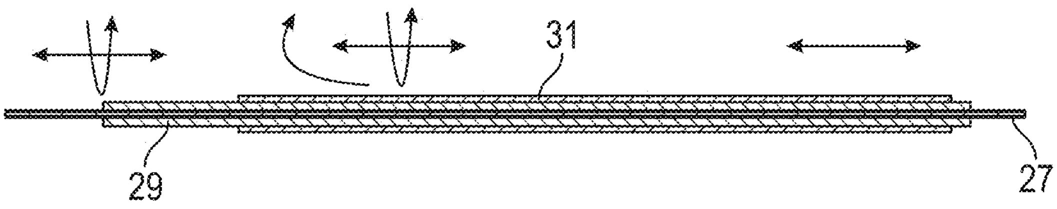
FIG. 2 is a longitudinal cross section showing the concentric relationship between a guidewire having two degrees of freedom, an access catheter having 3 degrees of freedom and a guide catheter having one degree of freedom.

FIG. 2 is a longitudinal cross section schematically showing the motion relationship between a guidewire 27 having two degrees of freedom (axial and rotation), an access catheter 29 having three degrees of freedom (axial, rotational and lateral deflection) and a guide catheter 31, having one degree of freedom (axial).

Figure 3A:
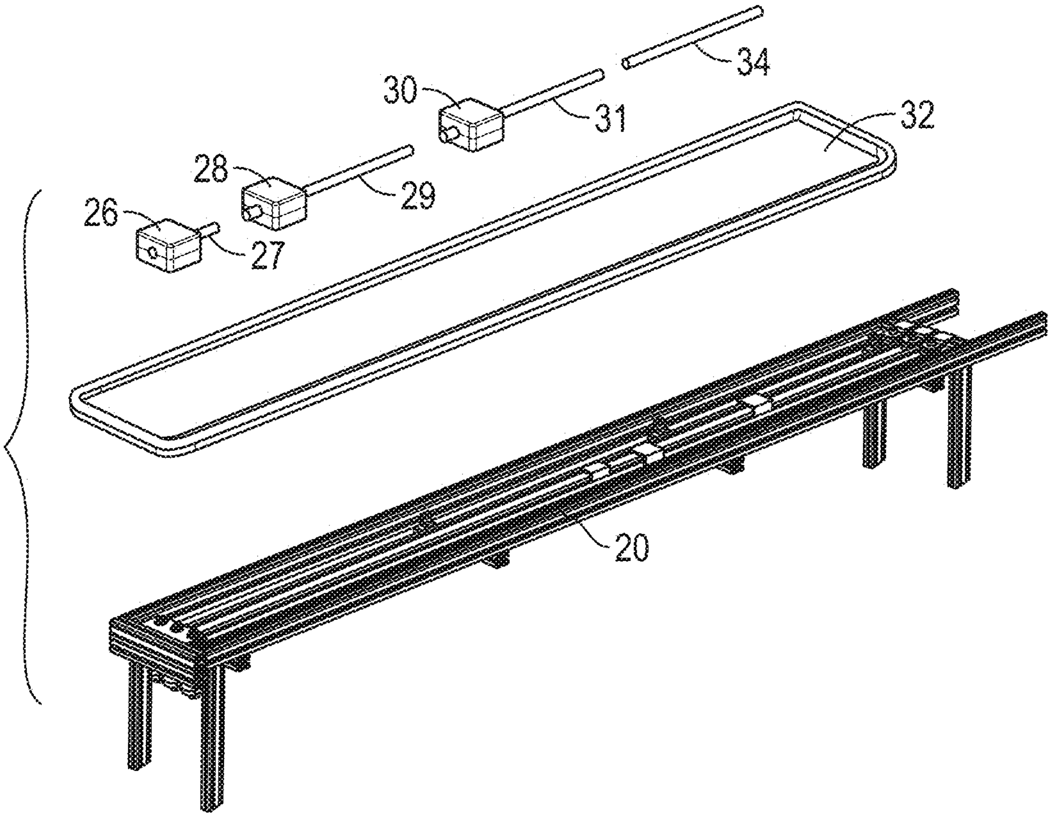
FIG. 3A is an exploded schematic view of interventional device hubs separated from a support table by a sterile barrier.

Referring to FIG. 3A, the support table 20 includes a drive mechanism described in greater detail below, to independently drive the guidewire hub 26, access catheter hub 28, and guide catheter hub 30. An anti-buckling feature 34 may be provided in a proximal anti-buckling zone for resisting buckling of the portion of the interventional devices spanning the distance between the support table 20 and the femoral artery access point 24. The anti-buckling feature 34 may comprise a plurality of concentric telescopically axially extendable and collapsible tubes through which the interventional devices extend.

Alternatively, a proximal segment of one or more of the device shafts may be configured with enhanced stiffness to reduce buckling under compression. For example, a proximal reinforced segment may extend distally from the hub through a distance of at least about 5 centimeters or 10 centimeters but typically no more than about 120 centimeters or 100 centimeters to support the device between the hub and the access point 24 on the patient. Reinforcement may be accomplished by using metal or polymer tubing or embedding at least one or two or more axially extending elements into the wall of the device shafts, such as elongate wires or ribbons. In some implementations, the extending element may be hollow and protect from abrasion, buckling, or damage at the inputs and outputs of the hubs. In some embodiments, the hollow extending element may be a hollow and flexible coating attached to a hub. The hollow, extending element (e.g., a hollow and flexible coating) may cover a portion of the device shaft when threaded through the hubs. In some embodiments in which the hollow extending element is a coating, the coating may be attached to a portion of a hub such that threading the catheter device through the hub 26, 28, or 30 threads the catheter device through the coating as well. In some implementations, an anti-buckling device may be installed on or about or surrounding a device shaft to avoid misalignment or insertion angle errors between hubs or between a hub and an insertion point. The anti-buckling device may be a laser cut hypotube, a spring, telescoping tubes, tensioned split tubing, or the like.

In some implementations, a number of deflection sensors may be placed along a catheter length to identify buckling. Identifying buckling may be performed by sensing that a hub is advancing distally, while the distal tip of the catheter or interventional device has not moved. In some implementations, the buckling may be detected by sensing that an energy load (e.g., due to friction) has occurred between catheter shafts.

Alternatively, thin tubular stiffening structures can be embedded within or carried over the outside of the device wall, such as a tubular polymeric extrusion or length of hypo-tube. Alternatively, a removable stiffening mandrel may be placed within a lumen in the proximal segment of the device, and proximally removed following distal advance of the hub towards the patient access site, to prevent buckling of the proximal shafts during distal advance of the hub. Alternatively, a proximal segment of one or more of the device shafts may be constructed as a tubular hypo tube, which may be machined (e.g., with a laser) so that its mechanical properties vary along its length. This proximal segment may be formed of stainless steel, nitinol, and/or cobalt chrome alloys, optionally in combination with polymer components which may provide for lubricity and hydraulic sealing. In some embodiments, this proximal segment may be formed of a polymer, such as polyether ether ketone (PEEK). Alternatively, the wall thickness or diameter of the interventional device can be increased in the anti-buckling zone.

In certain embodiments, a device shaft having advanced stiffness (e.g., axially and torsionally) may provide improved transmission of motion from the proximal end of the device shaft to the distal end of the device shaft. For example, the device shafts may be more responsive to motion applied at the proximal end. Such embodiments may be advantageous for robotic driving in the absence of haptic feedback to a user.

In some embodiments, a flexible coating can be applied to a device shaft and/or hub to reduce frictional forces between the device shaft and/or hub and a second device shaft when the second device shaft passes therethrough.

The interventional device hubs may be separated from the support table 20 by sterile barrier 32. Sterile barrier 32 may comprise a thin plastic membrane such as polyethylene terephthalate (PET), polyethylene terephthalate glycol (PETG), polyethylene terephthalate (PETE), high-density polyethylene (HDPE), polyvinyl chloride (PVC), low-density polyethylene (LDPE), polypropylene (PP), polystyrene (PS), or styrene. This allows the support table 20 and associated drive system to reside on a non-sterile (lower) side of sterile barrier 32. The guidewire hub 26, access catheter hub 28, guide catheter hub 30 and the associated interventional devices are all on a sterile (top) side of the sterile barrier 32. The sterile barrier is preferably waterproof and can also serve as a tray used in the packaging of the interventional devices, discussed further below. The interventional devices can be provided individually or as a coaxially preassembled kit that is shipped and stored in the tray and enclosed within a sterile packaging.

FIGS. 3B-3F schematically illustrate an alternate sterile barrier in the form of a dual function sterile barrier for placement on the support table during the interventional procedure, and shipping tray, having one or more storage channels for carrying sterile interventional devices. The sterile barrier may also act as a sterile work surface for preparation of catheters or other devices during a procedure.

Figure 3B:
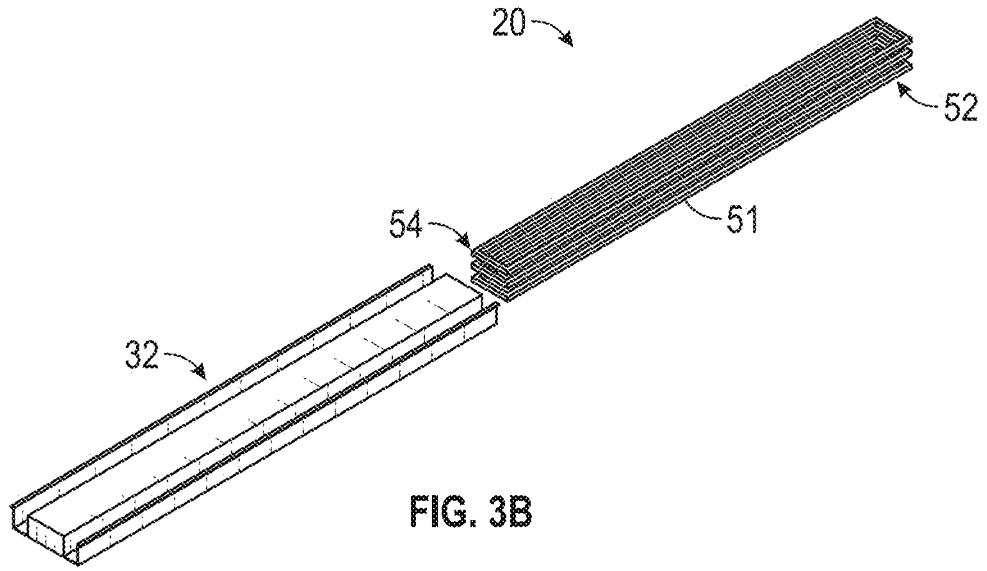
FIGS. 3B-3F show an alternate sterile barrier in the form of a shipping tray having one or more storage channels for carrying interventional devices.
Figure 3C:
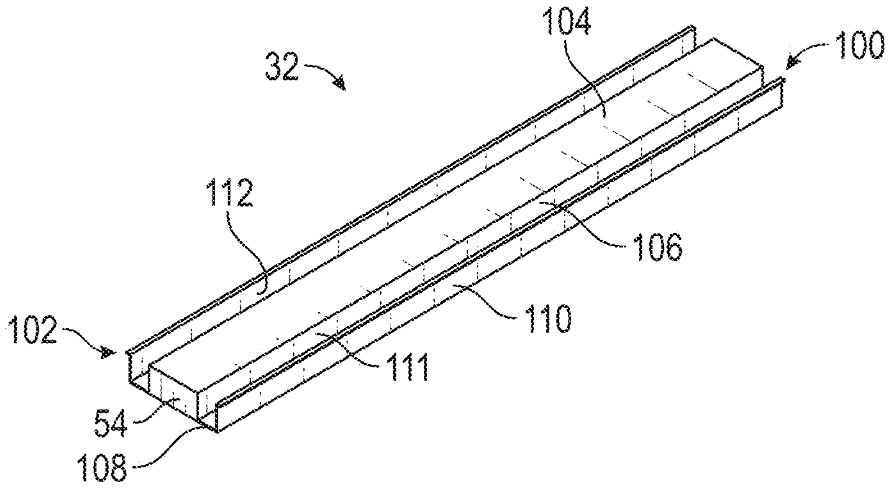

Referring to FIGS. 3B and 3C, there is illustrated a sterile barrier 32 in the form of a pre-shaped tray, for fitting over an elongate support table 20. In use, the elongate support table 20 would be positioned below the sterile barrier 32. The sterile barrier 32 extends between a proximal end 100 and a distal end 102 and includes an upper support surface 104 for supporting the interventional device hubs. In one implementation, the support surface 104 has an axial length greater than the length of the intended interventional devices, in a linear drive configuration.

The length of support surface 104 will typically be at least about 100 centimeters and within the range of from about 100 centimeters to about 2.7 meters. Shorter lengths may be utilized in a system configured to advance the drive couplers along an arcuate path. In some embodiments, two or more support surfaces may be used instead of a single support surface 104. The two or more support surfaces may have a combined length between 100 centimeters to about 2.7 meters. The width of the linear drive table is preferably no more than about 30 to about 80 centimeters.

At least a first channel 106 may be provided, extending axially at least a portion of the length of the support table 20. In the illustrated implementation, first channel 106 extends the entire length of the support table 20. Preferably, the first channel 106 has a sufficient length to hold the interventional devices, and sufficient width and depth to hold the corresponding hubs (for example, by providing lateral support to prevent dislodgment of the hubs when forces are applied to the hubs). First channel 106 is defined within a floor 108, outer side wall 110 and inner side wall 111, forming an upwardly facing concavity. Optionally, a second channel 112 may be provided. Second channel 112 may be located on the same side or the opposite side of the upper support surface 104 from the first channel 106. Two or three or more additional recesses such as additional channels or wells may be provided, to hold additional medical devices or supplies that may be useful during the interventional procedure as well as to collect fluids and function as wash basins for catheters and related devices.

Figure 3D:
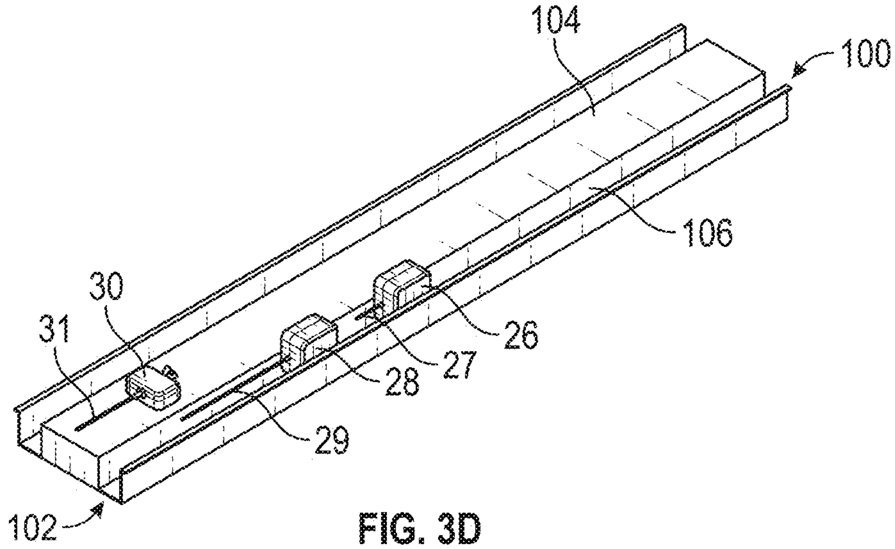

Referring to FIG. 3D, the guide catheter hub 30 is shown positioned on the upper support surface 104, and magnetically coupled to the corresponding coupler holding the drive magnets, positioned beneath the sterile barrier 32. The access catheter hub 28 and access catheter 29, and guidewire hub 26 and guidewire 27 are illustrated residing within the first channel 106 such as before introduction through the guide catheter 31 or following removal from the guide catheter 31.

The interventional devices may be positioned within the channel 106 and enclosed in a sterile barrier for shipping. At the clinical site, an upper panel of the sterile barrier may be removed, or a tubular sterile barrier packaging may be opened and axially removed from the support table 20 and sterile barrier 32 assembly, exposing the sterile top side of the sterile barrier tray and any included interventional devices. The interventional devices may be separately carried in the channel, or preassembled into an access assembly or procedure assembly, discussed in additional detail below.

Figure 3E:
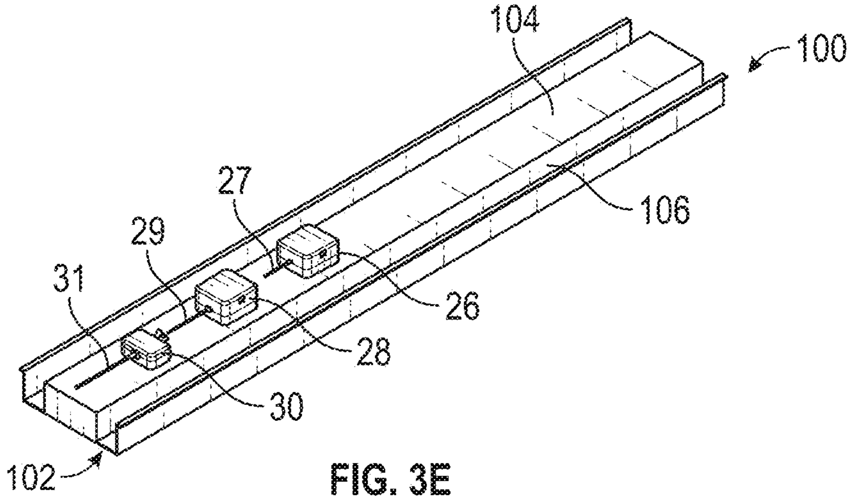
Figure 3F:
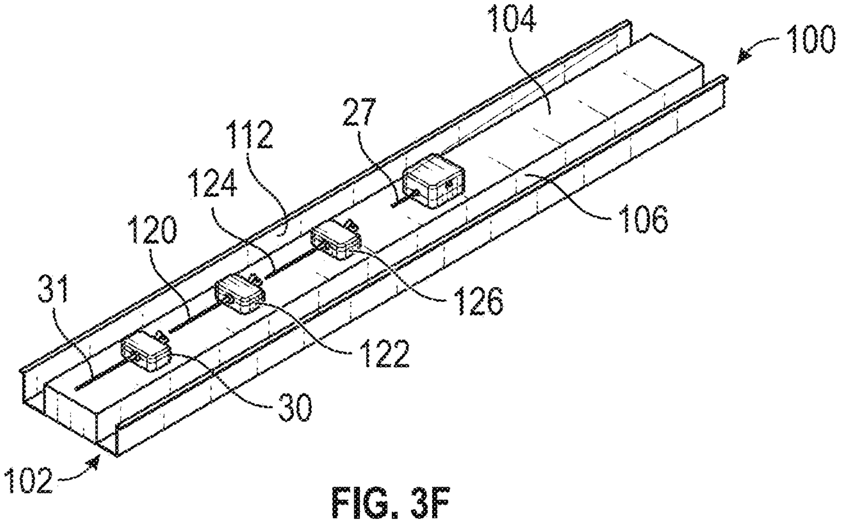

FIGS. 3D-3F illustrate the support table with sterile barrier in place, and in FIG. 3E, the interventional devices configured in an access assembly for aortic access, following coupling of the access assembly to the corresponding carriages beneath the sterile barrier. The access assembly may be preassembled with the guidewire fully advanced through the access catheter which is in turn fully advanced through the guide catheter. In embodiments in which the access catheter or other catheters are pre-shaped (i.e., pre-curved or not straight), the guidewire and/or outer catheters may be positioned so that relatively stiff sections are not superimposed with curved stiffer sections of the pre-shaped catheter, for example, to avoid creep or straightening of the pre-shaped catheter and/or introduction of a curve into an otherwise straight catheter. This access assembly may be lifted out of the channel 106 and positioned on the support surface 104 for coupling to the respective drive magnets and introduction into the patient. The guide catheter hub 30 is the distal most hub. Access catheter hub 28 is positioned proximally of the guide catheter hub, so that the access catheter 29 can extend distally through the guide catheter. The guidewire hub 26 is positioned most proximally, in order to allow the guidewire 27 to advance through the access catheter 29 and guide catheter 31.

A procedure assembly is illustrated in FIG. 3F following introduction of the procedure assembly through the guide catheter 31 that was used to achieve supra-aortic access. In this implementation, guide catheter 31 remains the distal most of the interventional devices. A first procedure catheter 120 and corresponding hub 122 is illustrated extending through the guide catheter 31. An optional second procedure catheter 124 and corresponding hub 126 is illustrated extending through the first procedure catheter 120. The guidewire 27 extends through at least a portion of the second procedure catheter 124 in a rapid exchange version of second procedure catheter 124, or the entire length of second procedure catheter 124 in an over the wire implementation.

As is discussed in greater detail in connection with FIG. 17, the multi catheter stack may be utilized to achieve both access and the intravascular procedure without the need for catheter exchange. This may be accomplished in either a manual or a robotically driven procedure. In one example, the guide catheter 31 may comprise a catheter having an inner diameter of at least about 0.08 inches and in one implementation about 0.088 inches. The first procedure catheter 120 may comprise a catheter having an inner diameter within the range of from about 0.065 inches to about 0.075 inches and in one implementation, the first procedure catheter 120 has an inner diameter of about 0.071 inches. The second procedure catheter 124 may be an access catheter having an OD sized to permit advance through the first procedure catheter 120. The second procedure catheter may be steerable, having a deflection control 2908 configured to laterally deflect a distal end of the catheter. The second procedure (access) catheter may also have an inner lumen sized to allow an appropriately sized guidewire to remain inside the second procedure catheter while performing contrast injections through the second procedure catheter.

In certain embodiments, the catheter 31 may be a 'large bore' access catheter or guide catheter having a diameter of at least about 0.075 or at least about 0.080 inches in diameter. The catheter 120 may be an aspiration catheter having a diameter within the range of from about 0.060 to about 0.075 inches. The catheter 124 may be a steerable catheter with a deflectable distal tip, having a diameter within the range of from about 0.025 to about 0.050 inches. The guidewire 27 may have a diameter within the range of from about 0.014 to about 0.020 inches. In one example, the catheter 31 may have a diameter of about 0.088 inches, the catheter 120 about 0.071 inches, the catheter 124 about 0.035 inches, and the guidewire 27 may have a diameter of about 0.018 inches.

In one commercial execution, a preassembled access assembly (guide catheter, access catheter and guidewire) may be carried within a first channel on the sterile barrier tray and a preassembled procedure assembly (one or two procedure catheters and a guidewire) may be carried within the same or a different, second channel on the sterile barrier tray. One or two or more additional catheters or interventional tools may also be provided, depending upon potential needs during the interventional procedure.

Figures 3G, 3H, 3I, 3J, 3K, 3L, 3M:
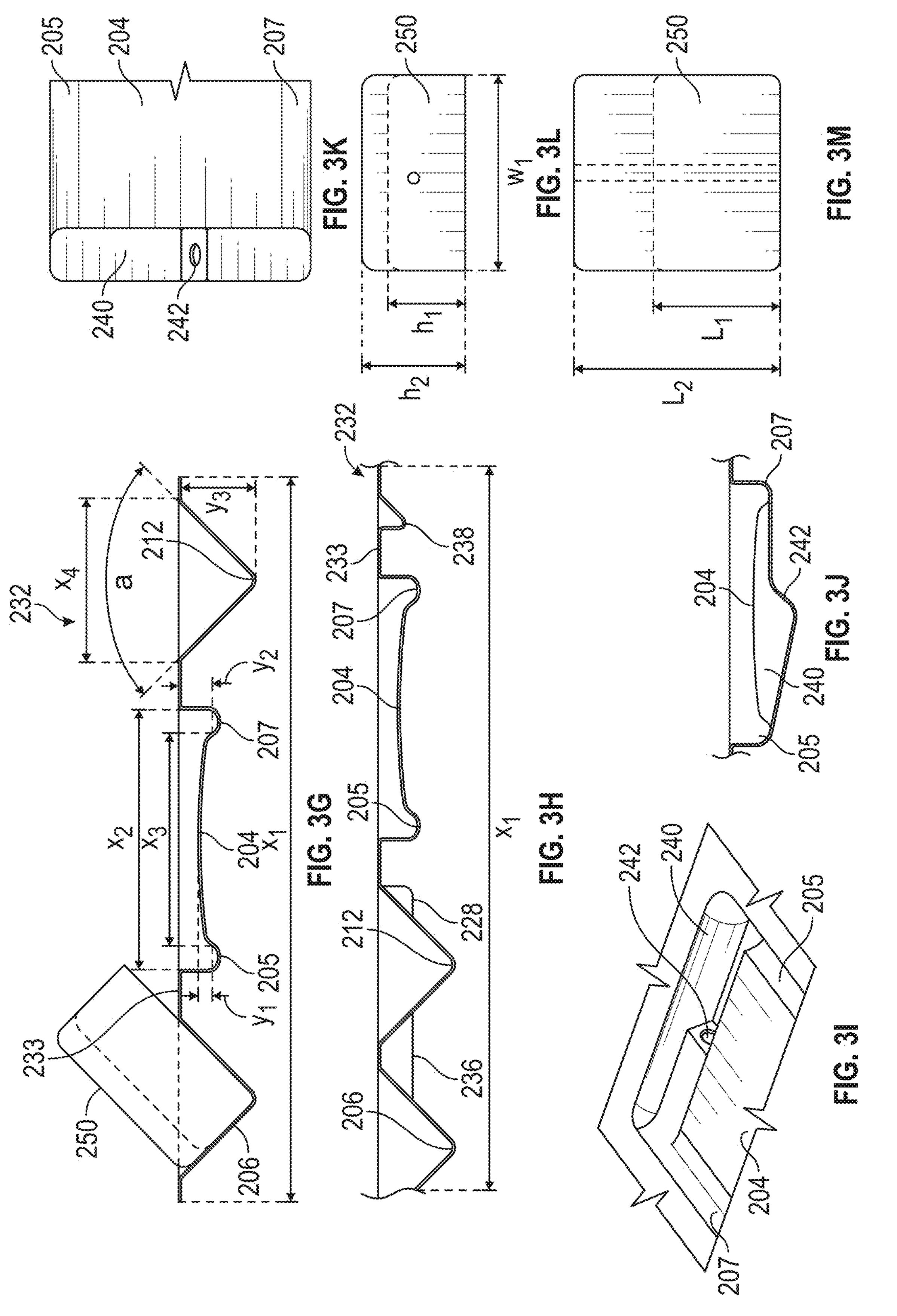
FIGS. 3G-3K show embodiments of an alternate sterile barrier having a convex drive surface.
FIGS. 3L and 3M depict an example of a hub that may be used with the sterile barriers of FIGS. 3G-3K.

FIGS. 3G-3K illustrate embodiments of an alternate sterile barrier having a convex drive surface (e.g., a convex, crowned road like drive surface). FIG. 3G is a cross-sectional view of a sterile barrier 232. The sterile barrier 232 includes a convex upper support surface 204. Fluid channels 205 and 207 are positioned laterally of and below the support surface 204 for self-clearing or draining of fluids from the support surface 204 (for example, during an interventional procedure). The fluid channels 205 and 207 may extend axially at least a portion of the length of the sterile barrier.

FIGS. 3I, 3J, and 3K illustrate a sectional perspective view, a cross-sectional view, and a top sectional view, respectively, of a proximal end of the sterile barrier 232. As shown, in FIGS. 3I-3K, the sterile barrier 232 can include a trough 240 in communication with the fluid channels 205 and 207. The trough 240 can receive fluids from the channels 205 and 207 (for example, during an interventional procedure). The trough 240 may be positioned at least partially below the fluid channels 205 and 207 so that fluid within the channels 205 and 207 flows into the trough 240. In certain embodiments, the fluid channels 205 and 207 may be angled relative to a horizontal plane (for example, may decline from an end of the channel furthest from the trough 240 to the trough 240) so that fluid within the channels 205 and 207 is directed to the trough 240. For example, the channels 205 and 207 may increase in depth from an end of the channels furthest from the trough 240 to the trough 240. Alternatively, the sterile barrier 232 and/or support table may be positioned at an angle relative to a horizontal plane, during part of or an entirety of an interventional procedure, such that the end of the channels 205 and 207 furthest from the trough 240 is positioned higher than the trough 240. For example, the sterile barrier 232 and/or support table may be constructed or arranged in an angled arrangement so that an end of the sterile barrier 232 and/or support table opposite the trough 240 is positioned higher than the trough 240. Alternatively or additionally, a drive mechanism may temporarily tilt the sterile barrier 232 and/or support table so that an end of the sterile barrier 232 and/or support table opposite the trough 240 is positioned higher than the trough 240 (for example, by lifting an end of the sterile barrier and/or support table opposite the trough 240 or lowering an end of the sterile barrier 232 and/or support table at which the trough 240 is positioned) so that fluids within the channels 205 and 207 flow into the trough 240.

The trough 240 can include a drain hole 242. The trough 240 can be shaped, dimensioned, and/or otherwise configured so that fluid within the trough 240 empties to the drain hole 242. The drain hole 242 can include tubing, a barb fitting, and/or an on-off valve for removal of fluids from the trough 240. As shown in FIGS. 3I-3K, the trough 240 can be positioned at the proximal end of the sterile barrier 232. In alternate embodiments, the trough 240 may be positioned at a distal end of the sterile barrier 232. In some embodiments, the sterile barrier 232 can include a first trough 240 at the proximal end and a second trough 240 at the distal end. In some embodiments, the trough 240 can also be used as a wash basin.

A first channel 206 may extend axially at least a portion of the length of the sterile barrier 232. The channel 206 can have a sufficient length to hold the interventional devices, and sufficient width and depth to hold the corresponding hubs (for example, by providing support to prevent dislodgement of the hubs when forces are applied to the hubs). Optionally, a second channel 212 may be provided. The second channel 212 may be located on the same side or the opposite side of the upper support surface 204 from the first channel 206. FIG. 3G illustrates the channel 212 located on the opposite side of the support surface 204 from the channel 206. FIG. 3H is a cross-sectional view illustrating an alternate embodiment of the sterile barrier 232 in which the channel 212 is on the same side of the support surface 204 as the channel 206.

As shown in FIGS. 3G and 3H, the channels 206 and 212 can have generally triangular, wedge-shaped, or otherwise angled cross-sections, so as to hold the hubs at an angle relative to a horizontal plane. Holding the hubs at an angle relative to the horizontal plane can allow for smaller width of the sterile barrier 232.

Two or three or more additional recesses such as additional channels or wells may be provided, to hold additional medical devices or supplies that may be useful during the interventional procedure as well as to collect fluids and function as wash basins for catheters and related devices.

In some embodiments, the sterile barrier 232 can include one or more structural ribs 236. The sterile barrier 232 can further include one or more frame support bosses 228 and 238.

In the embodiment of the sterile barrier 232 shown in FIG. 3G, a width $x_1$ can be 14 in, about 14 in, between 12 in and 16 in, between 10 in and 18 in, or any other suitable width. In the embodiment of the sterile barrier 232 shown in FIG. 3H, the width $x_1$ can be 15 in, about 15 in, between 13 in and 17 in, between 11 in and 19 in, or any other suitable width. A height $y_1$ of the support surface 204 can be 0.125 in, about 0.125 in, between 0.1 and 0.15 in, or any other suitable height. In some embodiments, the support surface 204 can be recessed from a top surface 233 of the sterile barrier 232. A height $y_2$ between a bottom of the support surface 204 and the top surface 233 can be 0.5 in, about 0.5 in, between 0.25 in and 0.75 in, or any other suitable height. A width $x_2$ from a lateral edge of the channel 205 to a lateral edge of the channel 207 can be 5 in, about 5 in, between 4 in and 6 in, or any other suitable width. A width $x_3$ of the support surface 204 can be 4 in, about 4 in, between 3 in and 5 in, or any other suitable width. A height $y_3$ of the channel 206 and/or channel 212 can be 1.5 in, about 1.5 in, between 1 in and 2 in, or any other suitable height. A width $x_4$ of the channel 206 and/or channel 212 can be 3 in, about 3 in, between 2 in and 4 in, or any other suitable width. The channel 206 and/or channel 212 can be defined by an arc angle $\alpha$ of 90°, about 90°, between 80° and 100°, or any other suitable angle, and a radius of curvature of 0.125 in, about 0.125 in, between 0.1 and 0.15 in, or any other suitable radius of curvature. In certain embodiments, an arc angle $\alpha$ of 90° or about 90° may be used to hold a hub having a rectangular or generally rectangular cross-section. The support surface 204 can be defined by a radius of curvature of 13 in, about 13 in, between 11 in and 15 in, or any other suitable radius of curvature. The channel 205 and/or channel 207 can be defined by a radius of curvature of 0.25 in, about 0.25 in, between 0.15 in and 0.35 in, or any other suitable radius of curvature.

FIGS. 3L and 3M depict example dimensions of a hub 250 that may be used with the sterile barrier 232 as shown in FIGS. 3G-3K. The hub 250 may be any of the hubs described herein. In certain embodiments, the hub 250 can have a width $w_1$ of 3.75 in, about 3.75 in, between 3.25 in and 4.25 in, or any other suitable width. The hub 250 can have a height h1 of 1.5 in, about 1.5 in, between 1.25 in and 1.75 in, or any other suitable height. Alternatively, the hub 250 can have a height $h_2$ of 2 in, about 2 in, between 1.75 in and 2.25 in, or any other suitable height. In some embodiments, the hub 250 can have a length $L_1$ of 2.5 in, about 2.5 in, between 2 in and 3 in or any other suitable length. Alternatively, the hub 250 can have a length $L_2$ of 4 in, about 4 in, between 3.25 in and 4.75 in, or any other suitable length.

In some embodiments, a top surface of the support table can include surface features that generally correspond to those of the sterile barrier 232. For example, the support table can include a convex surface configured to correspond to the shape, size, and location of the support surface 204 and/or one or more recesses configured to correspond to the shape, size, and location of the channels 205 and 207.

In alternate embodiments, a planar support surface (for example, support surface 104 of sterile barrier 32) can be positioned at an angle to a horizontal plane to facilitate the draining of fluids. In some embodiments, the sterile barrier and/or support table may be positioned, during part of or the entirety of an interventional procedure, at an angle to a horizontal plane to facilitate the draining of fluids. For example, the sterile barrier and/or support table may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or additionally, a drive mechanism may temporarily tilt the sterile barrier and/or support table (for example, so that one lateral side of the planar support surface is positioned higher than the other lateral side of the planar support surface, the proximal end is higher than the distal end, or the distal end is higher than the proximal end) to facilitate the drainage of fluids. For example, the drive mechanism may raise or lower one lateral side of the sterile barrier and/or support table, the proximal end of the sterile barrier and/or support table, and/or the distal end of the sterile barrier and/or support table.

In certain embodiments, a support surface (for example, support surface 104 of sterile barrier 32) can be positioned in a vertical configuration instead in the horizontal configuration shown, for example, in FIGS. 3A-3F. For example, the support surface 104 can be positioned at about 90 degrees (or any other suitable angle) from a horizontal plane (e.g., rotated 90 degrees about a long axis of the support surface 104 relative to the embodiment shown in of FIGS. 3A-3F). A vertical configuration may provide for easier interaction with the drive system 18 by a physician. A vertical configuration may also provide for a lower axis of catheter travel closer to a patient without adding standoff height to the drive system 18.

In some embodiments, the drive system 18 may be positioned, during part of or the entirety of an interventional procedure, at an angle to a horizontal plane to facilitate the draining of fluids. For example, the drive system 18 may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or additionally, a drive mechanism may temporarily tilt the drive system 18 (for example, so that one lateral side of the drive system 18 is positioned higher than the other lateral side of the drive system 18, the proximal end is higher than the distal end, or the distal end is higher than the proximal end) to facilitate the drainage of fluids. For example, the drive mechanism may raise or lower one lateral side of the system 18, the proximal end of the drive system 18, and/or the distal end of the drive system 18. In some embodiments, the drive system 18 may be angled so that it extends at an angle away from axis point 24 (for example, so that the proximal end is higher than the distal end), for example, to allow for clearance of a patient's feet.

Figure 4:
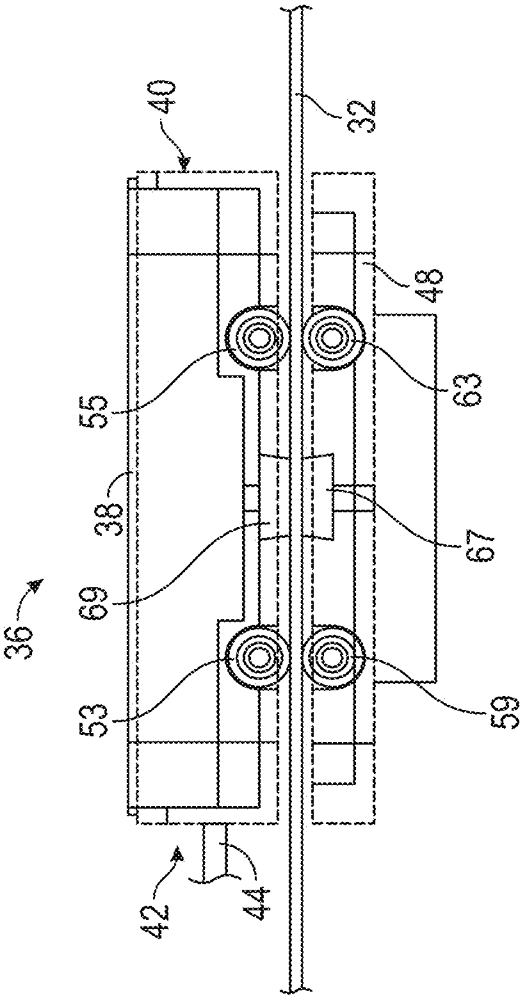
FIG. 4 is a schematic elevational cross section through a hub adapter having a drive magnet separated from an interventional device hub and driven magnet by a sterile barrier.

Referring to FIG. 4, hub 36 may represent any of the hubs previously described. Hub 36 includes a housing 38 which extends between a proximal end 40 and a distal end 42. An interventional device 44, which could be any of the interventional devices disclosed herein, extends distally from the hub 36 and into the patient 14 (not illustrated). A hub adapter 48 or carriage acts as a shuttle by advancing proximally or distally along a track in response to operator instructions or controller manipulations. The hub adapter 48 includes at least one drive magnet 67 configured to couple with a driven magnet 69 carried by the hub 36. This provides a magnetic coupling between the drive magnet 67 and driven magnet 69 through the sterile barrier such that the hub 36 is moved across the top of the sterile barrier 32 in response to movement of the hub adapter 48 outside of the sterile field. Movement of the hub adapter is driven by a drive system carried by the support table and described in additional detail below. The hub adapter may act as a robotic drive for an interventional device coupled thereto.

To reduce friction in the system, the hub 36 may be provided with at least a first roller 53 and a second roller 55 which may be in the form of wheels or rotatable balls or drums. The rollers space the sterile barrier apart from the surface of the driven magnet 69 by at least about 0.02 centimeters (about 0.008 inches) and generally no more than about 0.08 centimeters (about 0.03 inches). In some implementations, the space is within the range of from about 0.03 centimeters (about 0.010 inches) and about 0.041 centimeters (about 0.016 inches). The space between the drive magnet 67 and driven magnet 69 is generally no more than about 0.38 centimeters (about 0.15 inches) and in some implementations is no more than about 0.254 centimeters (about 0.10 inches) such as within the range of from about 0.216 centimeters (about 0.085 inches) to about 0.229 centimeters (about 0.090 inches). The hub adapter 48 may similarly be provided with at least a first hub adapter roller 59 and the second hub adapter roller 63, which may be positioned opposite the respective first roller 53 and second roller 55 as illustrated in FIG. 4.

Figure 6:
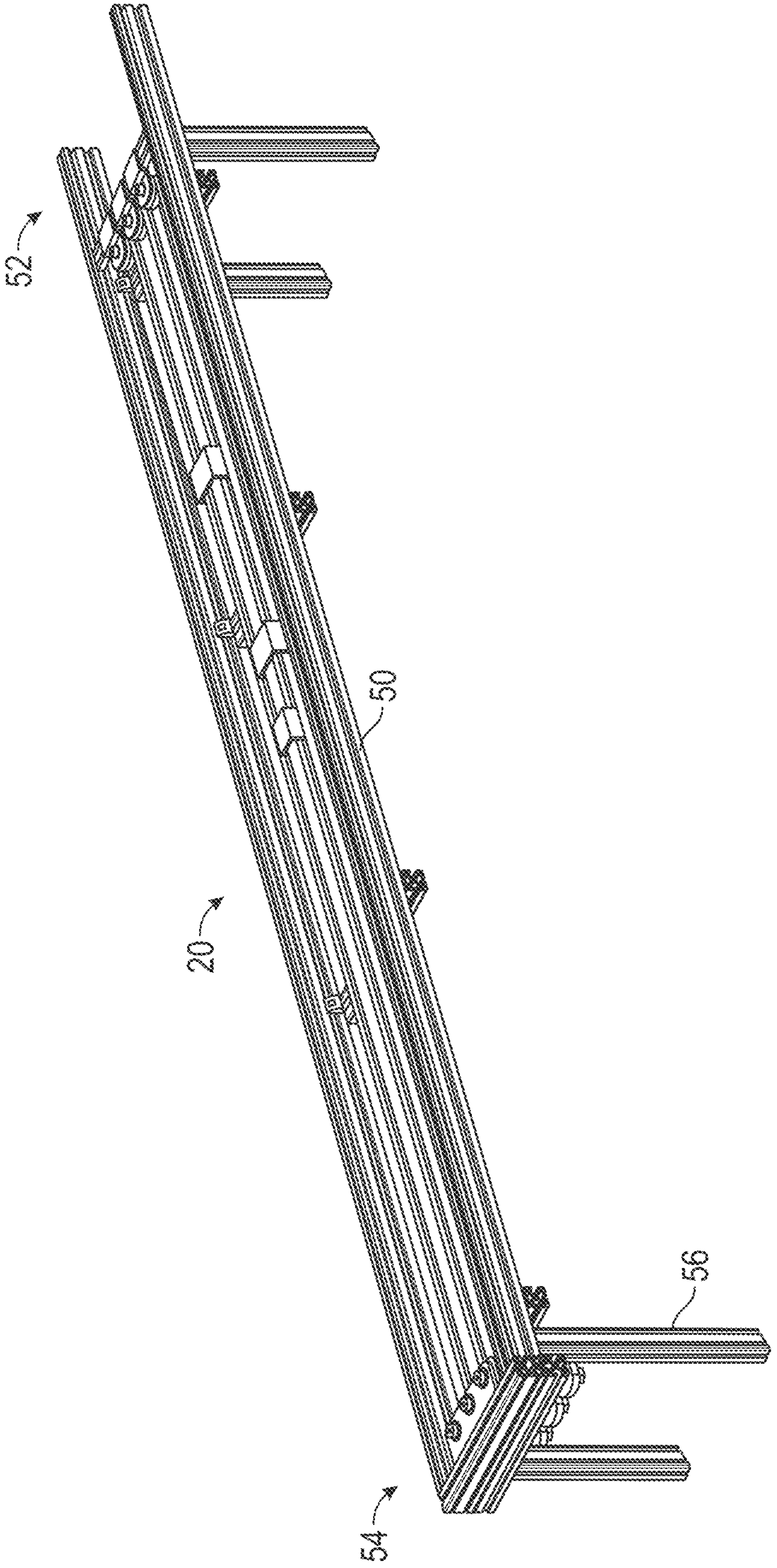
FIG. 6 is a perspective view of a support table.

Referring to FIG. 6, there is schematically illustrated one example of a low-profile linear drive support table 20. Support table 20 comprises an elongated frame 51 extending between a proximal end 52 and a distal end 54. At least one support table support 56 is provided to stabilize the support table 20 with respect to the patient (not illustrated). Support 56 may comprise one or more legs or preferably an articulating arm configured to allow movement and positioning of the frame 51 over or adjacent to the patient.

Figure 7:
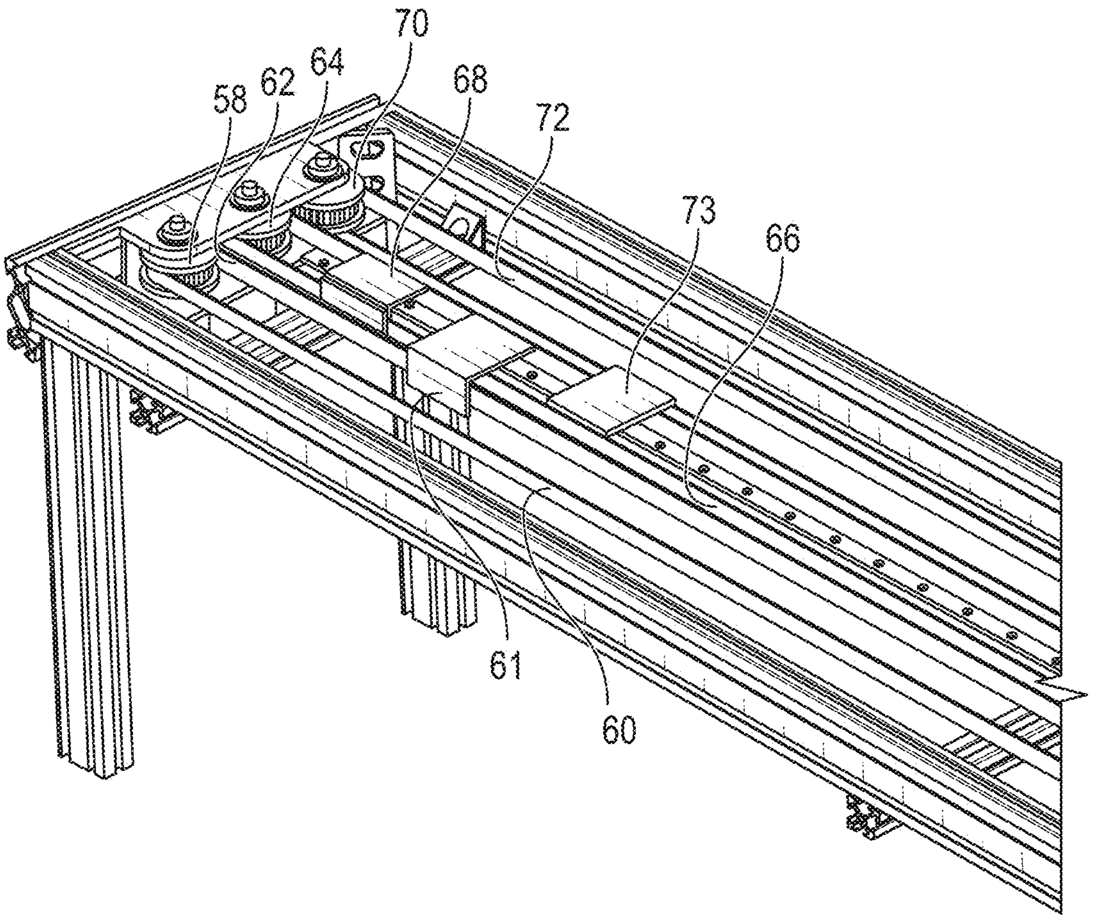
FIG. 7 is a close-up view of the motor drive end of a support table.

One example of a linear drive table 20 illustrated in FIG. 7 includes three distinct drives. However, two drives or four or more drives (e.g., up to eight drives) may be included depending upon the desired clinical performance. A first drive pulley 58 engages a first drive belt 60. A first carriage bracket 61 is secured to the first drive belt 60 such that rotation of the first drive pulley 58 causes rotation of the first drive belt 60 through an elongate closed loop path. The first carriage bracket 61 may be advanced in a proximal or distal direction along the longitudinal axis of the support table 20 depending upon the direction of rotation of the drive pully 58. In the illustrated implementation, the drive pulley 58 is provided with surface structures such as a plurality of drive pulley teeth 62 for engaging complementary teeth on the first drive belt 60.

A second drive pulley 64 may engage a second drive belt 66 configured to axially move a second carriage bracket 68 along an axial path on the support table 20. A third drive pulley 70 may be configured to drive a third drive belt 72, to advance a third carriage bracket 73 axially along the support table 20. Each of the carriage brackets may be provided with a drive magnet assembly discussed previously but not illustrated in FIG. 7, to form couplers for magnetically coupling to a corresponding driven magnet within the hub of an interventional device as has been discussed.

Figure 8:
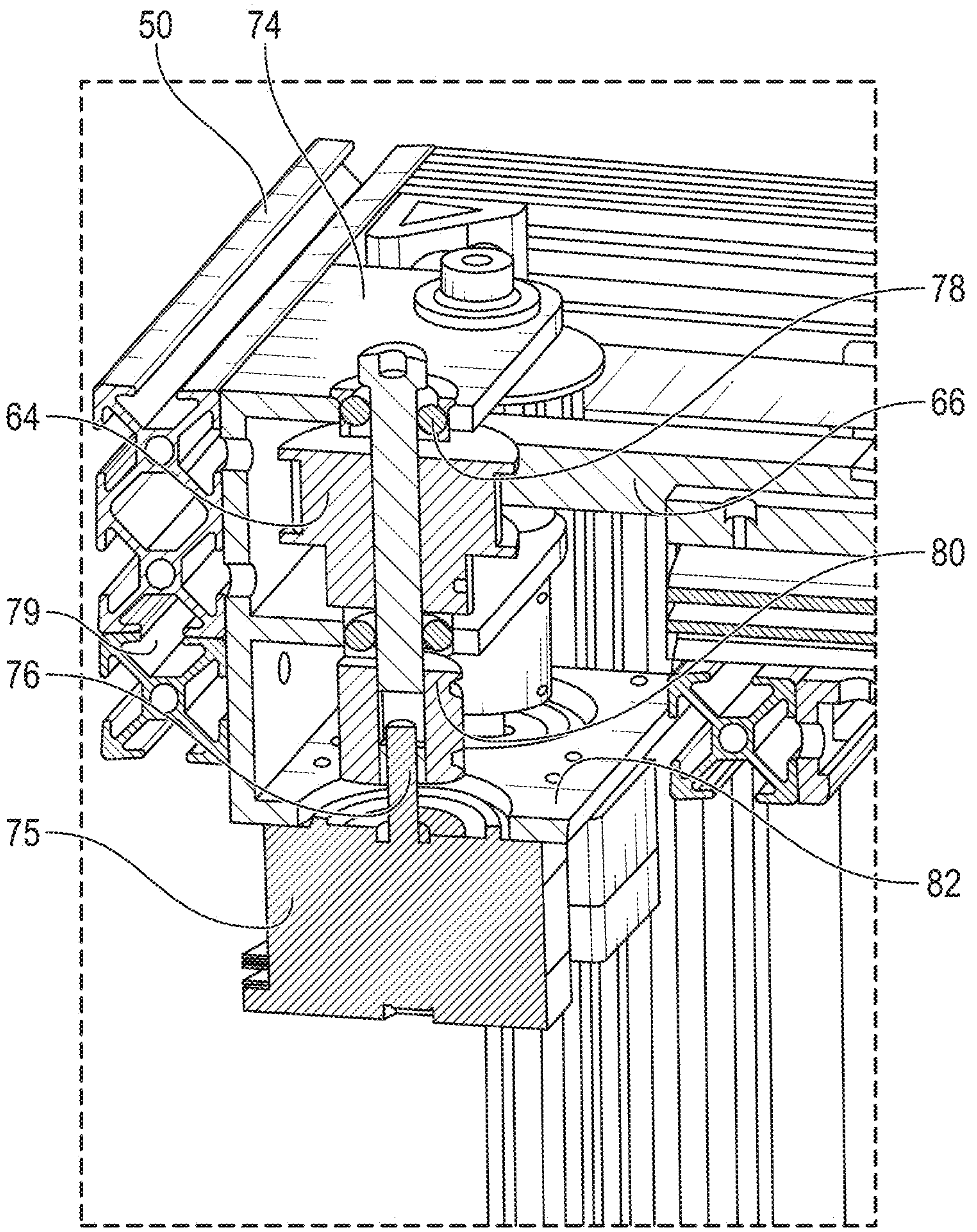
FIG. 8 is an elevational cross section through a motor and belt drive assembly.

A detailed view of a drive system is shown schematically in FIG. 8. A drive support 74 may be carried by the frame 51 for supporting the drive assembly. The second drive pulley 64 is shown in elevational cross section as rotationally driven by a motor 75 via a rotatable shaft 76. The rotatable shaft 76 may be rotatably carried by the support 74 via a first bearing 78, a shaft coupling 80 and second bearing 79. Motor 75 may be stabilized by a motor bracket 82 connected to the drive support 74 and or the frame 51. The belt drive assemblies for the first drive belt 60 and third drive belt 72 maybe similarly constructed and are not further detailed herein. In some embodiments, the drive systems described herein may be a rack and pinion drive table system that is foldable. In such embodiments, motors 75 may be attached to and move with the carriages.

Figure 9:
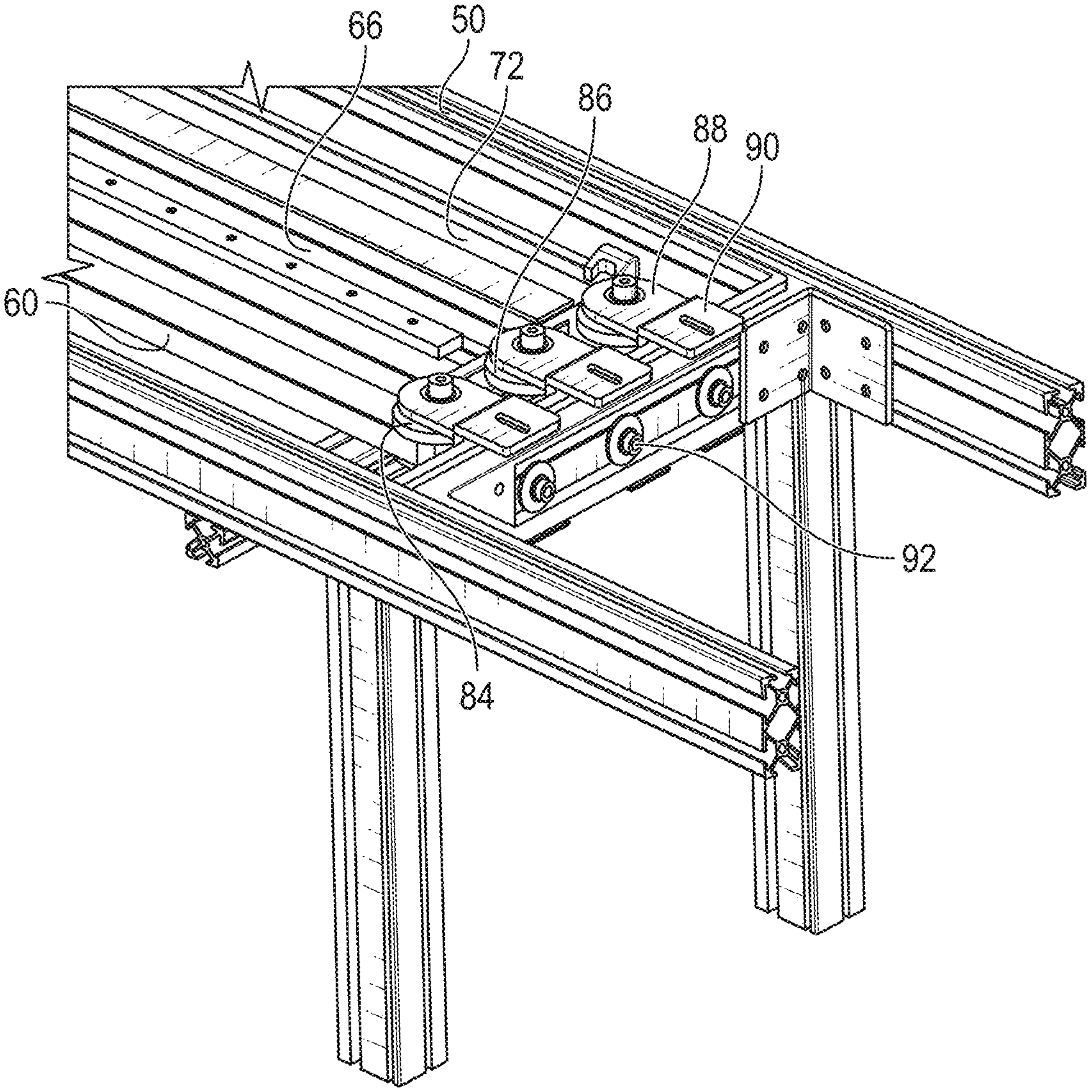
FIG. 9 is a close-up view of a pulley end of the support table.
Figure 10:
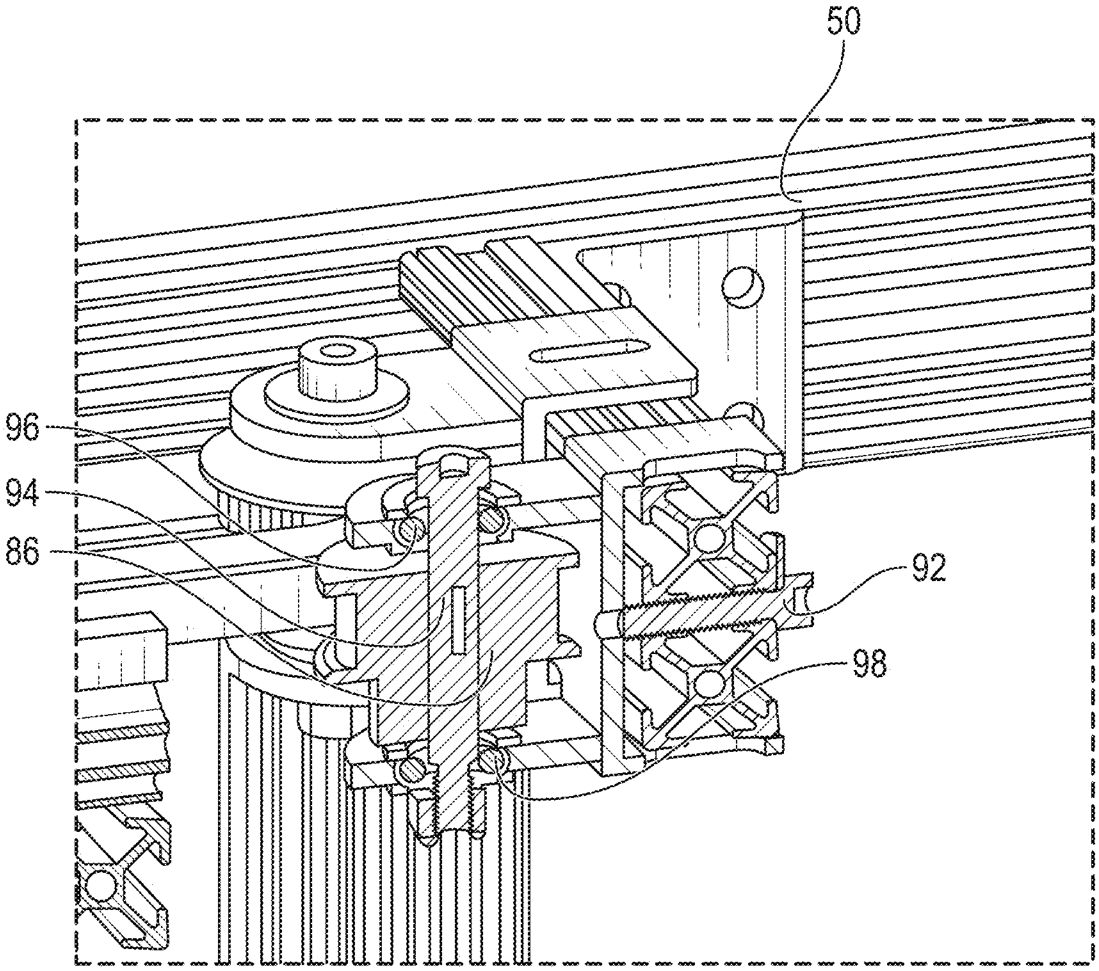
FIG. 10 is an elevational cross section through a belt pully.

Referring to FIGS. 9 and 10, each of the first second and third drive belts extends around a corresponding first idler pulley 84 second idler pulley 86 and third idler pulley 88. Each idler pulley may be provided with a corresponding tensioning bracket 90, configured to adjust the idler pulleys in a proximal or distal direction in order to adjust the tension of the respective belt. Each tensioning bracket 90 is therefore provided with a tensioning adjustment 92 such as a rotatable screw.

As seen in FIG. 10, the second idler pulley 86, for example, may be carried by a rotatable shaft 94, rotatably secured with respect to the mounting bracket by a first bearing 96 and second bearing 98.

Figure 5A:
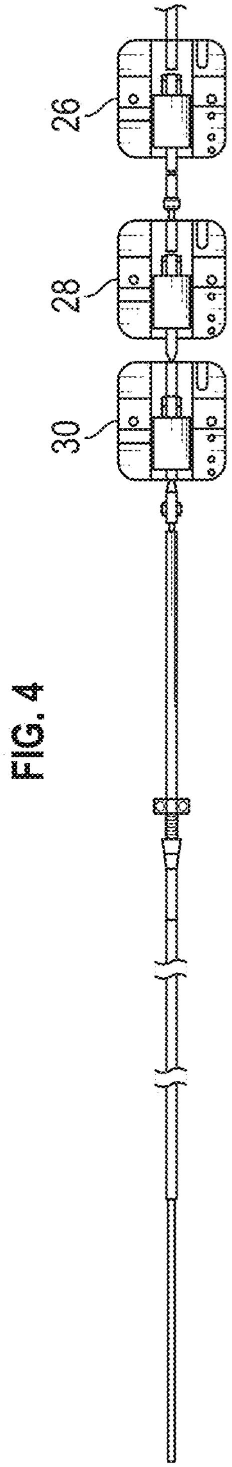
FIGS. 5A and 5B schematically illustrate a three interventional device and a four interventional device assembly.
Figure 5B:
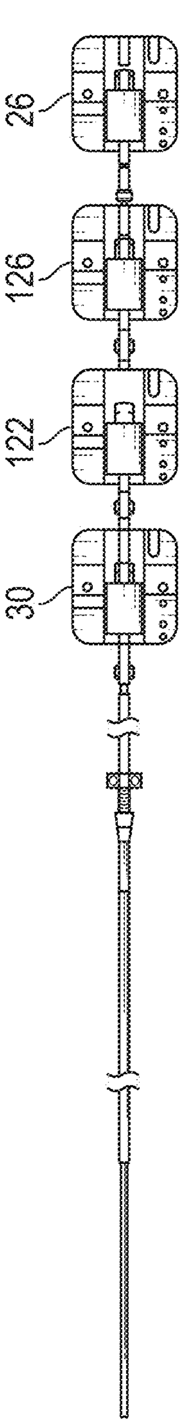
Figure 11:
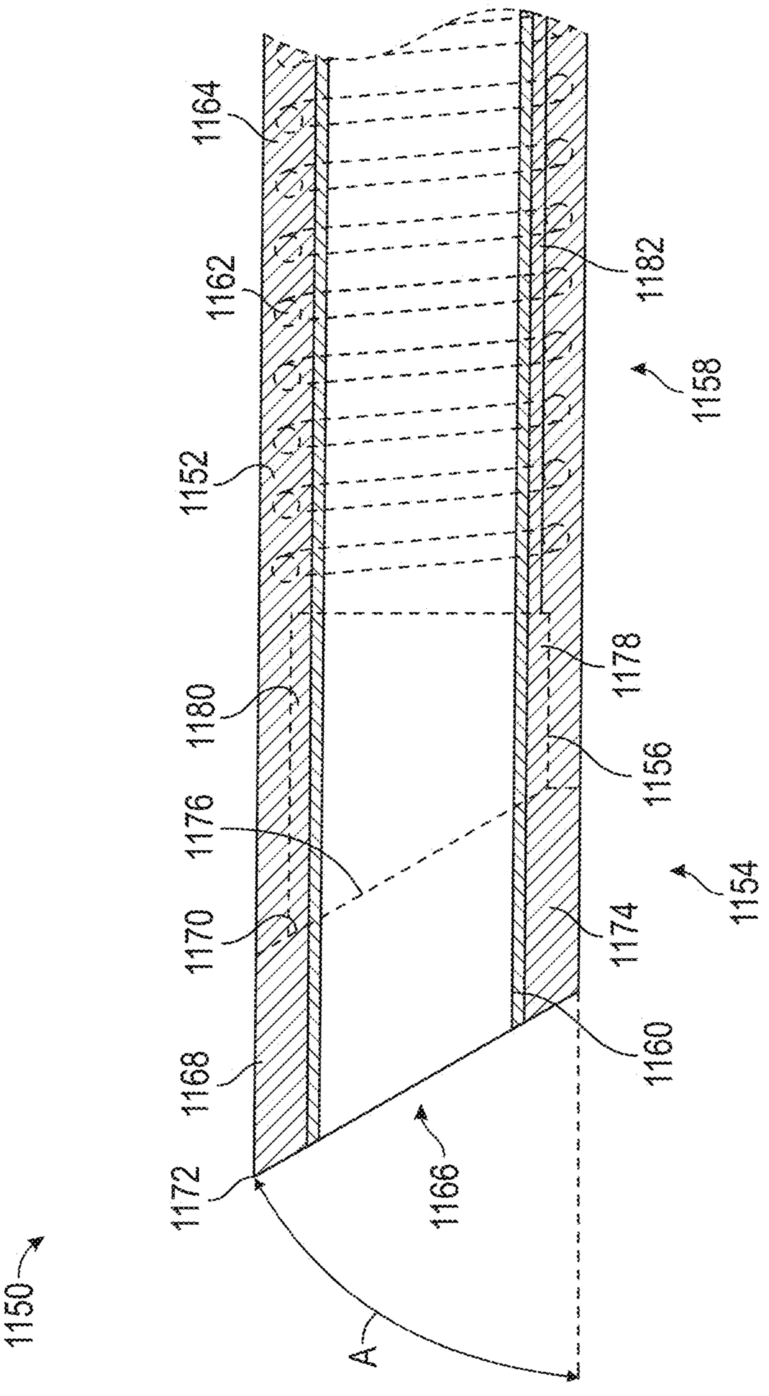
FIG. 11 is a side elevational cross-section through a distal portion of a catheter such as any of those shown in FIGS. 5A and 5B.

Any of the catheters illustrated, for example, in FIG. 5A, 5B or 11 generally comprise an elongate tubular body extending between a proximal end and a distal functional end. The length and diameter of the tubular body depends upon the desired application. For example, lengths in the area of from about 90 centimeters to about 195 centimeters or more are typical for use in femoral access percutaneous transluminal coronary applications. Intracranial or other applications may call for a different catheter shaft length depending upon the vascular access site.

Any of the catheters disclosed herein may be provided with an inclined distal tip. Referring to FIG. 11, distal catheter tip 1150 comprises a tubular body 1152 which includes an advance segment 1154, a marker band 1156 and a proximal segment 1158. An inner tubular liner 1160 may extend throughout the length of the distal catheter tip 1150, and may comprise dip coated or extruded PTFE or other lubricious material.

A reinforcing element 1162 such as a braid and/or spring coil is embedded in an outer jacket 1164 which may extend the entire length of the catheter.

The advance segment 1154 terminates distally in an angled face 1166, to provide a leading side wall portion 1168 having a length measured between the distal end 130 of the marker band 1156 and a distal tip 1172. In some embodiments, the entire distal tip may be shaped to avoid snagging the tip in areas of arterial bifurcation. A trailing side wall portion 1174 of the advance segment 1154, has an axial length in the illustrated embodiment of approximately equal to the axial length of the leading side wall portion 1168 as measured at approximately 180 degrees around the catheter from the leading side wall portion 1168. The leading side wall portion 1168 may have an axial length within the range of from about 0.1 millimeters to about 5 millimeters and generally within the range of from about 1 to 3 millimeters. The trailing side wall portion 1174 may be equal to or at least about 0.1 or 0.5 or 1 millimeter or 2 millimeters or more shorter than the axial length of the leading side wall portion 1168, depending upon the desired performance.

The angled face 1166 inclines at an angle A within the range of from about 45 degrees to about 80 degrees from the longitudinal axis of the catheter. For certain implementations, the angle is within the range of from about 55 degrees to about 65 degrees from the longitudinal axis of the catheter. In one implementation, the angle A is about 60 degrees. One consequence of an angle A of less than 90 degrees is an elongation of a major axis of the area of the distal port which increases the surface area of the port and may enhance clot aspiration or retention. Compared to the surface area of the circular port (angle A is 90 degrees), the area of the angled port is generally at least about 105 percent, and no more than about 130 percent, in some implementations within the range of from about 110 percent and about 125 percent, and in one example is about 115 percent of the area of the corresponding circular port (angle A is 90 degrees).

In the illustrated embodiment, the axial length of the advance segment is substantially constant around the circumference of the catheter, so that the angled face 1166 is approximately parallel to the distal surface 1176 of the marker band 1156. The marker band 1156 has a proximal surface approximately transverse to the longitudinal axis of the catheter, producing a marker band 1156 having a right trapezoid configuration inside elevational view. A short sidewall 1178 is rotationally aligned with the trailing side wall portion 1174, and has an axial length within the range of from about 0.2 millimeters to about 4 millimeters, and typically from about 0.5 millimeters to about 2 millimeters. An opposing long sidewall 1180 is rotationally aligned with the leading side wall portion 1168. Long sidewall 1180 of the marker band 1156 is generally at least about 10 percent or 20 percent longer than short sidewall 1178 and may be at least about 50 percent or 70 percent or 90 percent or more longer than short sidewall 1178, depending upon desired performance. Generally, the long sidewall 1180 will have a length of at least about 0.5 millimeters or 1 millimeter and less than about 5 millimeters or 4 millimeters.

The marker band may be a continuous annular structure, or may have at least one and optionally two or three or more axially extending slits throughout its length. The slit may be located on the short sidewall 1178 or the long sidewall 1180 or in between, depending upon desired bending characteristics. The marker band may comprise any of a variety of radiopaque materials, such as a platinum/iridium alloy, with a wall thickness preferably no more than about 0.003 inches and in one implementation is about 0.001 inches.

The fluoroscopic appearance of the marker bands may be unique or distinct for each catheter size or type when a plurality of catheters is utilized so that the marker bands can be distinguishable from one another by a software algorithm. Distinguishing the marker bands of a plurality of catheters may be advantageous when the multiple catheters are used together, for example, in a multi catheter assembly or stack as described herein. In some embodiments, the marker band of a catheter may be configured so that a software algorithm can detect motion of the catheter tip.

The marker band zone of the assembled catheter may have a relatively high bending stiffness and high crush strength, such as at least about 50 percent or at least about 100 percent less than proximal segment 18 but generally no more than about 200 percent less than proximal segment 1158. The high crush strength may provide radial support to the adjacent advance segment 1154 and particularly to the leading side wall portion 1168, to facilitate the functioning of distal tip 1172 as an atraumatic bumper during transluminal advance and to resist collapse under vacuum. The proximal segment 1158 preferably has a lower bending stiffness than the marker band zone, and the advance segment 1154 preferably has even a lower bending stiffness and crush strength than the proximal segment 1158.

The advance segment 1154 may comprise a distal extension of the outer tubular jacket 1164 and optionally the inner liner 1160, without other internal supporting structures distally of the marker band 1156. Outer jacket 1164 may comprise extruded polyurethane, such as Tecothane®. The advance segment 1154 may have a bending stiffness and radial crush stiffness that is no more than about 50 percent, and in some implementations no more than about 25 percent or 15 percent or 5 percent or less than the corresponding value for the proximal segment 1158.

The catheter may further comprise an axial tension element or support such as a ribbon or one or more filaments or fibers for increasing the tension resistance and/or influencing the bending characteristics in the distal zone. The tension support may comprise one or more axially extending mono strand or multi strand filaments. The one or more tension element 1182 may be axially placed inside the catheter wall near the distal end of the catheter. The one or more tension element 1182 may serve as a tension support and resist tip detachment or elongation of the catheter wall under tension (e.g., when the catheter is being proximally retracted through a kinked outer catheter or tortuous or narrowed vasculature).

At least one of the one or more tension element 1182 may proximally extend along the length of the catheter wall from within about 1.0 centimeters from the distal end of the catheter to less than about 10 centimeters from the distal end of the catheter, less than about 20 centimeters from the distal end of the catheter, less than about 30 centimeters from the distal end of the catheter, less than about 40 centimeters from the distal end of the catheter, or less than about 50 centimeters from the distal end of the catheter.

The one or more tension element 1182 may have a length greater than or equal to about 40 centimeters, greater than or equal to about 30 centimeters, greater than or equal to about 20 centimeters, greater than or equal to about 10 centimeters, or greater than or equal to about 5 centimeters.

At least one of the one or more tension element 1182 may extend at least about the most distal 50 centimeters of the length of the catheter, at least about the most distal 40 centimeters of the length of the catheter, at least about the most distal 30 centimeters or 20 centimeters or 10 centimeters of the length of the catheter.

In some implementations, the tension element extends proximally from the distal end of the catheter along the length of the coil 24 and ends proximally within about 5 centimeters or 2 centimeters or less either side of a transition between a distal coil and a proximal braid. The tension element may end at the transition without overlapping with the braid.

The one or more tension element 1182 may be placed near or radially outside the inner liner 1160. The one or more tension element 1182 may be placed near or radially inside the braid and/or the coil. The one or more tension element 1182 may be carried between the inner liner 1160 and the helical coil, and may be secured to the inner liner or other underlying surface by an adhesive prior to addition of the next outer adjacent layer such as the coil. Preferably, the tension element 1182 is secured to the marker band 1156 such as by adhesives or by mechanical interference. In one implementation, the tension element 1182 extends distally beyond the marker band on a first (e.g., inside) surface of the marker band, then wraps around the distal end of the marker band and extends along a second (e.g., outside) surface in either or both a proximal inclined or circumferential direction to wrap completely around the marker band.

When more than one tension element 1182 or filament bundles are spaced circumferentially apart in the catheter wall, the tension elements 1182 may be placed in a radially symmetrical manner. For example, the angle between two tension elements 1182 with respect to the radial center of the catheter may be about 180 degrees. Alternatively, depending on desired clinical performances (e.g., flexibility, trackability), the tension elements 1182 may be placed in a radially asymmetrical manner. The angle between any two tension elements 1182 with respect to the radial center of the catheter may be less than about 180 degrees, less than or equal to about 165 degrees, less than or equal to about 135 degrees, less than or equal to about 120 degrees, less than or equal to about 90 degrees, less than or equal to about 45 degrees or, less than or equal to about 15 degrees.

The one or more tension element 1182 may comprise materials such as Vectran®, Kevlar®, Polyester®, Spectra®, Dyneema®, Meta-Para-Aramide®, or any combinations thereof. At least one of the one or more tension element 1182 may comprise a single fiber or a multi-fiber bundle, and the fiber or bundle may have a round or rectangular (e.g., ribbon) cross section. The terms fiber or filament do not convey composition, and they may comprise any of a variety of high tensile strength polymers, metals or alloys depending upon design considerations such as the desired tensile failure limit and wall thickness. The cross-sectional dimension of the one or more tension element 1182, as measured in the radial direction, may be no more than about 2 percent, 5 percent, 8 percent, 15 percent, or 20 percent of that of the catheter 10.

The cross-sectional dimension of the one or more tension element 1182, as measured in the radial direction, may be no more than about 0.03 millimeters (about 0.001 inches), no more than about 0.0508 millimeters (about 0.002 inches), no more than about 0.1 millimeters (about 0.004 inches), no more than about 0.15 millimeters (about 0.006 inches), no more than about 0.2 millimeters (about 0.008 inches), or about 0.38 millimeters (about 0.015 inches).

The one or more tension element 1182 may increase the tensile strength of the distal zone of the catheter before failure under tension (e.g., marker band detachment) to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 12A:
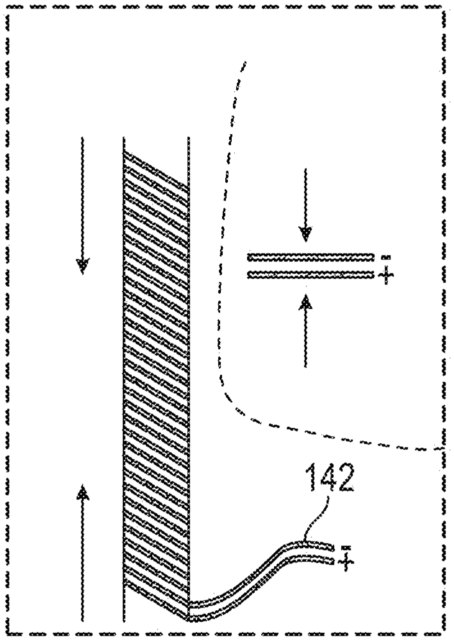
FIGS. 12A and 12B schematically illustrate a force sensor integrated into the sidewall of the catheter.

Any of a variety of sensors may be provided on any of the catheters, hubs, carriages, or table, depending upon the desired data. For example, in some implementations, it may be desirable to measure axial tension or compression force applied to the catheter such as along a force sensing zone. The distal end of the catheter would be built with a similar construction as illustrated in FIG. 11, with a helical coil distal section. But instead of using a single helical coil of nitinol wire, a first conductor 140 and second conductor 142 are wrapped into intertwined helical coils and electrically isolated from each other such as by the plastic/resin of the tubular body. See FIG. 12A. Each coil is in electrical communication with the proximal hub by a unique electrical conductor such as a conductive trace or proximal extension of the wire.

Figure 12B:
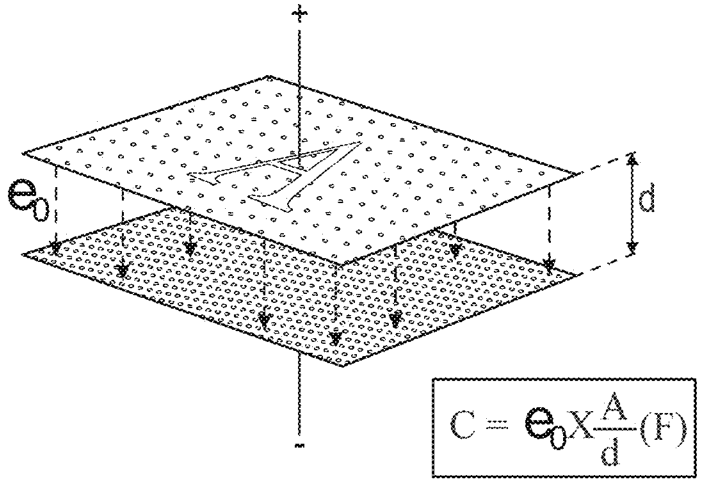

This construction of double, electrically isolated helical coils creates a capacitor. This is roughly equivalent to two plates of nitinol with a plastic layer between them, illustrated in FIG. 12B. The capacitance is inversely proportional to the distance between wires. The only variable that would be changing would be d, the distance between the plates. If an axial compressive force is applied to the catheter, the wires (e.g., conductor 140 and conductor 142) will move closer together, thus increasing the capacitance. If an axial tensile force is applied, the wires will get further apart, decreasing the capacitance. This capacitance can be measured at the proximal end of the catheter, giving a measurement of the force at the helical capacitor. Although referred to as a capacitor, this sensor is measuring the electrical interaction between the two coils of wire. There may be a measurable change in inductance or other resulting change due to applied axial forces.

At least a first helical capacitor may have at least one or five or ten or more complete revolutions of each wire. A capacitor may be located within the distal most 5 or 10 or 20 centimeters of the catheter body to sense forces experienced at the distal end. At least a second capacitor may be provided within the proximal most 5 or 10 or 20 centimeters of the catheter body, to sense forces experienced at the proximal end of the catheter.

Figure 13A:
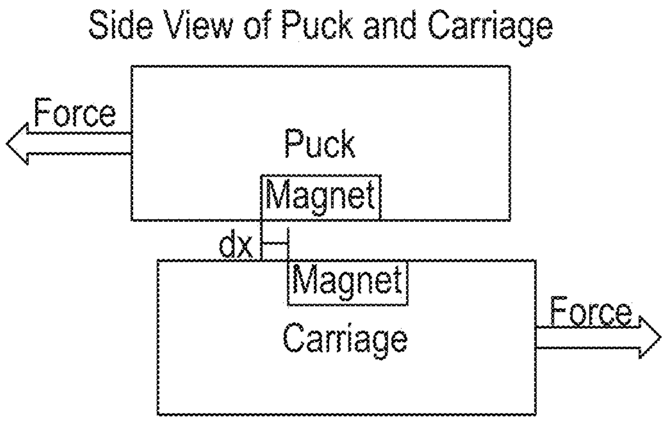
FIGS. 13A and 13B schematically illustrate a sensor for measuring elastic forces at the magnetic coupling between the hub and corresponding carriage.
Figure 13B:
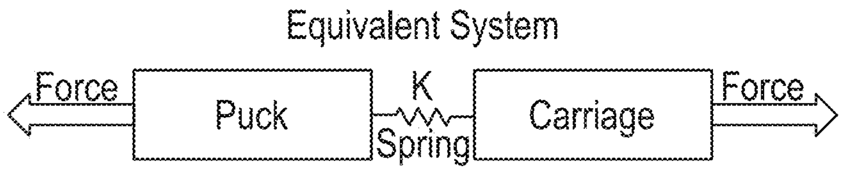

It may also be desirable to measure elastic forces across the magnetic coupling between the hub and corresponding carriage, using the natural springiness (compliance) of the magnetic coupling to measure the force applied to the hub. The magnetic coupling between the hubs and carriages creates a spring. When a force is applied to the hub, the hub will move a small amount relative to the carriage. See FIG. 13A. In robotics, this is called a series elastic actuator. This property can be used to measure the force applied from the carriage to the hub. To measure the force, the relative distance between the hub and the carriage (dx shown in FIG. 13A) is determined and characterize some effective spring constant k between the two components. See FIG. 13B.

The relative distance could be measured in multiple different ways. One method for measuring the relative distance between the hub and carriage is a magnetic sensor (e.g., a Hall effect Sensor between hub and carriage). A magnet is mounted to either the hub or carriage, and a corresponding magnetic sensor is mounted on the other device (carriage or hub). The magnetic sensor might be a hall effect sensor, a magnetoresistive sensor, or another type of magnetic field sensor. Generally, multiple sensors may be used to increase the reliability of the measurement. This reduces noise and reduces interference from external magnetic fields.

Other non-contact distance sensors can also be used. These include optical sensors, inductance sensors, and capacitance sensors. Optical sensors would preferably be configured in a manner that avoids accumulation of blood or other fluid in the interface between the hubs and carriages. In some implementations, wireless (i.e., inductive) power may be used to translate movement and/or transfer information across the sterile barrier between a drive carriage and a hub, for example.

The magnetic coupling between the hub and the carriage has a shear or axial break away threshold which may be about 300 grams or 1000 grams or more. The processor can be configured to compare the axial force applied to the catheter to a preset axial trigger force which if applied to the catheter is perceived to create a risk to the patient. If the trigger force is reached, the processor may be configured to generate a response such as a visual, auditory or tactile feedback to the physician, and/or intervene and shut down further advance of the catheter until a reset is accomplished.

An override feature may be provided so the physician can elect to continue to advance the catheter at forces higher than the trigger force, in a situation where the physician believes the incremental force is warranted.

In some embodiments, active real-time or near real-time force sensing can be used for each interventional device (or a subset of interventional devices) to detect energy storage in compression, tension, and/or rotational shear which can be generated by friction between the interventional devices. The energy storage may be relieved by a user (e.g., using a push/pull technique on one or more of the interventional devices) to reduce the risk of inadvertent uncommanded motion due to energy release. In some embodiments, force sensing data can be used by the systems described herein to detect energy storage and provide a warning to user (for example, if the amount of energy stored exceeds a threshold value). In some embodiments, the drive system may automatically adjust the interventional devices (for example, via axial movement of interventional devices in which an amount of stored energy exceeds a threshold value) to relieve the energy storage.

Force and or torque sensing fiber optics (e.g., Fiber Bragg Grating (FBG) sensors) may be built into the catheter side wall to measure the force and/or torque at various locations along the shaft of a catheter or alternatively may be integrated into a guidewire. The fiber measures axial strain, which can be converted into axial force or torque (when wound helically). At least a first FBG sensor can be integrated into a distal sensing zone, proximal sensing zone and/or intermediate sensing zone on the catheter or guidewire, to measure force and or torque in the vicinity of the sensor.

It may also be desirable to understand the three-dimensional configuration of the catheter or guidewire during and/or following transvascular placement. Shape sensing fiber optics such as an array of FBG fibers to sense the shape of catheters and guidewires. By using multiple force sensing fibers that are a known distance from each other, the shape along the length of the catheter/guidewire can be determined. In some embodiments, the shape along the length of the catheter/guidewire can be determined using RSIP fluoroscopy image processing.

A resistive strain gauge may be integrated into the body of the catheter or guidewire to measure force or torque. Such as at the distal tip and/or proximal end of the device.

Measurements of force and/or torque applied to the catheter or guidewire shafts can be used to determine applied force and/or torque above a safety threshold. When an applied force and/or torque exceeds a safety threshold, a warning may be provided to a user. Applied force and/or torque measurements may also be used to provide feedback related to better catheter manipulation and control. Applied force and/or torque measurements may also be used with processed fluoroscopic imaging information to determine or characterize distal tip motion.

Absolute position of the hubs (and corresponding catheters) along the length of the table may be determined in a variety of ways. For example, a non-contact magnetic sensor may be configured to directly measure the position of the hubs through the sterile barrier. The same type of sensor can also be configured to measure the position of the carriages. Each hub may have at least one magnet attached to it. The robotic table would have a linear array of corresponding magnetic sensors going the entire length of the table. A processor can be configured to determine the location of the magnet along the length of the linear sensor array, and display axial position information to the physician.

The foregoing may alternatively be accomplished using a non-contact inductive sensor to directly measure the position of the hubs through the sterile barrier. Each hub or carriage may be provided with an inductive “target” in it. The robotic table may be provided with an inductive sensing array over the entire working length of the table. As a further alternative, an absolute linear encoder may be used to directly measure the linear position of the hubs or carriages. The encoder could use any of a variety of different technologies, including optical, magnetic, inductive, and capacitive methods.

In one implementation, a passive (no electrical connections) target coil may be carried by each hub. A linear printed circuit board (PCB) may run the entire working length of the table (e.g., at least about 1.5 meters to about 1.9 meters) configured to ping an interrogator signal which stimulates a return signal from the passive coil. The PCB is configured to identify the return signal and its location.

Axial position of the carriages may be determined using a multi-turn rotary encoder to measure the rotational position of the pulley, which directly correlates to the linear position of the carriage. Direct measurement of the location of the carriage may alternatively be accomplished by recording the number of steps commanded to the stepper motor to measure the rotational position of the pulley, which directly correlates to the linear position of the carriage.

The location of the catheters and guidewires within the anatomy may also be determined by processing the fluoroscopic image with machine vision, such as to determine the distal tip position, distal tip orientation, and/or guidewire shape. Comparing distal tip position or movement or lack thereof to commanded or actual proximal catheter or guidewire movement at the hub, may be used to detect a loss of relative motion, which may be indicative of a device shaft buckling, prolapse, kinking, or a similar outcome (for example, along the device shaft length inside the body (e.g., in the aorta) or outside the body between hubs. The processing may be done in real time to provide position/orientation data at up to 30 Hertz, although this technique would only provide data while the fluoroscopic imaging is turned on. In some embodiments, machine vision algorithms can be used to generate and suggest optimal catheter manipulations to access or reach anatomical landmarks, similar to driver assist. The machine vision algorithms may utilize data to automatically drive the catheters depending on the anatomy presented by fluoroscopy.

Figure 14:
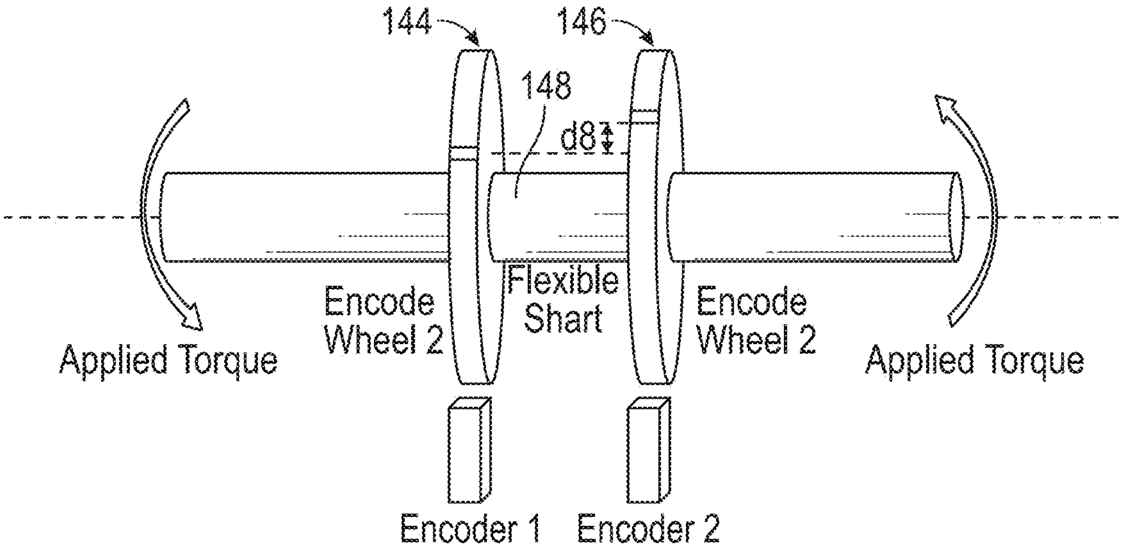
FIG. 14 schematically illustrates a dual encoder torque sensor for use with a catheter of the present disclosure.

Proximal torque applied to the catheter or guidewire shaft may be determined using a dual encoder torque sensor. Referring to FIG. 14, a first encoder 144 and a second encoder 146 may be spaced axially apart along the shaft 148, for measuring the difference in angle over a length of flexible catheter/tube. The difference in angle is interpolated as a torque, since the catheter/tube has a known torsional stiffness. As torque is applied to the shaft, the slightly flexible portion of the shaft will twist. The difference between the angles measured by the encoders ($d\theta$) tells us the torque. $T=k*d\theta$, where k is the torsional stiffness.

Confirming the absence of bubbles in fluid lines may also be accomplished using bubble sensors, particularly where the physician is remote from the patient. This may be accomplished using a non-contact ultrasonic sensor that measures the intensity and doppler shift of the reflected ultrasound through the sidewall of fluid tubing to detect bubbles and measure fluid flow rate or fluid level. An ultrasonic or optical sensor may be positioned adjacent an incoming fluid flow path within the hub, or in a supply line leading to the hub. To detect the presence of air bubbles in the infusion line (that is formed of ultrasonically or optically transmissive material) the sensor may include a signal source on a first side of the flow path and a receiver on a second side of the flow path to measure transmission through the liquid passing through the tube to detect bubbles. Alternatively, a reflected ultrasound signal may be detected from the same side of the flow path as the source due to the relatively high echogenicity of bubbles.

Preferably, a bubble removal system is automatically activated upon detection of in line bubbles. A processor may be configured to activate a valve positioned in the flow path downstream of the bubble detector, upon the detection of bubbles. The valve diverts a column of fluid out of the flow path to the patient and into a reservoir. Once bubbles are no longer detected in the flow path and after the volume of fluid in the flow path between the detector and the valve has passed through the valve, the valve may be activated to reconnect the source of fluid with the patient through the flow path. In other embodiments, the bubble removal system can include a pump and control system upstream of the bubble detector for removal of in line bubbles. A processor may be configured to activate the pump upon detection of bubbles to reverse the fluid flow and clear the bubbles into a waste reservoir before reestablishing bubble free forward flow.

Figure 15:
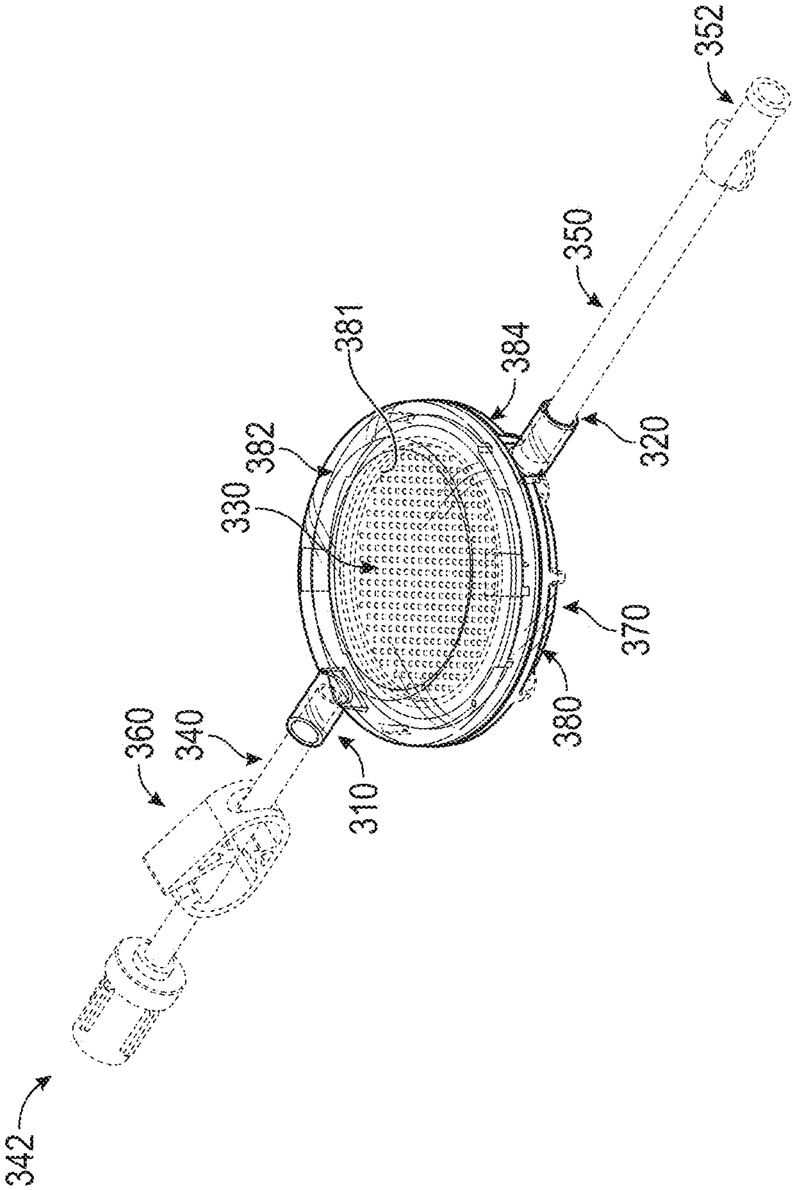
FIG. 15 illustrates a clot capture and visualization device that can be integrated into a hub and/or connected to an aspiration line.

It may additionally be desirable for the physician to be able to view aspirated clot at a location within the sterile field and preferably as close to the patient as practical for fluid management purposes. This may be accomplished by providing a clot retrieval device mounted on the hub, or in an aspiration line leading away from the hub in the direction of the pump. Referring to FIG. 15, one example of a clot retrieval device 370 can include a body 380 enclosing a chamber 381 which communicates with a first port 310 and a second port 320.

In some embodiments, the body 380 includes a housing having a top portion 382 and a bottom portion 384. The body 380 may include a filter 330 positioned in the chamber 381 between the top portion 382, and the bottom portion 384. In some examples, the first port 310 is configured to connect to a first end of a first tube 340 that is fluidly connected to a proximal end of an aspiration catheter.

In an embodiment that is configured to be connected downstream from the hub, the first tube 340 includes a connector 342 positioned at a second end of the first tube 340 that is configured to engage or mate with a corresponding connector on or in communication with the hub. The first port 310 directly communicates with the chamber on the upstream (e.g., top side) of the filter, and the second port 320 directly communicates with the chamber on the downstream (e.g., bottom side) of the filter to facilitate direct visualization of material caught on the upstream side of the filter.

In an implementation configured for remote operation, any of a variety of sensors may be provided to detect clot passing through the aspiration line and/or trapped in the filter, such as an optical sensor, pressure sensor, flow rate sensor, ultrasound sensor or others known in the art.

In some embodiments, the second port 320 is configured to connect to a first end of a second tube 350 that is fluidly connected to an aspiration source (e.g., a pump). In some embodiments, the second tube 350 includes a connector 352 positioned at a second end of the second tube 350 that is configured to engage or mate with a corresponding connector on the pump.

In some examples, the system 300 can include an on-off valve 360 such as a clamp. The clamp can be positioned in between the filter 330 and the patient, such as over the first tube 340 to allow the user to engage the clamp and provide flow control by isolating the patient from the clot retrieval device 370. Closing the valve 360 and operating the remote vacuum pump (not illustrated) causes the canister associated with the vacuum pump and the chamber 381 to reach the same low pressure. Due to the short distance and small line volume of the lumen between the chamber 381 end the distal end of the catheter, a sharp negative pressure spike is experienced at the distal end of the catheter rapidly following opening of the valve 360. Additional details are disclosed in U.S. Pat. No. 11,259,821 issued Mar. 1, 2022 to Buck et al., entitled Aspiration System with Accelerated Response, the entirety of which is hereby expressly incorporated by reference herein. In some embodiments, a vacuum may be cycled against a clot to retrieve the clot. The vacuum may be automatically and robotically controlled to remove the clot.

The body 380 can have a top surface spaced apart from a bottom surface by a tubular side wall. In the illustrated implementation, the top and bottom surfaces are substantially circular, and spaced apart by a cylindrical side wall. The top surface may have a diameter that is at least about three times, or five times or more than the axial length (transverse to the top and bottom surfaces) of the side wall, to produce a generally disc shaped housing. Preferably at least a portion of the top wall is optically transparent to improve clot visualization once it is trapped in the clot retrieval device 370. Additional details may be found in U.S. Patent Application No. 63/256,743, the entirety of which is hereby incorporated by reference herein.

In some examples, the body 380 can include a flush port (not illustrated) that is configured to allow the injection of an optically transparent media such as air, saline or other fluid into the chamber 381 to clear an optical path between the window and the filter to improve clot visualization once it is trapped in the filter 330.

The foregoing represents certain specific implementations of a drive table and associated components and catheters. A wide variety of different drive table constructions can be made, for supporting and axially advancing and retracting two or three or four or more drive magnet assemblies to robotically drive interventional devices, fluid elements, and electrical umbilical elements for communicating electrical signals and fluids to the catheter hubs, as will be appreciated by those of skill in the art in view of the disclosure herein. Additional details may be found in U.S. patent application Ser. No. 17/527,393, the entirety of which is hereby incorporated by reference herein.

While the foregoing describes robotically driven interventional devices and manually driven interventional devices, the devices may be manually driven, robotically driven, or a combination of both manually and robotically driven interventional devices, as will be appreciated by those of skill in the art in view of the disclosure herein.

Figure 16A:
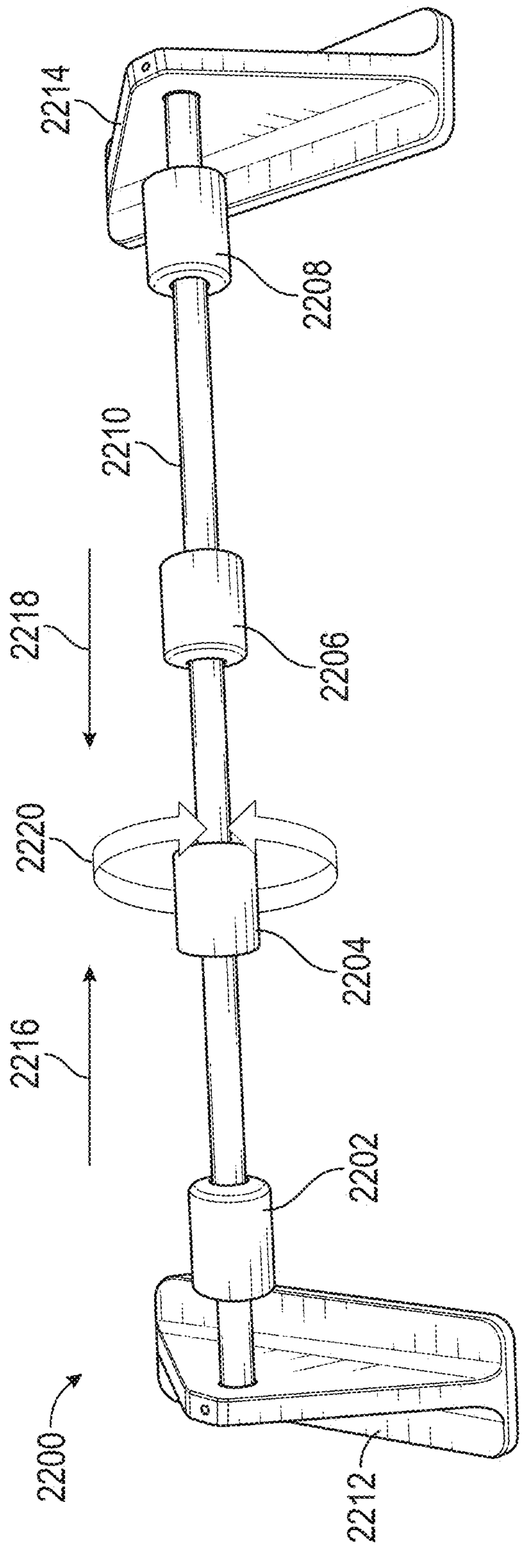
FIGS. 16A-16C illustrate an example control mechanism for manipulating interventional devices driven by respective hubs.
Figure 16B:
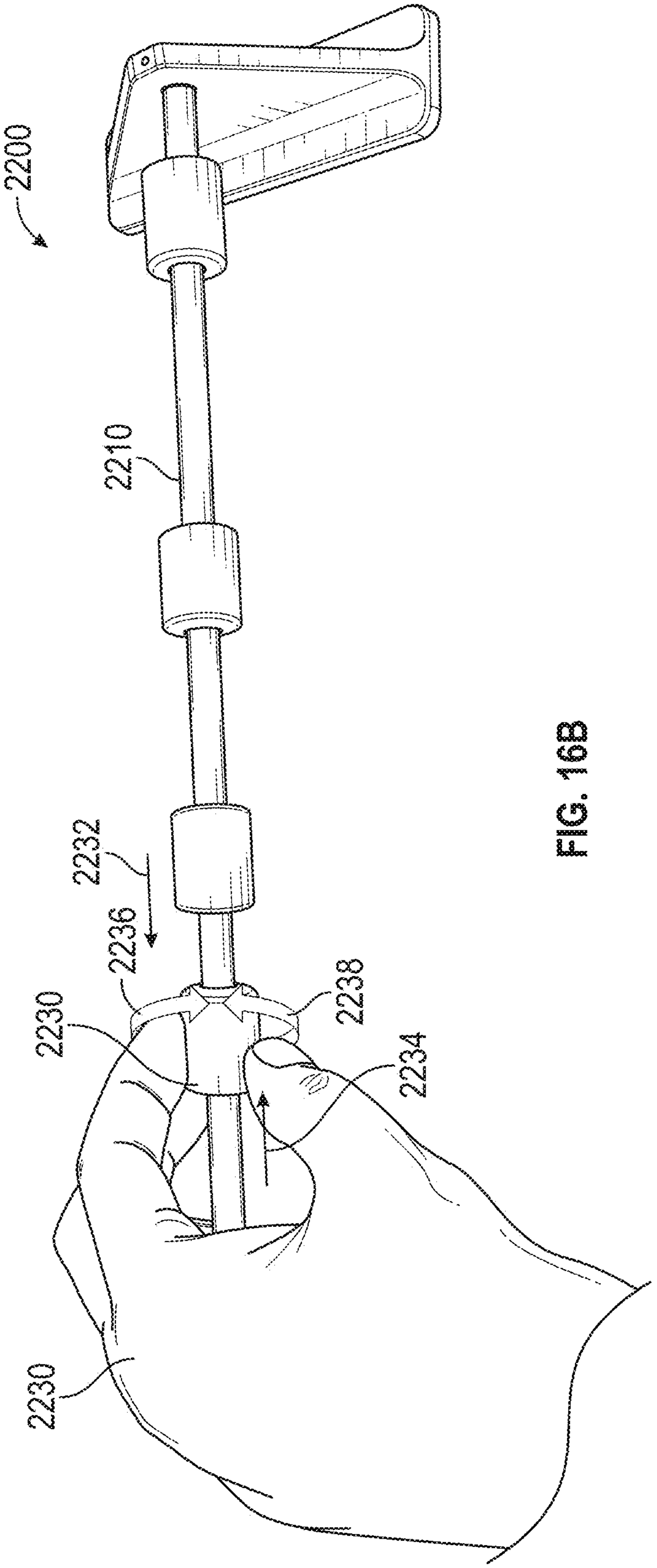
Figure 16C:
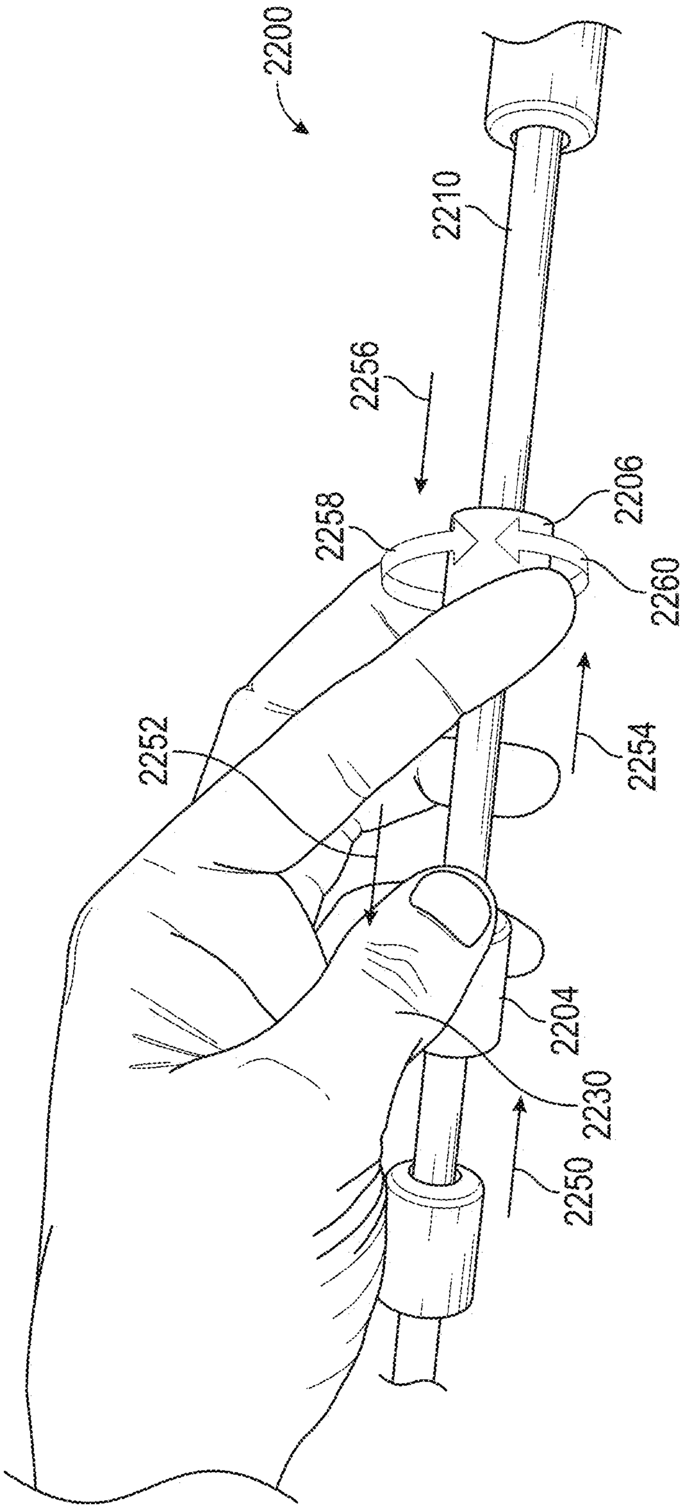

FIGS. 16A-16C illustrate an example control mechanism 2200 for manipulating interventional devices driven by (or otherwise associated with) respective hubs. For example, each hub may be manipulated and/or otherwise moved using at least one control installed in control mechanism 2200. Each control may be adapted to move a unique hub and associated interventional device during an interventional procedure.

As shown in FIG. 16A, the control mechanism 2200 can include a first control 2202, a second control 2204, a third control 2206, and a fourth control 2208. More or fewer controls may be provided, depending upon the intended interventional devices configuration. Each control 2202-

2208 is movably carried on a shaft 2210 that is coupled to a distal bracket 2212 and to a proximal bracket 2214. The controls 2202-2208 may advance distally or retract proximally on the shaft 2210, as indicated by arrow 2218 and arrow 2216. In addition, each control 2202-2208 may also be rotated about the shaft 2210, as indicated by arrow 2220. Each control movement may trigger a responsive movement in a corresponding carriage on the support table, which may in turn drive movement of a corresponding hub as has been discussed.

The control mechanism 2200 may be positioned on or near to a patient support table having a set of hubs and catheters/interventional devices. In some implementations, the control mechanism 2200 may be positioned remote from the support table such as behind a radiation shield or in a different room or different geographical location in a telemedicine implementation.

Each control 2202-2208 may correspond to and drive movement of a hub and/or a hub and interventional device combination. For example, the control 2202 may be configured to drive hub 30 (FIG. 3F) to move an interventional device such as an 0.088 inch guide catheter corresponding to the hub 30. Similarly, the control 2204 may be configured to drive hub 28 (122) to move an interventional device such as an 0.071 inch procedure catheter. The control 2206 may be configured to drive hub 126 to move an interventional device such as a steerable access catheter. The control 2208 may be configured to drive hub 26 to axially and rotationally move an interventional device such as a guidewire.

FIG. 16B illustrates an example of manually manipulating the control 2202 on control mechanism 2200. In operation, if the user 2230 moves the control 2202 axially along shaft 2210 and distally, as shown by arrow 2232, a corresponding coupled hub and/or interventional device may move responsively in the same direction by a same or scaled amount. If the user 2230 rotates the control 2202 about the shaft 2210 and advances the control proximally, as shown by arrow 2234, a corresponding coupled interventional device will responsively move rotationally and proximally by a same or scaled amount. If the user 2230 moves the control 2202 rotationally about the shaft 2210, as shown by arrow 2236 or arrow 2238, a corresponding coupled hub will drive the corresponding interventional device rotationally in the same direction and/or by a same or scaled amount.

Other axes and degrees of freedom may be defined to enable control 2202 to perform movements that may be translated to movement of hubs and/or interventional devices. For example, the control mechanism may be provided with one or more deflection controls configured to initiate a lateral deflection in a deflection zone on the corresponding interventional device.

Axial movement of a control may be configured to move the coupled hub on a 1:1 basis, or on a non 1:1 scaled basis. For example, if the user 2230 advances the control 2022 about 5 millimeters distally along the shaft 2210, then the corresponding hub may responsively move 5 millimeters in the distal direction.

If the user 2230 rotates the control 2022 about its rotational axis by 5 degrees, the coupled hub will cause the corresponding interventional device to rotate on a 1:1 basis or on a non 1:1 scaled basis. The scaled amount may be selected to reduce or increase the amount of distance and rotation that a hub and/or interventional device moves in accordance with the control movement.

In some implementations, the scaled amount described herein may be determined using a scale factor. The scale factor may apply to one or both translational and rotational movement. In some implementations, a first scale factor is selected for translational movement and a second scale factor, different than the first scale factor, is selected for rotational movement. The axial scaling factor may drive proximal catheter movement at a faster speed than distal catheter movement for a given proximal or distal manipulation of the control.

The rotational scale factor may be 1:1 while the axial scale factor may move the hub by a greater distance than movement of the control such that hub travel to control travel is at least about 2:1 or 5:1 or 10:1 or more depending upon the desired axial length of the control assembly.

The control mechanism 2200 may be configured to enable the clinician to adjust the scale factor for different parts of the procedure. For example, distal advance of the procedure catheter and access catheter through the guide catheter and up to the selected ostium may desirably be accomplished in a 'fast' mode. But more distal travel into the neuro vasculature may desirably be accomplished in a relatively slow mode by actuation of a speed control.

In another implementation, one or more controls may be configured to progressively drive advance or retraction speeds of the corresponding hub and associated catheter. For example, distal control 2202 may drive the guide catheter. A slight distal movement of the control 2202 may advance the guide catheter distally at a slow speed, while advancing the control 2202 by a greater distance distally increases the rate of distal travel of the guide catheter.

Controlling the speed of the corresponding hubs either axially or both axially and rotationally may enhance the overall speed of the procedure. For example, advance of the various devices from the femoral access point up to the aortic arch may desirably be accomplished at a faster rate than more distal navigation closer to the treatment site. Also proximal retraction of the various devices, particularly the guidewire, access catheter and procedure catheter may be desirably accomplished at a relatively higher speeds than distal advance.

FIG. 16C illustrates another example of manually manipulating a control on the control mechanism 2200 to move hubs and/or other interventional devices. In some implementations, two or more controls 2202-2208 may be moved in combination to trigger movement of one or more hubs and/or related interventional devices. In the depicted example, the user 2230 moves control 2204 and control 2206 in combination (e.g., sequentially, simultaneously) such as to simultaneously move the 0.088 guide catheter and the 0.071 aspiration catheter as a unit. Example movement of control 2204 may include axial proximal movement in the directions shown by arrows 2250. Sequentially or simultaneously, the user 2230 may move control 2206 axially in either of the directions shown by arrows 2254 and 2256 while also moving control 2206 rotationally in either of the directions shown by arrows 2258 and 2260.

In some implementations, each control mechanism and/or additional controls (not shown) may be color coded, shaped coded, tactile coded, or other coding to indicate to the user 2230 which color is configured to move which hub or interventional device. In some implementations, the control color coding may also be applied to the hubs and/or interventional devices such that a user may visually match a particular hub/device with a particular control.

In some implementations, other control operations beyond translational movement and rotational movement may be carried out using controls 2202-2208. For example, controls 2202-2208 may be configured to drive a shape change and/or stiffness change of a corresponding interventional device. Controls 2202-2208 may be toggled between different operating modes. For example, controls 2202-2208 may be toggled between movement driven by acceleration and velocity to movement that reflects actual linear displacement or rotation.

In some implementations, the control mechanism 2200 may be provided with a visual display or other indicator of the relative positions of the controls which may correspond the relative positions of the interventional devices. Such displays may depict any or all movement directions, instructions, percentage of movements performed, and/or hub and/or catheter indicators to indicate which device is controlled by a particular control. In some implementations, the display may depict applied force or resistance encountered by the catheter or other measurement being detected or observed by a particular hub or interventional component.

In some implementations, the control mechanism 2200 may include haptic components to provide haptic feedback to a user operating the controls. For example, if the control 2202 is triggering movement of a catheter and the catheter detects a large force at the tip, the control 2202 may generate haptic feedback to indicate to the user to stop or reverse a performed movement. In some implementations, haptic feedback may be generated at the control to indicate to the user to slow or speed a movement using the control. In some implementations, haptics may provide feedback on a large torsional strain buildup that might precede an abrupt rotation, or a large axial force buildup that may be a prelude to buckling of the catheter.

The systems described herein may compare an actual fluoroscopic image position to an input displacement from the controller. A static fluoroscopic image of the patient may be captured in which the patient's vasculature is indexed relative to bony landmarks or one or more implanted soft tissue fiducial markers. Then a real time fluoroscopic image may be displayed as an overlay, aligned with the static image by registration of the fiducial markers. Visual observation of conformance of the real time movement with the static image, assisted by detected force data can help confirm proper navigation of the associated catheter or guidewire. The systems described herein can also display a comparison of an input proximal mechanical translation of a catheter or guidewire and a resulting distal tip output motion or lack thereof. A loss of relative motion at the distal tip may indicate shaft buckling, prolapse, kinking, or a similar outcome, either inside or outside the body. Such a comparison may be beneficial when the shaft buckling, prolapse, kinking, or similar outcome occurs outside of a current fluoroscopic view.

Figure 17:
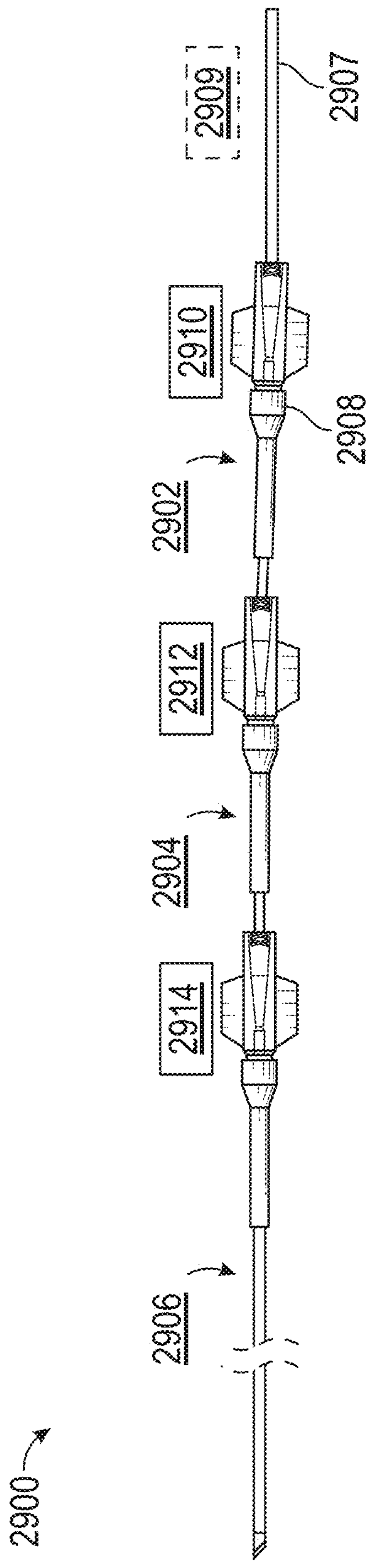
FIG. 17 illustrates a side elevational schematic view of an interventional device assembly for supra-aortic access and neuro-interventional procedures.

FIG. 17 illustrates a side elevational schematic view of a multi catheter interventional device assembly 2900 for combined supra-aortic access and/or neurovascular site access and procedure (e.g., aspiration), as described herein. The multi catheter assembly 2900 may be configured for either a manual or a robotic procedure.

The interventional device assembly 2900 includes an insert or access catheter 2902, a procedure catheter 2904, and a guide catheter 2906. Other components are possible including, but not limited to, one or more guidewires (e.g., optional guidewire 2907), one or more guide catheters, an access sheath and/or one or more other procedure catheters and/or associated catheter (control) hubs. In some embodiments, the assembly 2900 may also be configured with an optional deflection control 2908 for controlling deflection of one or more interventional devices (e.g., catheters, microcatheters, or wires such as guidewires or hollow wires) of the assembly 2900.

In operation, the multi-catheter assembly 2900 may be used without having to exchange hub components. For example, in the two stage procedure disclosed previously, a first stage for achieving supra-aortic access, includes mounting an access catheter, guide catheter and guidewire to the support table. Upon gaining supra aortic access, the access catheter and guidewire were typically removed from the guide catheter. Then, a second catheter assembly is introduced through the guide catheter after attaching a new guidewire hub and a procedure catheter hub to the corresponding drive carriage on the support table.

The single multi catheter assembly 2900 of FIG. 17 is configured to be operated without having to remove hubs and catheters and without the addition of additional assemblies and/or hubs. Thus, the multicomponent access and procedure configuration of assembly 2900 may utilize a guidewire 2907 manufactured to function as an access guidewire and a navigation guidewire to allow for sufficient access and support, and navigation to the particular distal treatment site. In a non-limiting example configured for robotic implementation, a catheter assembly may include a guidewire hub (e.g., guidewire hub 2909 or guidewire hub 26 positioned on a drive table and to the right of catheter 2902), an insert or access catheter hub 2910, a procedure catheter hub 2912, a guide catheter hub 2914 and corresponding catheters. In certain embodiments, one or more of the hubs may include or be coupled to a hemostasis valve (e.g., a rotating hemostasis valve) to accommodate introduction of interventional devices therethrough. Additional details regarding hemostasis valves are included in U.S. patent application Ser. No. 17/879,614, entitled Multi Catheter System With Integrated Fluidics Management, filed Aug. 2, 2022, which is hereby expressly incorporated in its entirety herein.

Once access above the aortic arch has been achieved, the insert or access catheter 2902 (associated with insert catheter hub 2910) may be parked in the vicinity of a carotid artery ostia and the remainder or a subset of the catheter assembly may be guided more distally toward a particular site (e.g., a clot site, a surgical site, a procedure site, etc.).

In some embodiments, other smaller procedure catheters may also be added and used at the site. As used herein for catheter assembly 2900, in a robotic configuration of assembly 2900, the catheter 2906 may function as a guide catheter. The catheter 2904 may function as a procedure (e.g., aspiration) catheter. In some embodiments, the catheter 2906 may function to perform aspiration in addition to functioning as a guide catheter, either instead of or in addition to the catheter 2904. The access catheter 2902 may have a distal deflection zone and can function to access a desired ostium. In some embodiments, the guidewire 2907 may have a distal deflection zone and can function to access a desired ostium. One of skill in the art will appreciate from FIGS. 18A-18E that either manual manipulation or robotic manipulation of the multi catheter stack are contemplated herein.

In some embodiments, the catheter assembly 2900 (or other combined catheter assemblies described herein) may be driven as a unit to a location. However, each catheter (or guidewire) component may instead be operated and driven independent of one another to the same or different locations.

In a non-limiting example, the catheter assembly 2900 may be used for a diagnostic angiogram procedure. In some embodiments, the assembly 2900 may include only the guidewire 2907 and access catheter 2902 (in the form of a diagnostic angiographic catheter) for performing the diagnostic angiogram procedure or only the guidewire 2907 and the access catheter 2902 may be utilized during the procedure. Alternatively, the guide catheter 2906 and procedure catheter 2904 may be retracted proximally to expose the distal end of the access catheter 2902 (e.g., a few centimeters of the distal end of the access catheter) to perform the diagnostic angiography. The diagnostic angiogram procedure can be performed at any point during the procedure. In some embodiments, the interventional devices (e.g., catheters and guidewires) can be adequately spaced to perform contrast injection in parallel, around, or inside the other interventional devices.

As shown in FIG. 17, the guide catheter 2906, procedure catheter 2904, access catheter 2902, and guidewire 2907 can be arranged concentrically. In certain embodiments, the guide catheter 2906 may be a 'large bore' guide catheter or access catheter having an inner diameter of at least about 0.075 or at least about 0.080 inches in diameter. The procedure catheter 2904 may be an aspiration catheter having an inner diameter within the range of from about 0.060 to about 0.075 inches. The access catheter 2902 may be a steerable catheter with a deflectable distal tip, having an inner diameter within the range of from about 0.025 to about 0.050 inches. The guidewire 2907 may have a diameter within the range of from about 0.014 to about 0.020 inches. In one example, the guide catheter 2906 may have an inner diameter of about 0.088 inches, the procedure catheter 2904 may have an inner diameter of about 0.071 inches, the access catheter 2902 may have an inner diameter of about 0.035 inches, and the guidewire 2907 may have a diameter of about 0.018 inches.

FIGS. 18A-18E depict an example sequence of steps of introducing a multi-catheter assembly configured to achieve access all the way to the clot, either manually or robotically. FIGS. 18A-18E may be described using the interventional device assembly of FIG. 17. Other combinations of catheters may be substituted for the interventional device assembly, as will be appreciated by those of skill in the art in view of the disclosure herein.

Figure 18A:
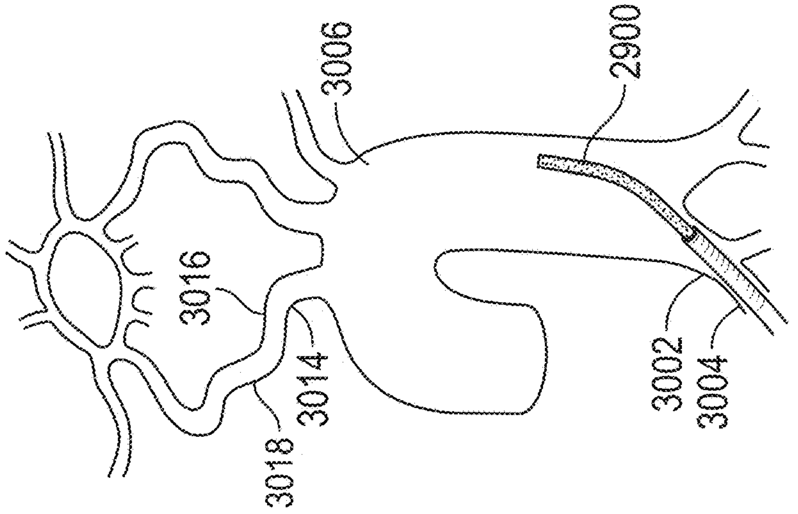
FIGS. 18A-18E depict an example sequence of steps of introducing a catheter assembly configured to achieve supra-aortic access and neurovascular site access.
Figure 18B:
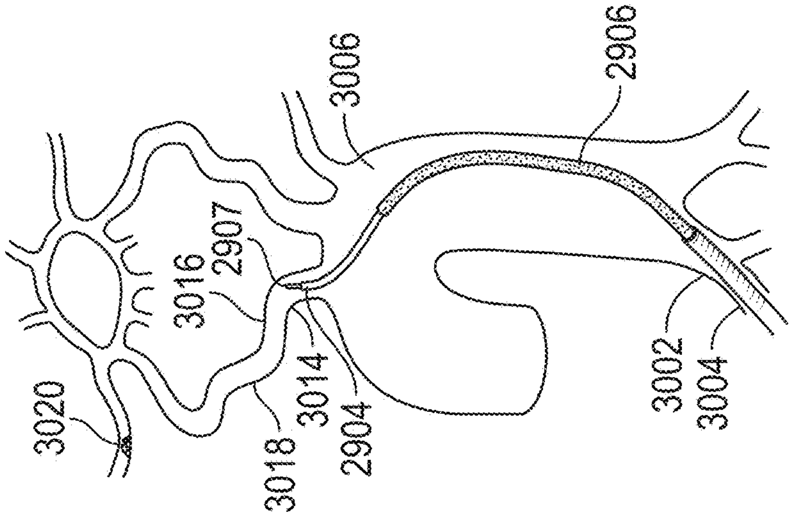

Referring to FIG. 18A, the three catheter interventional device assembly 2900 is shown driven through an introducer sheath 3002, up through the iliac artery 3004 and into the descending aorta. In some embodiments, the three-catheter interventional device assembly can be driven through an introducer sheath 3002, up through the femoral artery and into the descending aorta. Next, the access catheter 2902, the procedure catheter 2904 (e.g., 0.071 inch) and the guide catheter 2906 (e.g., 0.088 inch) are tracked up to the aortic arch 3006, as shown in FIG. 18B. Here, the distal end of the guide catheter 2906 may be parked below the aortic arch 3006 and the procedure catheter 2904, access catheter 2902 (positioned within the procedure catheter 2904 and not visible in FIG. 18B), and a guidewire 2907 can be driven into the ostium (e.g., simultaneously or separately). In some embodiments, the access catheter 2902 is advanced out of the procedure catheter 2904 and the guide catheter 2906 to engage the ostium first. After the distal end of the access catheter 2902 is positioned within the desired ostium, the guidewire 2907 can be advanced distally into the ostium to secure access. After the access catheter 2902 and guidewire 2907 are positioned within the desired ostium, the procedure catheter 2904 and/or guide catheter 2906 can be advanced into the ostium (and, in some embodiments, beyond), while using the support of the access catheter 2902 and/or guidewire 2907 to maneuver through the aorta and into the ostium. In the embodiment shown in FIG. 18B, the procedure catheter 2904 has been advanced into the ostium while the guide catheter 2906 has remained parked below the aortic arch 3006.

Figure 18C:
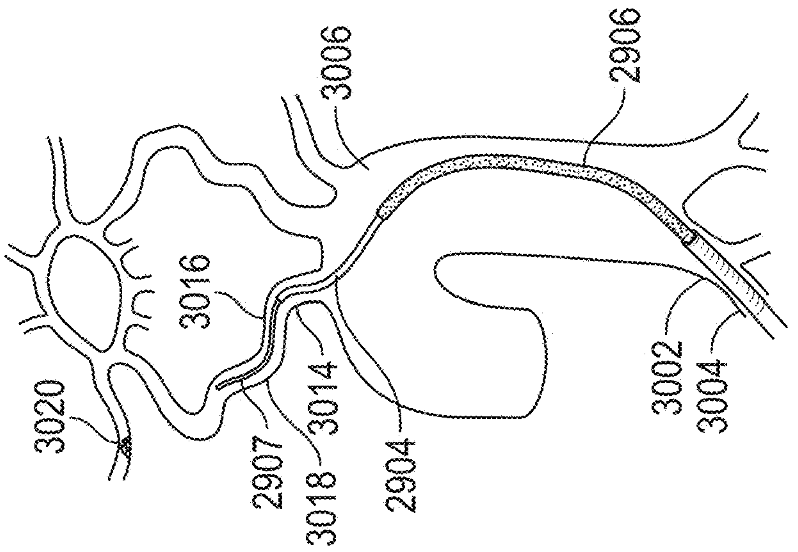

Referring to FIG. 18C, the guidewire 2907 may be distally advanced and the radiopacity of the guidewire 2907 may be used to confirm under fluoroscopic imaging that access through the desired ostia has been attained. The guidewire 2907 engages the origin of the brachiocephalic artery 3014. The guidewire 2907 is then advanced near the petrous segment 3018 (e.g., up to the petrous segment 3018 or proximally or distally adjacent the petrous segment 3018) of the internal carotid artery 3016.

Figure 18E:
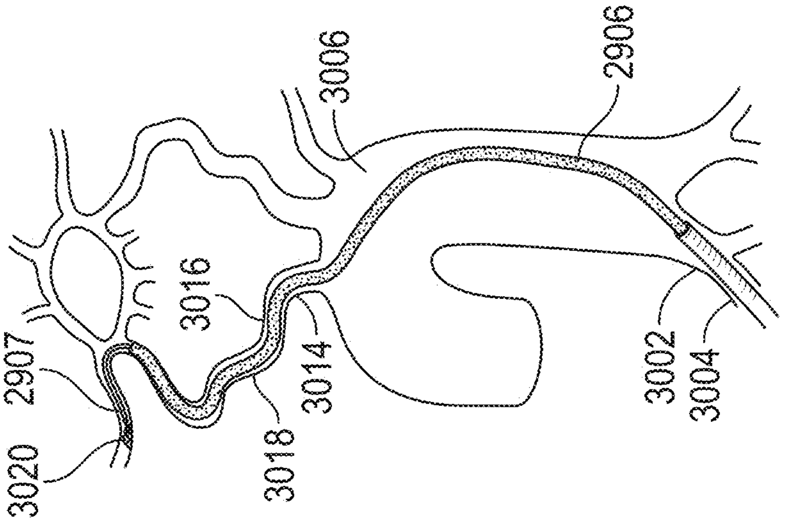
Figure 18D:
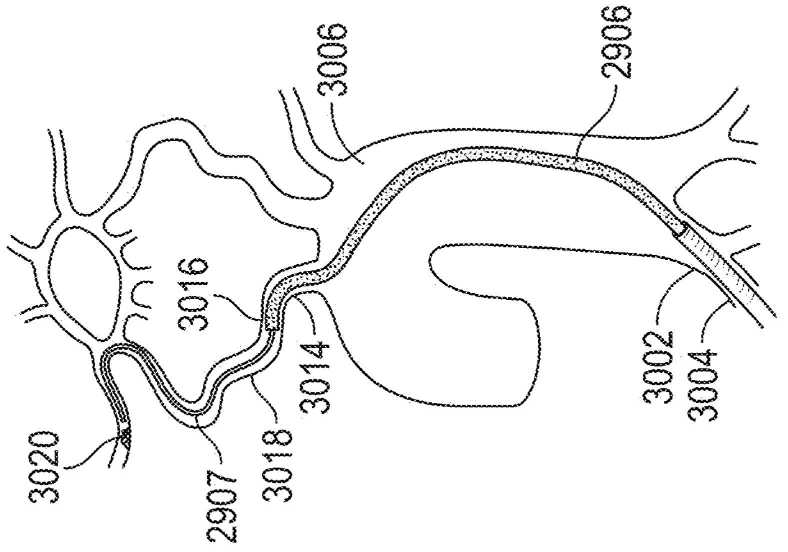

Referring to FIG. 18D, the guide catheter 2906 and the procedure catheter 2904 (positioned within the guide catheter 2906 and not visible in FIG. 18D) are both advanced (e.g., simultaneously or sequentially) over the guidewire 2907 and over the insert or access catheter 2902 (positioned within the procedure catheter 2904 and not visible in FIG. 18D) while the access catheter 2902 remains at the ostium for support. The guidewire 2907 may be further advanced past the petrous segment 3018 to the site of the clot 3020, such as the M1 segment.

Referring to FIG. 18E, the guide catheter 2906 and the procedure catheter 2904 (positioned within the guide catheter 2906 and not visible in FIG. 18E) are advanced (e.g., simultaneously or sequentially) to position the distal tip of the procedure catheter 2904 at the procedure site, for example on the face of the clot 3020. The guidewire 2907 and access catheter 2902 (positioned within the procedure catheter 2904 and not visible in FIG. 18E) are removed, and aspiration of the clot 3020 commences through the procedure catheter 2904. That is, the guidewire 2907 and the access catheter 2902 are proximally retracted to allow aspiration through the procedure catheter 2904. After aspiration of the clot, the procedure catheter 2904 and guide catheter 2906 can be removed (e.g., simultaneously or sequentially). For example, in some embodiments, the procedure catheter 2904 may be removed before removing the guide catheter 2906.

The catheter assembly 2900 may be used to perform a neurovascular procedure, as described in FIGS. 18A-18E. For example, the neurovascular procedure may be a neurovascular thrombectomy. The steps of the procedure may include providing an assembly that includes at least a guidewire, an access catheter, a guide catheter, and a procedure catheter. For example, the catheter assembly 2900 includes a guidewire 2907, an access (e.g., insert) catheter 2902, a guide catheter 2906, and at least one procedure catheter 2904. The procedure catheter 2904 may include an aspiration catheter, an embolic deployment catheter, a stent deployment catheter, a flow diverter deployment catheter, a diagnostic angiographic catheter, a stent retriever catheter, a clot retriever catheter, a balloon catheter, a catheter to facilitate percutaneous valve repair or replacement, an ablation catheter, and/or an RF ablation catheter or guidewire.

The neurovascular procedure may further include steps of coupling the assembly to a non-robotic or a robotic drive system, and driving the assembly to achieve supra-aortic access. The steps may further include driving a subset of the assembly to a neurovascular site, and performing the neurovascular procedure using a subset of the assembly. The subset of the assembly may include the guidewire, the guide catheter, and the procedure catheter.

Each of the guidewire 2907, the access catheter 2902, the guide catheter 2906, and the procedure catheter 2904 is configured to be adjusted by a respective hub. For example, the guidewire 2907 may include (or be coupled to) a hub installed on one of the tray assemblies described herein. Similarly, the access catheter 2902 may be coupled to catheter hub 2910. The guide catheter 2906 may be coupled to the guide catheter hub 2914. The procedure catheter 2904 may be coupled to the procedure catheter hub 2912.

In general coupling of the assembly may include magnetically coupling a first hub 2909 on the guidewire 2907 to a first drive magnet, magnetically coupling a second hub 2910 on the access catheter 2902 to a second drive magnet, magnetically coupling a third hub 2912 on the procedure catheter 2904 to a third drive magnet, and magnetically coupling a fourth hub 2914 on the guide catheter 2906 to a fourth drive magnet. In general, the first drive magnet, the second drive magnet, the third drive magnet, and the fourth drive magnet are each independently movably carried by a drive table, as described with respect to tray assemblies and controls described herein. In some embodiments, the first drive magnet, the second drive magnet, the third drive magnet, and the fourth drive magnet are coupled (e.g., to their respective catheter hubs) through a sterile barrier (e.g., a sterile and fluid barrier) and independently movably carried by a drive table having a plurality of driven magnets. In some embodiments, two or more drive magnets can be tethered or otherwise coupled together to move as a unit in response to commands from a single controller tethered or otherwise coupled to one of the drive magnets.

In some implementations, the steps of performing the neurovascular procedure may include driving the assembly in response to movement of each of the hub adapters along a support table until the assembly is positioned to achieve supra-aortic vessel access. The hub adapters may include, for example, a coupler/carriage that acts as a shuttle by advancing proximally or distally along a track in response to operator instructions. The hub adapters described herein may each include at least one drive magnet configured to couple with a driven magnet carried by the respective hub. This provides a magnetic coupling between the drive magnet and driven magnet through the sterile barrier such that the respective hub is moved across the top of the sterile barrier in response to movement of the hub adapter outside of the sterile field (as described in detail in FIG. 4). Movement of the hub adapter is driven by a drive system carried by the support table in which the guidewire hub 2909, the guide catheter hub 2914, the procedure catheter hub 2912, and the access catheter hub 2910 are installed upon.

The steps may further include driving a subset of the assembly in response to movement of each of the hub adapters along the support table until the subset of the assembly is positioned to perform a neurovascular procedure at a neurovascular treatment site. The subset of the assembly may include the guidewire 2907, the guide catheter 2906, and the procedure catheter 2904.

In some embodiments, the guidewire 2907, the guide catheter 2906 and the procedure catheter 2904 are advanced as a unit through (with respect to the guidewire 2907) and over (with respect to the guide catheter 2906 and the procedure catheter 2904) at least a portion of a length of the access (e.g., insert) catheter 2902 after supra-aortic access is achieved.

In some embodiments, the catheter assembly 2900 may be part of a robotic control system for achieving supra-aortic access and neurovascular treatment site access, as described in FIGS. 18A-18E. In some embodiments, the catheter assembly 2900 may be part of a manual control system for achieving supra-aortic access and neurovascular treatment site access. In some embodiments, the catheter assembly 2900 may be part of a hybrid control system (with manual and robotic components) for achieving supra-aortic access and neurovascular treatment site access. For example, in such hybrid systems, supra-aortic access may be robotically driven while neurovascular site access and embolectomy or other procedures may be manual. Alternatively, in such hybrid systems, supra-aortic access may be manual while neurovascular site access may be robotically achieved. Still further, in such hybrid systems, any one or more of: the guidewire, access catheter, guide catheter, or procedure catheter may be robotically driven or manually manipulated.

In some embodiments, a user may manually control an interventional device by hand or manually control interventional devices with both hands. The robotic control system can automatically move other interventional devices in concert with the manually controlled interventional devices. In some embodiments, the robotically controlled interventional devices can be controlled by a second user. In other embodiments, the robotically controlled interventional devices can be controlled by the same user as the manually controlled catheters. For example, in some embodiments, a control for robotically controlling an interventional device may be positioned on or adjacent to the interventional device or its corresponding to hub so that the user can manipulate the control with one hand while manually manipulating another interventional device. In some embodiments, the robotically controlled catheters can be controlled by a user without the user using their hands. For example, the robotically controlled catheters can be controlled by a user's feet (e.g., via foot pedals).

In some embodiments, during a procedure, one or more robotically driven interventional devices may be exchanged with one or more manually driven interventional devices. For example, one or more robotically driven interventional devices may be used at a beginning of a procedure and then removed and replaced with one or more manually driven interventional devices during later steps of the procedure. In some embodiments, the manually driven interventional devices may be longer than conventional manually controlled interventional devices in order to interface with the robotically driven interventional devices. In some embodiments, one or more robotically controlled catheters may be left in place during a procedure, and one or more manually controlled interventional devices may be inserted and manipulated through the robotically controlled catheters. For example, in some embodiments, a manually controlled aspiration catheter may be inserted into the catheter assembly 2900 (e.g., through a robotically controlled guide catheter 2906) in place of a robotically controlled access catheter 2902 and/or a robotically controlled procedure catheter 2904. The manually controlled aspiration catheter may have a smaller diameter than the robotically controlled access catheter 2902 or the robotically controlled procedure catheter 2904.

In some embodiments, stents, flow diverters, stent retrievers, stent retriever delivery microcatheters, coils, microcatheters, balloons, guidewires and/or any other suitable devices may be manually or robotically inserted into a patient's body through an access point (e.g., a femoral or iliac access point). For example, the stents, flow diverters, stent retrievers, stent retriever delivery microcatheters, coils, microcatheters, balloons, guidewires and/or any other suitable devices may be inserted into a patient's body through a guide catheter, such as guide catheter 2906. The guide catheter 2906 and/or any other interventional devices described herein may be manually or robotically inserted into a patient's body through the access point (e.g., a femoral or iliac access point).

In some embodiments, stents, flow diverters, stent retrievers, coils, microcatheters, balloons, guidewires and/or any other suitable devices may be inserted into a patient's body and navigated up through the descending aorta to a target site within the patient's vasculature. In some embodiments, the stents, flow diverters, stent retrievers, coils, microcatheters, balloons, guidewires and/or other suitable devices may be manually inserted through an access point (e.g., a femoral or iliac access point) in the patient's body and then robotically controlled to navigate up through the descending aorta to the target site. In some embodiments, stents, flow diverters, stent retrievers, coils, microcatheters, balloons, guidewires and/or other suitable devices may be manually inserted through an access point (e.g., a femoral or iliac access point) in the patient's body and then manually controlled to navigate up through the descending aorta to the target site. Accordingly, the stents, flow diverters, stent retrievers, coils, microcatheters, balloons, guidewires and/or other suitable devices may be inserted through a robotically and/or manually inserted and controlled guide catheter 2906. In some procedures, a user may simultaneously control a robotically controlled interventional device using one hand (e.g., using a left hand to move or actuate a switch on a hub) while manually manipulating an interventional device or devices using the other hand (e.g., the right hand).

In some embodiments, as described herein, force sensing may be used to detect energy storage. In some embodiments, the robotic control system can utilize force sensing of energy storage and accompanying control algorithms to actively compensate for energy storage in the robotically controlled interventional devices while the user advances other interventional devices manually.

In certain embodiments, any of the manually driven and/or robotically driven catheters may be coupled to one or more fluid and/or vacuum sources to provide fluids (e.g., saline, contrast, liquid drugs, etc.) or vacuum to the catheter. In some embodiments, any of the fluid and/or vacuum sources may be manually operated or robotically operated (e.g., automated). For example, in certain embodiments, one or more manually driven catheters may be coupled to a robotically operated fluidics system. In some embodiments, one or more robotically driven catheters can be coupled to a manually operated fluidics system. In some embodiments, an interventional device assembly, such as interventional device assembly 2900 can be coupled to a fluidics system having both manually operated fluidics and robotically operated fluidics. In some embodiments, a single fluidics system or fluidics machine can simultaneously manage fluidics injection and aspiration to both robotically drive and manually manipulated catheters.

Additional details regarding fluidics systems are disclosed in U.S. patent application Ser. No. 17/879,614, entitled Multi Catheter System With Integrated Fluidics Management, filed Aug. 2, 2022, which is hereby expressly incorporated in its entirety herein.

An example robotic control system may include at least a guidewire hub (e.g., guidewire hub 2909) configured to adjust each of an axial position and a rotational position of a guidewire 2907. The robotic control system may also include an access catheter hub 2910 configured to adjust axial and rotational movement of an access catheter 2902. The robotic control system may also include a guide catheter hub 2914 configured to control axial movements of a guide catheter 2906. In some embodiments, the robotic control system can control rotational movements of the guide catheter 2906. The robotic control system may also include a procedure catheter hub 2912 configured to adjust an axial position and a rotational position of a procedure catheter 2904.

In some embodiments, the procedure catheter hub 2912 is further configured to laterally deflect a distal deflection zone of the procedure catheter 2904.

In some embodiments, the guidewire hub 2909 is configured to couple to a guidewire hub adapter by magnetically coupling the guidewire hub to a first drive magnet. The access catheter hub 2910 is configured to couple to an access catheter hub adapter by magnetically coupling the access catheter hub 2910 to a second drive magnet. The procedure catheter hub 2912 is configured to couple to a procedure catheter hub adapter by magnetically coupling the procedure catheter hub 2912 to a third drive magnet. The guide catheter hub 2914 is configured to couple to a guide catheter hub adapter by magnetically coupling the guide catheter hub 2914 to a fourth drive magnet. In some embodiments, the first drive magnet, the second drive magnet, the third drive magnet, and the fourth drive magnet are independently movably carried by a drive table.

In some embodiments, the robotic control system includes a first driven magnet on the guidewire hub 2909. The first driven magnet may be configured to cooperate with the first drive magnet such that the first driven magnet is configured to move in response to movement of the first drive magnet. In some embodiments, the first drive magnet is configured to move outside of a sterile field separated from the first driven magnet by a barrier while the first driven magnet is within the sterile field. In some embodiments, a position of the first driven magnet is movable in response to manipulation of a procedure drive control on a control console associated with the drive table. Drive magnets and driven magnet interactions are described in detail with respect to FIG. 4 above.

In some embodiments, the robotic control system includes a second driven magnet on the access catheter hub 2910. The second driven magnet may be configured to cooperate with the second drive magnet such that the second driven magnet is configured to move in response to movement of the second drive magnet. In some embodiments, the second drive magnet is configured to move outside of a sterile field separated from the second driven magnet by a barrier while the second driven magnet is within the sterile field.

In some embodiments, the robotic control system includes a third driven magnet on the procedure catheter hub 2912. The third driven magnet may be configured to cooperate with the third drive magnet such that the third driven magnet is configured to move in response to movement of the third drive magnet. In some embodiments, the third drive magnet is configured to move outside of a sterile field separated from the third driven magnet by a barrier while the third driven magnet is within the sterile field.

In some embodiments, the robotic control system includes a fourth driven magnet on the guide catheter hub 2914. The fourth driven magnet may be configured to cooperate with the fourth drive magnet such that the fourth driven magnet is configured to move in response to movement of the fourth drive magnet. In some embodiments, the fourth drive magnet is configured to move outside of a sterile field separated from the fourth driven magnet by a barrier while the fourth driven magnet is within the sterile field. In some embodiments, there may be more than four driven magnets and corresponding catheter hubs for control of additional catheters.

In some embodiments, devices (e.g., hubs, hub adapters, interventional devices, and/or trays) described herein may be used during a robotically driven procedure. For example, in a robotically driven procedure, one or more of the interventional devices may be driven through vasculature and to a procedure site. Robotically driving such devices may include engaging electromechanical components that are controlled by user input. In some implementations, users may provide the input at a control system that interfaces with one or more hubs and hub adapters.

In some embodiments, the hubs, hub adapters, interventional devices, and trays described herein may be used during a non-robotic (e.g., manually driven) procedure. Manually driving such devices may include engaging manually with the hubs to affect movement of the interventional devices.

In some embodiments, the devices described herein may be used to carry out a method of performing an intracranial procedure at an intracranial site. The method of performing the intracranial procedure may include any of the same steps as described herein for performing a neurovascular procedure. The procedure may be robotically performed, manually performed, or a hybridized combination of both.

While the foregoing describes magnetic coupling of hubs to drive magnets, in other embodiments, any of the interventional devices and/or hubs may be mechanically coupled to a drive system. Any of the methods described herein may include steps of mechanically coupling one or more interventional devices (e.g., the guidewire 2907, the access catheter 2902, the procedure catheter 2904, and/or the guide catheter 2906) and/or one or more hubs (e.g., the guidewire hub 2909, the access catheter hub 2910, the procedure catheter hub 2912, and/or the guide catheter hub 2914) with one or more drive mechanisms.

Figure 19:
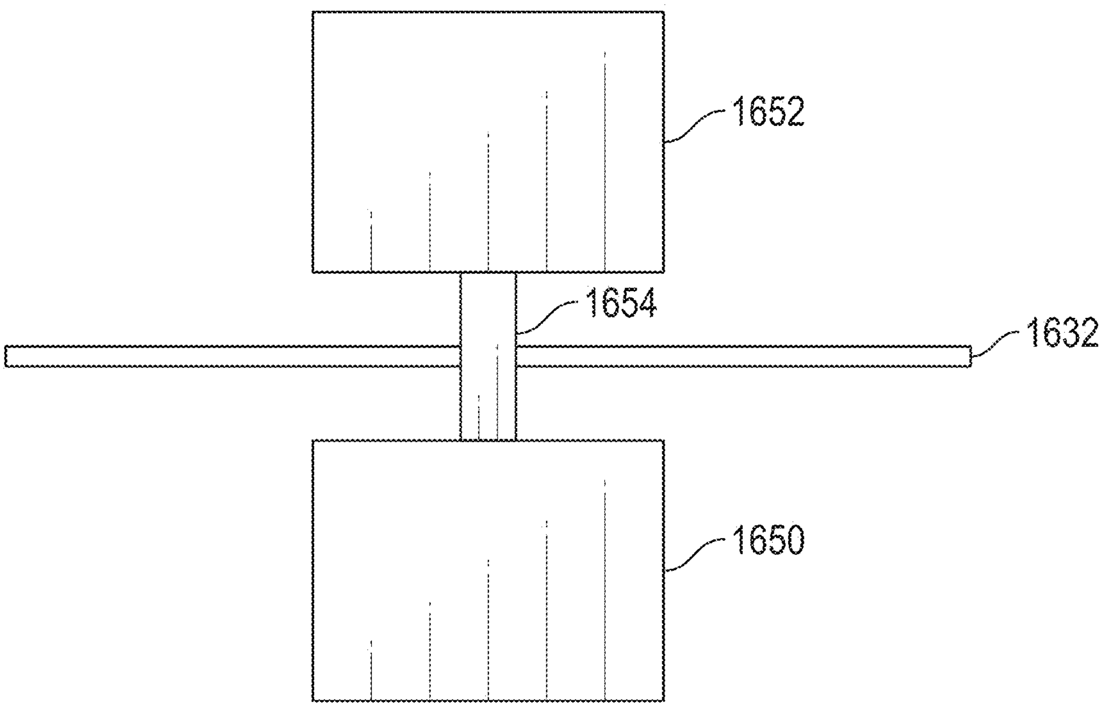
FIG. 19 schematically illustrates an embodiment of a mechanical coupling between a drive mechanism and a driven mechanism.

FIG. 19 illustrates a mechanical coupling mechanism 1654 between a drive mechanism 1650 and a driven mechanism 1652. Drive mechanism 1650 and driven mechanism 1652 may have any of the same or similar features or functions as the drive magnet 67 and driven magnet 69, respectively, except as otherwise described herein. The drive mechanism 1650 may be part of or coupled to a hub adapter (e.g., the hub adapter 48). The driven mechanism 1652 may be part of or coupled to a hub (e.g., the hub 36, the guidewire hub 2909, the access catheter hub 2910, the procedure catheter hub 2912, or the guide catheter hub 2914). In some instances, the mechanical coupling mechanism 1654 may comprise a structural support (e.g., a support rod or support strut) extending transversely through a seal in a sterile barrier 1632. The seal may permit the structural support to be advanced along a length of the sterile barrier 1632, while still maintaining a seal with the structural support to maintain the sterile field, as the drive mechanism 1650 and driven mechanism 1652 are advanced and/or retracted as described herein. For example, the seal may comprise a tongue and groove closure mechanism along the sterile barrier 1632 that is configured to close on either side of the structural support while permitting passage of the structural support through the sterile barrier 1632 and maintaining a seal against the structural support as the structural support is advanced along the length of the sterile barrier 1632.

In some embodiments, the structural support can extend through an elongate self closing seal between two adjacent coaptive edges of flexible material (e.g., similar in shape to a duckbill valve) that extends along an axis. As the structural support advances along the axis between the coaptive edges, the coaptive edges may permit the structural support to advance, and then may be biased back into a sealing engagement with each other as the structural support passes any given point along the axis.

In some embodiments, the drive mechanism may be a splined drive shaft (e.g., a non-sterile splined drive shaft). The mechanical coupling mechanism 1654 can include a pulley within a plate that serves as the sterile barrier 1632 and a sterile splined shaft configured to couple to the driven mechanism 1652. The driven mechanism 1652 can be a sterile pulley that receives the sterile splined shaft from the sterile barrier. In some embodiments, one or more splined drive shafts can engage and turn corresponding pulleys in the plate that serves as the sterile barrier. Each hub can have a sterile pulley that is configured to receive a sterile splined shaft from the sterile barrier plate. Rotation of the splined drive shaft can turn the pulley in the sterile barrier plate which can in turn, turn the sterile pulley in the hub via the sterile splined shaft.

It will be understood by one having skill in the art that any embodiment as described herein may be modified to incorporate a mechanical coupling mechanism, for example, as shown in FIG. 19.

In certain embodiments, the interventional devices described herein (e.g., insert or access catheter 2902, procedure catheter 2904, guide catheter 2906, and/or guidewire 2907) may be manually driven, robotically driven, or a combination of both manually and robotically driven interventional devices, as will be appreciated by those of skill in the art in view of the disclosure herein. For example, the procedures described herein may be performed by manually driving the interventional devices of an interventional device assembly (e.g., interventional device assembly 2900), robotically driving the interventional devices of the interventional device assembly, or both manually and robotically driving the interventional devices of the interventional device assembly.

In certain embodiments, a first subset of interventional devices of an interventional device assembly (e.g., interventional device assembly 2900) is driven robotically during a surgical procedure and a second subset of the interventional devices is driven manually during the surgical procedure. In certain embodiments, one or more interventional devices of an interventional device assembly (e.g., interventional device assembly 2900) can be driven robotically during a portion of a surgical procedure and driven manually during another portion of the surgical procedure.

For example, in certain embodiments, a second subset of interventional devices is detachably coupled to a robotically driven first subset of interventional devices. The second subset of interventional devices may be driven by the first subset of interventional devices during a portion of a neurovascular procedure while the second subset of interventional devices is coupled to the first subset of interventional devices. One or more interventional devices of the second subset of interventional devices may be detached from the first subset of interventional devices and manually driven during another portion of the neurovascular procedure.

Figure 25:
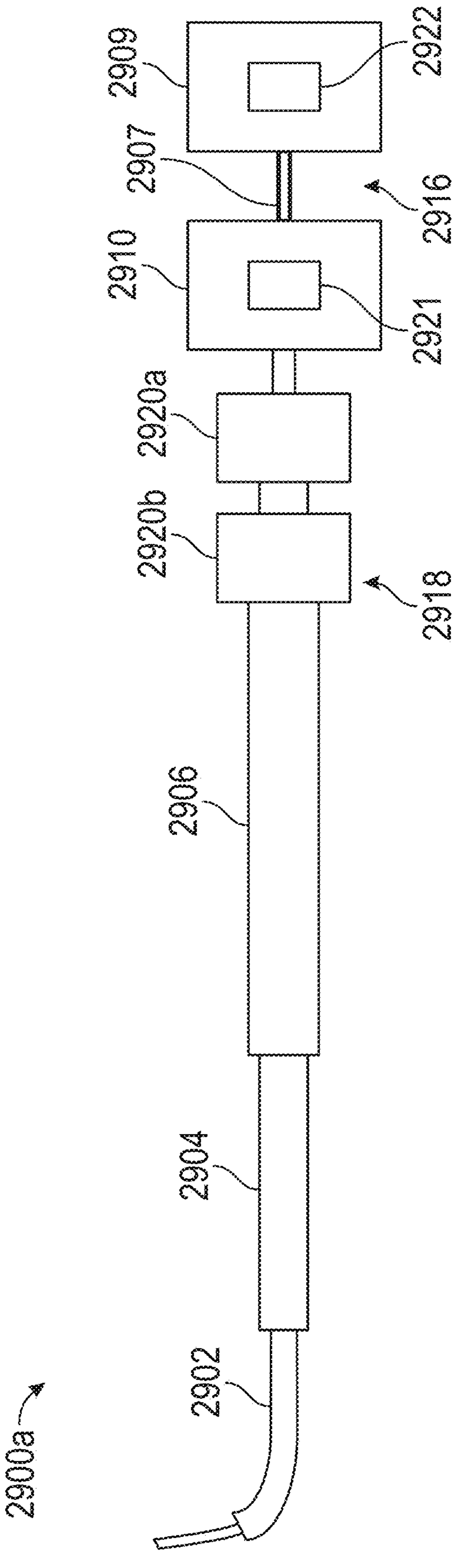
FIG. 25 depicts a side schematic view of an interventional device assembly for supra-aortic access and neurovascular procedures.

FIG. 25 illustrates a side schematic view of a multi catheter interventional device assembly **2900*a* for combined supra-aortic access and/or neurovascular site access and procedure (e.g., aspiration), as described herein. The interventional device assembly 2900*a* may include any of the same or similar features or functions as the interventional device assembly 2900**.

The interventional device assembly **2900*a* includes a robotically driven subset 2916 of interventional devices and a manually driven subset 2918 of interventional devices. The manually driven subset 2918 can be detachably coupled to the robotically driven subset 2916 by one or more coupling mechanisms 2920*a* and 2920*b*. The one or more coupling mechanisms 2920***a* and 2920*b* can be luer locks, hemostatic valves, fasteners, complementary threaded coupling members, or any other suitable coupling mechanisms.

In certain embodiments, the interventional devices of the manually driven subset 2918 can be robotically driven while coupled to the robotically driven subset 2916 and manually driven when uncoupled from the robotically driven subset 2916. In other words, the interventional devices of the manually driven subset 2918 can be coupled to one or more interventional devices of the robotically driven subset 2916 such that movement of the one or more interventional devices of the robotically driven subset 2916 causes corresponding movement of the interventional devices of the manually driven subset 2918.

In certain embodiments, the relative position of the interventional devices of the manually driven subset 2918 may be fixed relative to at least one interventional device of the robotically driven subset 2916 when coupled thereto, such that movement of the at least one interventional device of the robotically driven subset 2916 can drive movement of the interventional devices of the manually driven subset 2918 without a change in relative position.

In certain embodiments, when the manually driven subset 2918 is uncoupled from the robotically driven subset 2916, the interventional devices of the manually driven subset 2918 and the interventional devices of the robotically driven subset 2916 can be driven independently of one another. The interventional devices of the manually driven subset 2918 can be driven manually while the interventional devices of the robotically driven subset 2916 can be driven robotically.

As shown in FIG. 25, in certain embodiments, the interventional device assembly 2900*a* includes an insert or access catheter 2902, a procedure catheter 2904, a guide catheter 2906, and a guidewire 2907. Other components are possible including, but not limited to, one or more guide catheters, an access sheath and/or one or more other procedure catheters and/or associated catheter (control) hubs. In some embodiments, the assembly 2900*a* may also be configured with an optional deflection control for controlling deflection of one or more interventional devices of assembly 2900*a*.

In certain embodiments, the robotically driven subset 2916 can include the access catheter 2902 and the guidewire 2907. The interventional device assembly 2900*a* can include a guidewire hub 2909 and an insert or access catheter hub 2910. The guidewire hub 2909 and access catheter hub 2910 can be used for robotically driving the guidewire 2907 and access catheter 2902, respectively, during a neurovascular procedure, as described herein. In some embodiments, as described herein with respect to FIGS. 26A-26B, the hubs of the assembly 2900*a* (e.g., guidewire hub 2909 and access catheter hub 2910) can instead be hub assemblies having detachable hubs removably coupled to mounts.

In certain embodiments, the manually driven subset 2918 can include the procedure catheter 2904 and the guide catheter 2906.

In some embodiments, the procedure catheter 2904 can be detachably coupled to the robotically driven subset 2916 via the coupling mechanism 2920*a*. For example, the procedure catheter 2904 can be detachably coupled directly to the access catheter 2902 or the access catheter hub 2910 via the coupling mechanism 2920*a*. In certain embodiments, the coupling mechanism 2920*a* can be a luer lock, a hemostatic valve, a fastener, complementary threaded coupling members, or any other suitable coupling mechanism.

In some embodiments, the guide catheter 2906 can be detachably coupled to the robotically driven subset 2916 via the coupling mechanism 2920*b*. In some embodiments, the guide catheter 2906 can be detachably coupled directly to the access catheter hub 2910 via the coupling mechanism 2920*b*. In other embodiments, the guide catheter 2906 can be detachably coupled to the robotically driven subset 2916 indirectly via a detachable coupling to the procedure catheter 2904 or the coupling mechanism 2920*a* while the procedure catheter 2904 is detachably coupled to the robotically driven subset 2916. In certain embodiments, the coupling mechanism 2920*b* can be a luer lock, a hemostatic valve, a fastener, complementary threaded coupling members, or any other suitable coupling mechanism.

In some embodiments, the procedure catheter 2904 and the guide catheter 2906 can both be detachably coupled to the robotically driven subset 2916 via a single coupling mechanism (e.g., coupling mechanism 2920*a* or coupling mechanism 2920*b*).

In certain embodiments, when the procedure catheter 2904 and guide catheter 2906 are coupled to the robotically driven subset, the access catheter 2902 can extend distally beyond the procedure catheter 2904 and the guide catheter 2906 and the procedure catheter 2904 can extend distally beyond the guide catheter 2906, as shown in FIG. 25.

As described herein, the relative position of the interventional devices of the manually driven subset 2918 may be fixed relative to an interventional device of the robotically driven subset 2916 when connected thereto. For example, when the procedure catheter 2904 and/or guide catheter 2906 are coupled (e.g., directly or indirectly) to the access catheter 2902, the relative position(s) of the procedure catheter 2904 and/or guide catheter 2906 may be fixed relative to the access catheter 2902 as the access catheter 2902 is robotically driven.

In certain embodiments, interventional devices of the manually driven subset 2918 (e.g., the procedure catheter 2904 and guide catheter 2906) can be independently uncoupled from the robotically driven subset 2916. For example, in certain embodiments, the guide catheter 2906 can be uncoupled from the robotically driven subset 2916 while the procedure catheter 2904 remains coupled to the robotically driven subset 2916 or vice versa. In certain embodiments, the interventional devices of the manually driven subset 2918 (e.g., the procedure catheter 2904 and guide catheter 2906) can be manually driven together or independently manually driven.

The interventional device assembly 2900*a* can be used to perform a vascular procedure, (e.g., neurovascular procedure) as described herein. In certain embodiments, the interventional device assembly 2900*a* can be robotically driven to achieve supra-aortic access while the manually driven subset 2918 is coupled to the robotically driven subset 2916.

Once access above the aortic arch has been achieved, the interventional device assembly 2900*a* may be robotically driven to position the guidewire 2907 and/or access catheter 2902 to provide access to a particular site (e.g., a clot site, a surgical site, a procedure site, etc.) while the manually driven subset 2918 is coupled to the robotically driven subset 2916. For example, in some embodiments, the interventional device assembly 2900*a* may be robotically driven to position the guidewire 2907 and/or access catheter 2902 within distal cervical/petrous sections of the anatomy. In certain embodiments (for example, in a procedure for removing a clot in the middle cerebral artery), the interventional device assembly 2900*a* may be robotically driven so that the guidewire 2907 and/or access catheter 2902 extend into the middle cerebral artery.

After the guidewire 2907 and/or access catheter 2902 are positioned to provide access to the site, the procedure catheter 2904 and/or the guide catheter 2906 can be uncoupled from the robotically driven subset 2916.

After uncoupling, the procedure catheter 2904 and/or the guide catheter 2906 can be advanced manually towards the site (e.g., the clot site, surgical site, procedure site, etc.). For example, when the site is a clot site, the procedure catheter 2904 and/or guide catheter 2906 can be advanced manually to traverse a face of the clot.

In some embodiments, the procedure catheter 2904 and/or the guide catheter 2906 can be uncoupled from the robotically driven subset 2916 while their distal ends are positioned within the neck of a patient (i.e., proximal to the intracranial vessels). The procedure catheter 2904 and/or the guide catheter 2906 can then be manually advanced into the intracranial vessels of the patient. In some embodiments, the procedure catheter 2904 and/or guide catheter 2906 can be driven robotically within the cervical carotid. The procedure catheter and/or guide catheter can be driven manually distally beyond the cervical carotid.

In some embodiments, only the procedure catheter 2904 is advanced to the site. In other embodiments, the both the procedure catheter 2904 and the guide catheter 2906 are advanced to the site. The procedure catheter 2904 and the guide catheter 2906 can be manually advanced to the site together or separately.

After the procedure catheter 2904 and the guide catheter 2906 are advanced to the site, a treatment may be performed, such as, for example, aspiration of a clot. In certain embodiments, other interventional devices, such as smaller procedure catheters, may also be added and used at the site (e.g., additional aspiration catheters, stent retrievers, etc.).

In certain embodiments, after the procedure catheter 2904 and/or guide catheter 2906 are advanced to the site, one or more of the robotically driven interventional devices (i.e., the guidewire 2907 and/or the access catheter 2902) can be removed from within the procedure catheter 2904 and/or guide catheter 2906. Removal may provide a larger cross-sectional luminal area for clot extraction and/or delivery of additional devices. In some embodiments, the procedure catheter 2904 may also be removed, and the guide catheter 2906 can be used as a procedure catheter, for example, to remove a clot. In other embodiments, the procedure catheter 2904 may be removed and the guide catheter 2906 can be used for delivery of additional interventional devices.

While a robotically driven guidewire 2907, robotically driven access catheter 2902, manually driven procedure catheter 2904, and manually driven guide catheter 2906 are described with respect to FIG. 25, in other embodiments, any of the interventional devices or subset of the interventional devices may be robotically driven and any of the interventional devices or subset of the interventional devices may be manually driven. For example, in some embodiments, a manually driven guidewire 2907 may be used with a robotically driven access catheter 2902, a manually driven procedure catheter 2904, and a manually driven guide catheter 2906.

In certain embodiments, the guide catheter 2906 and procedure catheter 2904 can be robotically driven and the access catheter 2902 and guidewire 2907 can be manually driven. For example, a robotically driven subset 2916 can include the procedure catheter 2904 and the guide catheter 2906 and a manually driven subset 2918 can include the access catheter 2902 and the guidewire 2907. In such embodiments, the guide catheter 2906 and procedure catheter 2904 can be coupled to a robotically controlled guide catheter hub and a robotically controlled procedure catheter hub, respectively.

In some embodiments, the access catheter 2902 can be detachably coupled to the robotically driven subset 2916 via a coupling mechanism (e.g., coupling mechanism 2920*a* or 2920*b*). For example, the access catheter 2902 can be detachably coupled to the procedure catheter hub via a coupling mechanism. In some embodiments, the guidewire 2907 can be detachably coupled to the robotically driven subset 2916 by a coupling mechanism. For example, in some embodiments, the guidewire 2907 can be directly detachably coupled to the procedure catheter hub via a coupling mechanism. In some embodiments, the guidewire 2907 can be detachably coupled to the robotically driven subset 2916 indirectly via a detachable coupling to the access catheter 2902 or a coupling mechanism of the access catheter 2902.

In other embodiments, the manually driven subset 2918 (e.g., a guide catheter and/or a procedure catheter) may not couple to the robotically driven subset 2916. For example, in certain embodiments, the robotically driven subset 2916 may be robotically driven within the vasculature of a patient, and one or more interventional devices may be manually inserted into and advanced within the robotically driven subset 2916 without having been coupled to the robotically driven subset 2916.

Any combination of interventional devices may be part of the robotically driven subset 2916 and manually driven subset 2918. For example, one of the interventional devices (e.g., catheter 2906, catheter 2904, catheter 2902, or guidewire 2907) may be part of the robotically driven subset 2916 and the remaining interventional devices may be part of a manually driven subset 2918 (one or more of which may be coupled, directly or indirectly, to the robotically driven subset 2916). Alternatively, one of the interventional devices (e.g., catheter 2906, catheter 2904, catheter 2902, or guidewire 2907) may be part of a manually driven subset 2918 (which may be coupled, directly or indirectly, to the robotically driven subset 2916), and the remaining interventional devices may be part of robotically driven subset 2916.

In certain embodiments, each of the access catheter 2902, the procedure catheter 2904, the guide catheter 2906, and the guidewire 2907 may be part of the robotically driven subset 2916. In such embodiments, the access catheter 2902, the guidewire 2907, the procedure catheter 2904, and the guide catheter 2906 can be driven robotically.

In certain embodiments, the guide catheter 2906 may be advanced to a desired position within the vasculature (e.g., within a desired ostium as described herein) and maintained in that position (or not further distally advanced beyond that position) to allow one or more additional interventional devices to be driven through the guide catheter 2906 further distally into the vasculature. In some such embodiments, the guide catheter 2906 may be maintained at the same position throughout a procedure or throughout a significant portion of the procedure. In such embodiments, it may be desirable for the guide catheter 2906 to be robotically driven to the desired position within the vasculature. In such embodiments, one or more additional interventional devices may be driven manually and/or robotically through the guide catheter 2906.

While an access catheter 2902, procedure catheter 2904, guide catheter 2906, and guidewire 2907, are described herein with respect to FIG. 25, other interventional devices may be additionally and/or alternatively be used in a procedure. Such devices may be part of a robotically driven subset 2916 or a manually driven subset 2918. For example, in some embodiments, one or more robotically driven interventional devices may be removed from an interventional device assembly, and one or more manually driven interventional device may be inserted into the interventional device assembly.

In some embodiments, additional interventional devices (e.g., a stent retriever, embolic coil, aneurysm coil, coil delivery catheter, and/or an occlusion device) may be inserted within the access catheter 2902, the procedure catheter 2904, and/or the guide catheter 2906 and manually controlled. In some embodiments, the procedure catheter may be a coil delivery catheter. In some such embodiments, one or more of the interventional devices (e.g., the access catheter 2902 and guidewire 2907) may be removed from the interventional device assembly prior to inserting the additional interventional devices. For example, in a stroke environment, a stent retriever and/or stent retriever microcatheter may be manually deployed through the procedure catheter 2904 and/or the guide catheter 2906, for example to retrieve a clot if there is difficulty aspirating the clot.

Additionally, while a guidewire 2907, an access catheter 2902, a procedure catheter 2904, and a guide catheter 2906 are described with respect to FIG. 25, in other embodiments, only a subset of the devices may be used in neurovascular procedure. For example, a neurovascular procedure (or at least a portion of a procedure) may be performed without a guidewire 2907. In some embodiments, only an insert or access catheter 2902 and guidewire 2907 may be used in a procedure (or at least a portion of a procedure). In some embodiments, only a guide catheter 2906 and an insert or access catheter 2902 may be used in a procedure (or at least a portion of a procedure).

While a guidewire 2907, an access catheter 2902, a procedure catheter 2904, and a guide catheter 2906 are described with respect to FIG. 25, other combinations of interventional devices may be used in a partially robotically driven and partially manually driven assembly of interventional devices. For example, a thrombectomy catheter or access sheath may be used instead of a guide catheter 2906. In embodiments in which a thrombectomy catheter is used instead of a guide catheter 2906, the procedure catheter 2904 may be a smaller thrombectomy catheter. In such embodiments (or in other embodiments), the access catheter 2902 may be a microcatheter and the guidewire 2907 may be a microwire.

In certain embodiments, one or more additional interventional devices, which may be any combination of manually driven and/or robotically driven interventional devices, can be added to the interventional device assembly 2900 during a procedure. In certain embodiments, as described herein, one or more interventional devices may be removed from the interventional device assembly 2900 during a procedure, and may in some embodiments be replaced with other interventional devices.

For example, in certain embodiments, a stent retriever may replace the guidewire 2907. The stent retriever may be coupled to the hub 2909 or an alternative drive mechanism (e.g., an additional hub that may replace the hub 2909). The stent retriever may be manually or robotically driven.

In some embodiments, a micro catheter may replace the insert or access catheter 2902. Alternatively, a micro catheter may be inserted through an insert or access catheter 2902. The micro catheter may be coupled to the hub 2910 or an alternative drive mechanism (e.g., an additional hub that may replace the hub 2910). The micro catheter may be manually or robotically driven.

Other interventional devices including coils, wires, implants (stent, flow diverter, intrasaccular device), etc., may also be added to the interventional device assembly during the procedure. Any of these devices may be manually or robotically driven.

While a detachably coupled manually driven subset 2918 of interventional devices is shown in FIG. 25, in some embodiments, one or more manually driven interventional devices may not be coupled with the robotically driven interventional devices at the beginning of a procedure, but may instead be introduced during the procedure. For example, in some embodiments, a procedure may begin using one or more robotically driven interventional devices (e.g., an assembly of robotically driven interventional devices). At a later time during the procedure, one or more manually driven interventional devices may be introduced (e.g., through the one or more robotically driven interventional devices). The one or more manually driven interventional devices may at least at first be manipulated manually. After introduction, the one or more manually driven interventional devices may be coupled to the one or more robotically driven interventional devices and driven robotically via the one or more robotically driven interventional devices. In other embodiments, the one or more manually driven interventional devices may not couple to the one or more robotically driven interventional devices, and may instead remain independently manually movable.

While a detachably coupled manually driven subset 2918 of interventional devices is shown in FIG. 25, in some embodiments, one or more interventional devices may be operated in a manually driven mode without detaching the interventional devices from a hub. In some embodiments, any of the robotically driven interventional devices described herein may be selectively operated in a manual mode. In addition, the hub can be removed from the hub assembly and manipulated manually. For example, in some embodiments, an actuator, such as a button or switch 2921, may be operated to allow for manual movement of an interventional device and/or its corresponding hub. The actuator may be positioned on the hub, on the interventional device, on the drive table, or in another location adjacent the interventional device assembly 2900 or 2900*a*. In certain embodiments, in addition or alternatively to an actuator, resistance sensing can be used to determine that a user is attempting to manually move an interventional device and/or hub, and may allow for manual movement of the interventional device and/or hub if a resistance sensor detects a value exceeding a threshold value.

In certain embodiments, one or more of the interventional devices and/or hubs may be robotically operated by a control positioned to allow a user to manually move another interventional device while operating the control. For example, one or more of the hubs may include a control, such as a joystick or toggle switch 2922, that can be operated by a user with one hand (either left or right) to cause robotically driven movement of the corresponding interventional device while the user manually manipulates another interventional device with the other hand (either left or right). Such a configuration may allow a user to robotically control interventional devices while positioned in close enough proximity to manually control other interventional devices (for example, instead of robotically controlling interventional devices from a console remote from the patient). Such a configuration may also provide redundancy to allow robotic control of an interventional device in the event of a disruption of communication with the remote console.

In certain embodiments, one or more interventional devices (e.g., within the robotically driven subset 2916 and the manually driven subset 2918) can transition from being robotically driven to being manually driven during a procedure. In certain embodiments, one or more interventional devices can transition from being manually driven to being robotically driven during a procedure. For example, one or more of the interventional devices initially part of the robotically driven subset 2916 can transition to part of the manually driven subset 2918. Accordingly, the one or more interventional devices can be robotically driven during initialization and transition to manual control after the one or more interventional devices are initially positioned. Additionally and/or alternatively, one or more of the interventional devices initially part of the manually driven subset 2918 can transition to part of the robotically driven subset 2916. Accordingly, the one or more interventional devices can be manually driven during initialization and transition to robotic control after the one or more interventional devices are initially positioned. In some embodiments, the procedure may transition from a fully robotic procedure to a fully manual procedure or vice versa.

In some embodiments, one or more interventional devices may transition from being robotically driven to being manually driven by physically detaching the interventional device from the robotic drive system. An interventional device can be detached from the robotic drive system while a portion of the interventional device remains positioned within the vasculature of the patient.

The one or more detached interventional devices may be provided to a different working surface. For example, one or more interventional devices may be detached from the drive table and moved to a different working surface (e.g., on a patient's leg). Detaching and moving the interventional devices may advantageously provide greater ergonomic support for the physician and/or provide control to the physician at a location more natural for and/or customarily used by the physician for similar manual procedures.

In certain embodiments, detaching the one or more interventional devices may also advantageously allow for deploying additional and/or alternative interventional devices (e.g., a stent retriever, embolic coil, aneurysm coil, and/or an occlusion device) through the detached interventional devices for manual driving at a position offset from other components on the drive table (e.g., if there is not sufficient working space on the drive table). For example, in certain embodiments, a robotically driven guidewire 2907 and a robotically driven access catheter 2902 can be withdrawn from a robotically driven procedure catheter 2904 and a robotically driven guide catheter 2906. In some embodiments, the robotically drive procedure catheter 2904 and robotically driven guide catheter 2906 can be detached from the robotic drive table for manual use and positioned on a different working surface. One or more additional interventional devices may then be advanced through the procedure catheter 2904 and guide catheter 2906 into the vasculature at a position offset from the position of the withdrawn guidewire 2907 and access catheter 2902.

In certain embodiments, detaching one or more interventional devices may advantageously allow for an alternative mechanism for driving the interventional devices in the event of malfunction of the robotic drive system.

Figure 26A:
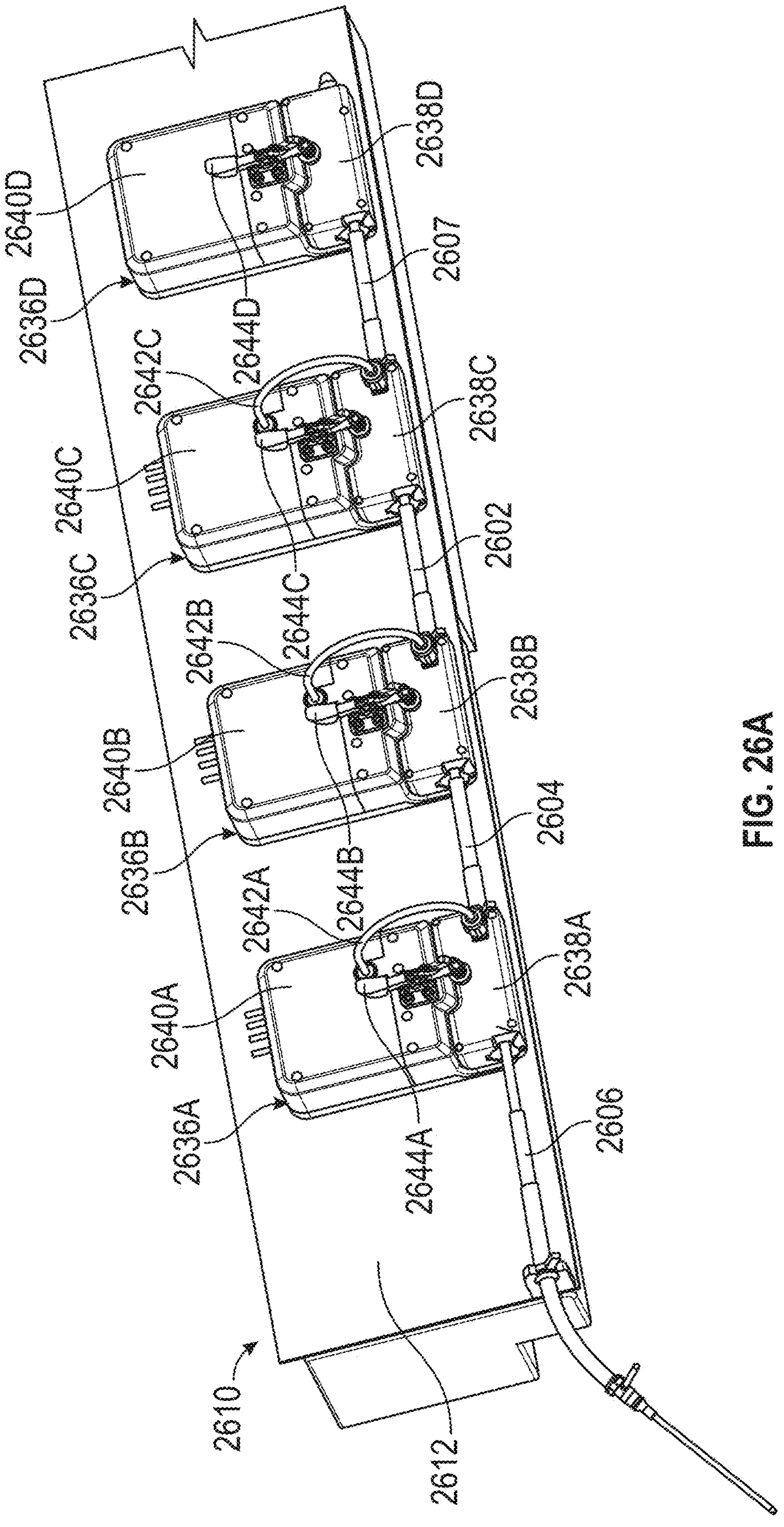
FIG. 26A shows a perspective view of a hybrid system.
Figure 26B:
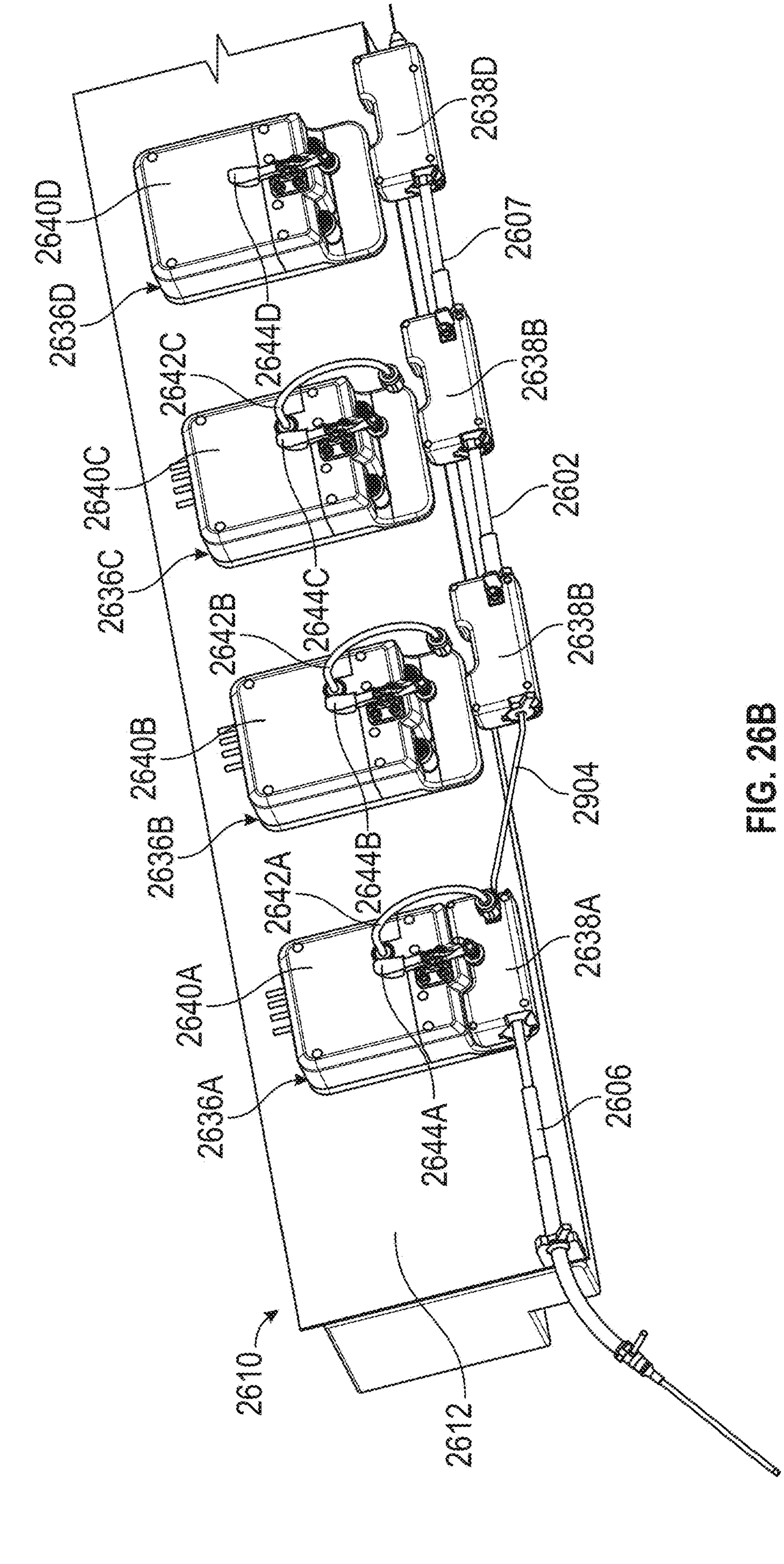
FIG. 26B shows a perspective view of a hybrid system.

One embodiment of an interventional device assembly in which interventional devices can be detached from the robotic drive table is shown in FIGS. 26A-26B.

Certain embodiments of hubs described herein, such as hub 36, include a housing (e.g., housing 38) for coupling an interventional device thereto, components (e.g., roller 53 and 55) for directly coupling to and moving along a drive table 2610, and magnet(s) (e.g., magnet 69) for magnetically coupling to a hub adapter across a sterile barrier. In other embodiments, as shown in FIGS. 26A-26B, a first subassembly or hub (e.g., first subassembly or hub 2638A, first subassembly or hub 2638B, first subassembly or hub 2638C, first subassembly or hub 2638D) configured to couple to and house an interventional device may be removably attachable to a second subassembly or mount (e.g., second subassembly or mount 2640A, second subassembly or mount 2640B, second subassembly or mount 2640C, second subassembly or mount 2640D) configured to magnetically couple to a hub adapter across a sterile barrier and move along a drive table 2610. Such a hub and mount may together form a hub assembly (e.g., hub assembly 2636A, hub assembly 2636B, hub assembly 2636C, hub assembly 2636D). In some embodiments, the mount may be a magnetically driven member, an axially driven member, a puck, a slider, a shuttle, or a stage.

One or more of the hubs 2638A-D can include a valve, such as a hemostasis valve, to allow interventional devices to advance therethrough. For example, in certain embodiments, the hub 2638A can include a hemostasis valve to allow one or more interventional devices coupled to hubs 2638B-D to advance therethrough to facilitate concentric arrangement of the interventional devices.

FIGS. 26A-26B illustrate a plurality of hub assemblies, each hub assembly connected to a corresponding interventional device. The plurality of hub assemblies can include a first hub assembly 2636A having a first hub 2638A and a first mount 2640A, a second hub assembly 2636B having a second hub 2638B and a second mount 2640B, a third hub assembly 2636C having a third hub 2638C and a third mount 2640C, and a fourth hub assembly 2636D having a fourth hub 2638D and a fourth mount 2640D.

In certain embodiments, the first hub 2638A can be coupled to a guide catheter. In certain embodiments, the second hub 2638B can be coupled to a procedure catheter. In certain embodiments, the third hub 2638C can be coupled to an access catheter. In certain embodiments, the fourth hub 2638D can be coupled to a guidewire.

Such hub assemblies 2636A-D may allow for a hub 2638A-D to be removed from a mount 2640A-D, for example, so that a different hub can be coupled to the same mount 2640A-D. In some embodiments, a manually driven interventional device can be coupled to the same mount 2640A-D so that it can be robotically driven. In other embodiments, mount 2640A-D may initially have no interventional device coupled thereto and a manually driven interventional device can be coupled to the mount 2640A-D so that it may be robotically driven. Such an arrangement can allow for the replacement of a hub 2638A-D with a different hub having a different interventional device coupled thereto without breaking a magnetic connection with a hub adapter. For example, such an arrangement may allow for a hub 2638C coupled to an access catheter to be removed from a mount 2640C and replaced with a hub coupled to a procedure catheter without breaking a magnetic connection with a hub adapter.

In some embodiments, a hub 2638A-D can be removed from a first mount 2640A-D and coupled to a second mount 2640A-D that is distal or proximal to the first mount, for example, to provide a different set of interventional devices or different arrangement of interventional devices for a portion of a procedure in comparison to a previous portion of the procedure.

For example, in some embodiments, an access assembly of interventional devices may be coupled to the drive table 2610 for a first part of a medical procedure and a procedure assembly of interventional devices can be coupled to the drive table 2610 for a second part of the medical procedure. In some embodiments, a hub 2638A coupled to a guide catheter can be coupled to mount 2640A, a hub 2638B coupled to an insert or access catheter (e.g., a 5 Fr insert or access catheter) can be coupled to mount 2640B, and a hub 2638C coupled to a guidewire (e.g., a guidewire having a 0.035 in diameter) can be coupled to mount 2640C and used to achieve supra-aortic access. While achieving supra-aortic access, the mount 2640D may have no hub coupled thereto. After supra-aortic access is achieved, the hub 2638B and hub 2638C may be removed. Subsequently, a hub coupled to a procedure catheter can be coupled to mount 2640B, a hub coupled to an insert or access catheter (e.g., an access catheter having an inner diameter of 0.035 in) can be coupled to the mount 2640C, and a hub coupled to a guidewire (e.g., a microwire having a diameter of 0.014 in) can be coupled to the mount 2640D, and a procedure, such as aspiration of a clot, may be performed.

In some embodiments, for example when performing a thrombectomy on a distal, medium vessel occlusion (DMVO), it may not be possible to reach the clot with certain procedure catheters, such as a procedure catheter having a 0.071 inch inner diameter). In such embodiments, a catheter having a smaller outer diameter may be used to reach and aspirate the clot. For example, when an initial arrangement of interventional devices includes a first hub 2638A coupled to a guide catheter, a second hub 2638B coupled to a procedure catheter, a third hub 2638C coupled to an access catheter (e.g., a 5 Fr access catheter), and a fourth hub 2638D coupled to a guidewire, the hub 2638C may be removed and replaced with a hub coupled to a smaller catheter (e.g., a 0.035 inch inner diameter catheter) to navigate to (e.g., through the procedure catheter) and aspirate the clot. In other embodiments, the smaller catheter may instead to navigated to the clot manually.

In some embodiments, hub assemblies 2636A-D may allow for a hub 2638A-D to be removed from a mount 2640A-D to facilitate performance of a procedure through the hub assemblies 2636A-D having hubs 2638A-D coupled to mounts 2640A-D (e.g., by providing more working space along the drive table 2610). For example, as described herein, in certain embodiments, an access catheter and/or guidewire can be withdrawn from a procedure catheter prior to aspiration using the procedure catheter. In certain embodiments, the access catheter hub 2638C and/or guidewire hub 2638D can be removed from their respective mounts 2640C and 2640D before, after, or while withdrawing the access catheter and/or guidewire from the procedure catheter prior to aspiration using the procedure catheter. In some such embodiments, the guide catheter hub 2638A and procedure catheter hub 2638B may remain coupled to their respective mounts 2640A and 2640B. In other embodiments, the procedure catheter hub 2638B or the procedure catheter hub 2638B and the guide catheter hub 2638A can be uncoupled from their respective mounts 2640A and 2640B prior to performing the aspiration procedure.

In some embodiments, hub assemblies 2636A-D may allow for a hub 2638A-D to be removed from a mount 2640A-D to facilitate a path for one or more manual devices to be inserted through a more distal hub assembly. For example, in some embodiments, when an initial arrangement of interventional devices includes a first hub 2638A coupled to a guide catheter, a second hub 2638B coupled to a procedure catheter, a third hub coupled to an access catheter, and a fourth hub 2638D coupled to a guidewire, the hub 2638B, hub 2638C, and hub 2638D can be removed. Following removal, a stent may be manually navigated through the guide catheter for manual tandem lesion stent placement. In some such embodiments, the stent is navigated through the guide catheter while the hub 2638A is coupled to the mount 2640A. In other embodiments, the hub 2638A may be removed from the mount 2640A while the guide catheter is positioned within the vasculature of the patient, and the stent can then be navigated through the guide catheter.

Alternatively, one or more of the hub assemblies 2636A-D can be moved proximally towards a proximal end of a drive table 2610 to withdraw their corresponding interventional devices to facilitate a path for one or more manual devices to be inserted through a more distal hub assembly.

In some embodiments, hub assemblies 2636A-D may allow for a hub 2638A-D to be removed from a mount 2640A-D so that the hub 2638A-D may be used separately from the mount 2640A-D (e.g., for a manual procedure). Such an arrangement may allow for a hub 2638A-D to be removed from a magnetically driven mount 2640A-D so that the hub 2638A-D can be used manually during a medical procedure (e.g., manually manipulated by a user to advance, retract, and/or rotate the hub 2638A-D and coupled interventional device).

In some embodiments, an interventional device may be driven robotically for a portion of a procedure and manually for another portion of a procedure. For example, as shown in FIG. 26A, in some embodiments, one or more of the hubs 2638A-2638D can be coupled to and physically connected with a corresponding mount 2640A-2640D, during at least a portion of a procedure. As further illustrated in FIG. 26A, the interventional devices may be in a stacked and/or nested arrangement.

In some embodiments, a subset of the plurality of interventional devices may be driven manually by disconnecting one or more of the hubs 2638A-2638D from their respective mounts 2640A-2640D during a portion of a procedure. For example, FIG. 26B depicts hub 2638A coupled to the mount 2640A, hub 2638B disconnected from mount 2640B, hub 2638C disconnected from mount 2640C, and hub 2638D disconnected from mount 2640D.

In certain embodiments, a plurality of interventional devices can be robotically driven to a desired position within the vasculature of a patient during a first portion of a procedure (e.g., via a coupling between their respective hubs 2638A-D and robotically driven mounts 2640A-D). Subsequently, all of the interventional devices or a subset of the interventional devices can be decoupled from robotic drive system by disconnecting their respective hubs 2638A-D from their respective mounts 2640A-D while portions of the interventional devices are positioned within the vasculature of the patient. For example, in certain embodiments, a plurality of interventional devices can be robotically driven to achieve supra-aortic access. After supra-aortic access is achieved all or a subset of the interventional devices can be decoupled from the robotic drive system by disconnecting their respective hubs 2638A-D from their respective mounts 2640A-D, and additional procedure steps may be performed manually.

For example, in certain embodiments, a hub assembly 2636A having a hub 2638A coupled to a guide catheter 2906, a hub assembly 2636B having a hub 2638B coupled to a procedure catheter 2904, a hub assembly 2636C having a hub 2638C coupled to an access catheter 2902, and a hub assembly 2636D having a hub 2638D coupled to a guidewire 2907 can be driven until supra-aortic access is achieved, and the guide catheter 2906 is positioned within a desired ostium. Subsequently, one or more of the hub 2638B, the hub 2638C, and the hub 2638D can be decoupled from its respective mount 2640B, 2640C, and 2640D, so that one or more of the procedure catheter 2904, the access catheter 2902, and the guidewire 2907 can be used to perform additional steps of the procedure manually as shown in FIG. 26B. For example, one or more of the procedure catheter 2904, the access catheter 2902, and the guidewire 2907 can be manually advanced further distally in the anatomy. In other embodiments, for example, the access catheter 2902 and guidewire 2907 can be withdrawn for the procedure catheter 2904, before or after detachment of the hub 2638B from its mount 2640B, and one or more additional manual interventional devices, such as a stent retriever and/or a stent retriever delivery microcatheter, can be inserted into the procedure catheter to perform additional steps of a procedure manually.

In other embodiments, the hub 2638A can be detached from the mount 2640A either by itself (e.g., after withdrawal of the procedure catheter 2904, access catheter 2902, and guidewire 2907 from the guide catheter 2906) or in addition to detachment of the hub 2638B from the mount 2640B (or detachment of additional hubs from their respective mounts) for performing additional procedure steps manually (e.g., by manually manipulating the hub 2638A and/or by inserting additional manual interventional devices through hub 2638A and the guide catheter 2906).

As further illustrated in FIG. 26B, one or more interventional devices may remain in a stacked and/or nested configuration after being decoupled. Portions of the interventional devices may remain within the vasculature and/or within the lumens of adjacent interventional devices while being decoupled from the robotic drive system.

The hubs 2638A-2638D may include surfaces configured to both be supported and manipulated by a corresponding mount 2640A-2640D and/or by a human operator. Accordingly, when the one or more hubs 2638A-D are decoupled from a corresponding one or more mounts 2640A-D, the corresponding one or more interventional devices may be positioned and movable within the patient's body by manual manipulation of the hubs 2638A-2638D (e.g., by a user grasping, rotating, and/or axially moving the hubs).

In some embodiments, as shown in FIG. 26A, each hub 2638A-C may be in fluid communication with a corresponding mount 2640A-C via a conduit 2642A-C. Each mount 2640A-C may be in communication with a fluidics system, which may provide fluids (e.g., saline, contrast, and/or therapeutic agents) and/or vacuum. The conduit 2642A-C can connect the catheters coupled to the hubs 2638A-C with the fluidics system to provide fluids or vacuum to the catheters.

In some embodiments, the conduit 2642A-C may remain connected to its corresponding hub 2638A-C during manual control. In some embodiments, the conduits 2642A-D may have a sufficient length to advantageously provide flexibility for the physician to manually control the hubs 2638A-C away from the corresponding mounts 2640A-C. In some embodiments, monitoring and mitigating bubbles and/or air pockets within the fluidics system may be difficult with longer conduits 2642A-C. The conduit 2642A-C may be between 6 inches and 24 inches in length. For example, the conduit 2642 can be 6 inches, 7 inches, 8 inches, 9 inches, 10 inches, 11 inches, 12 inches, 13 inches, 14 inches, 15 inches, 16 inches, 17 inches, 18 inches, 19 inches, 20 inches, 21 inches, 22 inches, 23 inches, or 24 inches, or any intermediate lengths. In such embodiments, the conduit 2642A-C may be sufficiently long to enable a physician to manually control the one or more hubs 2638A-C away from the corresponding mounts 2640A-C while monitoring and mitigating bubbles.

In some embodiments, one or more of the conduit 2642A-C may be uncoupled from its corresponding hub 2638A-C. In some such embodiments, the hub 2638 may be coupled to the fluidics system using an alternative connection (e.g., an alternative conduit or tubing set). In some embodiments, the hub 2638A-C may be fluidly connected to a secondary fluidics source. For example, the hub 2638A-C may be fluidly connected to a saline and/or contrast bag or other fluid source. In some embodiments, the secondary fluidics source can be a gravity fed or pressurized fluidics bag. In some embodiments, the hub 2638A-C can be coupled to a vacuum source, such as a syringe for aspiration. In some embodiments, the fluidics may be connected through a T-connector. The T-connector can be in fluid communication with a saline and/or contrast bag and/or an aspiration source. For example, the T-connector can fluidly connect the one or more detached interventional devices to a syringe.

In some embodiments, one or more hubs 2638A-D may remain coupled to the its corresponding mount 2640A-D during an entirety of a procedure. This may advantageously allow the physician to maintain a connection between an interventional device of the hub remaining coupled to its corresponding mount and the fluidics system (e.g., via conduit 2642A) throughout the duration of the procedure. This may be advantageous in procedures in which an interventional device can be robotically driven to a particular position and further movement of the interventional device is not desired throughout remaining portions of the procedure. For example, in some embodiments the hub 2638A coupled to the guide catheter 2906 can be driven to achieve supra-aortic access. Further distal movement of the guide catheter may not be required in the procedure. In such embodiments, the hub 2638A may remain robotically attached to the mount 2640A for the duration of the procedure. This may advantageously allow the physician to maintain a connection between the guide catheter 2906 and the fluidics system (e.g., via conduit 2642A) throughout the duration of the procedure.

As shown in FIGS. 26A-26B, in certain embodiments, an interventional device assembly 2600 may include a plurality of hub assemblies. In some embodiments, the plurality of hub assemblies may include a first hub assembly 2636A, a second hub assembly 2636B, a third hub assembly 2636C, and a fourth hub assembly 2636D. Each of the plurality of hub assemblies can include a corresponding first subassembly or hub 2638A-D, a corresponding second subassembly or mount 2640A-D, and one or more anti-buckling devices 2602, 2604, 2606, and 2607, which may be in the form of telescoping tubes. The one or more anti-buckling devices 2602, 2604, 2606, and 2607 may provide support to one or more interventional devices extending between the one or more hub assemblies.

In some embodiments, a first anti-buckling device 2606 can extend from the hub 2638A of the first hub assembly 2636A to a distal support at a distal portion of the drive table 2610 having a support surface 2612. The first anti-buckling device 2606 may be removably coupled to the distal support to allow for uncoupling of the first anti-buckling device before uncoupling the hub 2638A from the mount 2640A of the first hub assembly 2636A.

A second anti-buckling device 2604 can extend between the hub 2638B of the second hub assembly 2636B and the hub 2638A and can be removably coupled to the hub 2638A. In some embodiments, if uncoupling of the hub 2638A from the mount 2640A is desired, but not uncoupling of the hub 2638B from its mount 2640B, the second anti-buckling device 2604 may be uncoupled from the hub 2638A prior to uncoupling the hub 2638A from the mount 2640A. In other embodiments, if both the hub 2638A and the hub 2638B are uncoupled from their respective mounts, the second anti-buckling device 2604 may remain coupled to the hub 2638A. In some embodiments, the second anti-buckling device 2604 may be uncoupled from the hub 2638A before uncoupling the hub 2638B from the mount 2640B if the hub 2638A is not also being uncoupled from its mount 2640A (as shown, for example, in FIG. 26B). FIG. 26B illustrates the second anti-buckling device 2604 retracted and/or disengaged from the hub 2638B. The hub 2638B can be removed from its mount 2640B while the procedure catheter 2904 is positioned within the guide catheter 2906.

A third anti-buckling device 2602 can extend between the hub 2638C of the third hub assembly 2636C and the hub 2638B and can be removably coupled to the hub 2638B. In some embodiments, if uncoupling of the hub 2638B from the mount 2640B is desired, but not uncoupling of the hub 2638C from its mount 2640C, the third anti-buckling device 2602 may be uncoupled from the hub 2638B prior to uncoupling the hub 2638B from the mount 2640B. In other embodiments, if both the hub 2638B and the hub 2638C are uncoupled from their respective mounts, the third anti-buckling device 2602 may remain coupled to the hub 2638B (as shown, for example, in FIG. 26B). In some embodiments, the third anti-buckling device 2602 may be uncoupled from the hub 2638B before uncoupling the hub 2638C from the mount 2640C if the hub 2638B is not also being uncoupled from its mount 2640B.

A fourth anti-buckling device 2607 can extend between the hub 2638D of the fourth hub assembly 2636D and the hub 2638C and can be removably coupled to the hub 2638C. In some embodiments, if uncoupling of the hub 2638C from the mount 2640C is desired, but not uncoupling of the hub 2638D from its mount 2640D, the fourth anti-buckling device 2607 may be uncoupled from the hub 2638C prior to uncoupling the hub 2638C from the mount 2640C. In other embodiments, if both the hub 2638C and the hub 2638D are uncoupled from their respective mounts, the fourth anti-buckling device 2607 may remain coupled to the hub 2638C (as shown, for example, in FIG. 26B). In some embodiments, the anti-buckling device 2607 may be uncoupled from the hub 2638C before uncoupling the hub 2638D from the mount 2640D if the hub 2638C is not also being uncoupled from its mount 2640C.

In certain embodiments, as shown in FIGS. 26A-26B, the hubs 2638A-D may be removably secured to the mounts 2640A-D using clamp mechanisms 2644A-D.

In certain embodiments, one or more hub assemblies having removable hubs coupled to mounts can be used in an embodiment in which one or more manual interventional device are connected (directly or indirectly) to an adjacent interventional device or adjacent interventional device hub as described, for example, with respect to FIG. 25. For example, in certain embodiments, one or both of the hubs 2910 and 2909 can be a hub assembly having a removable hub coupled to a mount. In such embodiments, the interventional devices of the manually driven subset 2918 can be coupled by one or more coupling mechanisms (e.g., 2920*a* and 2920*b*), directly or indirectly, to the hub, mount, and/or interventional device of one of the hub assemblies. In such embodiments, manual movement of an interventional device may be provided by decoupling a hub of a hub assembly from its corresponding mount or by decoupling an interventional device of the manually driven subset 2918 from an adjacent hub assembly.

The interventional device assembly 2600 of FIGS. 26A-26B may have any of the same or similar features and/or functions as the assembly of FIG. 25 and vice versa. For example, when one or more of the hubs 2638A-D are disconnected from their respective mounts 2640A-D, the hubs 2638A-D and their corresponding interventional devices may be manually manipulated to perform the same or similar procedure steps as described with respect to the interventional devices of the manually driven subset 2918 when uncoupled from the robotically drive subset and vice versa.

In certain embodiments, an interventional device assembly having robotically driven and manually driven interventional devices can allow for robotic driving of interventional devices to a particular location in the anatomy and manual driving of interventional devices beyond that particular location. For example, in some embodiments, one or more interventional devices can be robotically driven proximal to and within the cervical carotid. The same or different interventional devices may then be manually driven distally beyond the cervical carotid. In certain embodiments, an interventional device assembly having robotically driven interventional devices and manually driven interventional devices can allow for performance of neurovascular procedure by multiple physicians and/or technicians. For example, a first physician or technician may robotically drive the robotically driven interventional devices while a second physician or technician may manually drive the manually driven interventional devices. In certain embodiments, a remote physician or technician may perform a robotically driven portion of a procedure while a bedside physician or technician may perform a manual portion of the procedure.

While use of an interventional device assembly having robotically driven interventional devices and manually driven interventional devices for performing neurovascular procedures is described, the interventional device assemblies having robotically driven interventional devices and manually driven interventional devices described herein may be used to perform a wide variety of interventional procedures. The interventional device assemblies having robotically driven interventional devices and manually driven interventional devices described herein can be readily adapted for any of a wide variety of other diagnostic and therapeutic applications throughout the body, including particularly intravascular procedures such as in the peripheral vasculature (e.g., deep venous thrombosis), central vasculature (pulmonary embolism), and coronary vasculature, as well as procedures in other hollow organs or tubular structures in the body.

The interventional devices described herein may be provided individually or at least some of the interventional devices can be provided in a preassembled (e.g., nested or stacked) configuration. For example, the interventional devices may be provided in the form of an interventional device assembly, such as interventional device assembly 2900, in a concentric nested or stacked configuration. If provided individually, each catheter (and in some embodiments, each corresponding catheter hub) can be unpackaged and primed to remove air from its inner lumen, for example, by flushing the catheter (and in some embodiments, the corresponding catheter hub) to remove air by displacing it with a fluid, such as saline, contrast media, or a mixture of saline and contrast media. After priming, the interventional devices can be manually assembled into a stacked configuration so that they are ready for introduction into the body for a surgical procedure, for example, via an introducer sheath.

Assembling the devices into a stacked configuration can include individually inserting interventional devices into one another by order of size. For example, an interventional device having a second largest diameter can be inserted into the lumen of an interventional device having a largest diameter. An interventional device having a third largest diameter can then be inserted into the interventional device having the second largest diameter and so on.

For example, with respect to FIG. 17, assembly can be performed by first inserting a distal end of the catheter 2904 through the hub 2914 and into the catheter 2906. The catheter 2904 can be advanced through the catheter 2906 until the distal tip of the catheter 2904 is flush with or extends beyond the distal tip of the catheter 2906, and/or until the catheter 2904 cannot be inserted any further. Then, the distal end of the catheter 2902 can be inserted through the hub 2912 and into the catheter 2904. The catheter 2902 can be advanced through the catheter 2904 until the distal tip of the catheter 2902 is flush with or extends beyond the distal tip of the catheter 2904, and/or until the catheter 2902 cannot be inserted any further. Then, the distal end of the guidewire 2907 can be inserted through the hub 2910 and into the catheter 2902. The guidewire 2907 can be advanced through the catheter 2902 until the distal tip of the guidewire 2907 is flush with or extends beyond the distal tip of the catheter 2902, and/or until the guidewire 2907 cannot be inserted any further.

Embodiments in which two or more of the interventional devices are packaged together as a single unit in an assembled (e.g., nested or stacked) configuration may provide efficient unpackaging and preparation prior to use and efficient assembly within a robotic control system. The interventional devices may be pre-mounted to their respective hubs prior to packaging. In certain embodiments, two or three or more interventional devices may be packaged in a fully nested (i.e., fully axially inserted) configuration or nearly fully nested configuration. In a fully nested configuration, each interventional device is inserted as far as possible into an adjacent distal hub and interventional device. Such a fully nested configuration may minimize a total length of the interventional device assembly and minimize the size of the packaging required to house the interventional device assembly.

In some embodiments, the interventional devices may also be sterilized prior to packaging while in the assembled configuration, for example, using ethylene oxide gas. In some embodiments, the interventional devices may be packaged while in the assembled configuration before sterilization with ethylene oxide gas. For interventional devices in a nested or stacked configuration, ethylene oxide gas can be provided in a space between adjacent interventional devices (for example, an annular lumen between an outer diameter of a first interventional device nested within a second interventional device and the inner diameter of the second interventional device) for sterilization. In some embodiments, the interventional device assembly can be packaged in a thermoformed tray and sealed with an HDPE (e.g., Tyvek®) lid. The interventional device assembly can be unpackaged by removal (e.g., opening or peeling off) of the lid by a user in a non-sterile field. A user in the sterile field can then remove the interventional device assembly and place it on the sterile work surface, for example, of a robotic drive table, as described herein.

Packaging the interventional devices in an assembled configuration and sterilized state can reduce the time associated with unpackaging and assembly of individual interventional devices and facilitate efficient connection to a robotic drive system. Each interventional device and hub combination may further be packaged with a fluidics connection for coupling to a fluid source and/or a vacuum source. In some embodiments, each hub or a hemostasis valve coupled to the hub may include the fluidics connection.

After the interventional device assembly is unpackaged (e.g., after the interventional device assembly is positioned on the robotic drive table), priming can be performed while the devices are concentrically nested or stacked. This is preferably accomplished in each fluid lumen, such as, for example, the annular lumen between the catheter 2906 and the catheter 2904 and in between each of the additional concentric interventional devices in the concentric stack. In certain embodiments, the fluid lumen can include a lumen between a distal hub and a proximal interventional device, such as, for example, the lumen between the hub 2914 and the catheter 2904. In certain embodiments, priming can be performed while the devices are still in the sterile packaging.

The fluidics connections can be connected to a fluidics system for delivering saline and contrast media to the catheters and providing aspiration. In some embodiments, the fluidics connections may be passed outside the sterile field for connection to the fluidics system. Once connected, the fluidics system can perform a priming sequence to flush each catheter of the interventional device assembly with fluid (e.g., saline, contrast media, or a mixture of saline and contrast media). The priming sequence may also include flushing each corresponding catheter hub with fluid. The fluid may be de-aired or de-gassed by the fluidics system prior to priming. In some embodiments, a vacuum source of the fluidics system can also be used to evacuate air from each catheter while flushing with fluid. In certain embodiments, a tip of the catheter can be placed into a container of fluid, such as saline, contrast media, or a mixture of saline and contrast media, during priming so that the fluid in the container, and not air, is aspirated through the tip of the catheter when the vacuum source is applied. In other embodiments, the tip of the catheter may be blocked (for example, using a plug) so that air is not aspirated from the tip of the catheter when the vacuum source is applied. In certain embodiments, the priming process may be automated such that a user can provide a single command and each catheter (and in some embodiments, each corresponding catheter hub) can be primed, sequentially (for example, as described with respect to FIGS. 20A-20C) or simultaneously.

Additional details regarding fluidics systems are disclosed in U.S. patent application Ser. No. 17/879,614, entitled Multi Catheter System With Integrated Fluidics Management, filed Aug. 2, 2022, which is hereby expressly incorporated in its entirety herein.

Fluid resistance within a lumen may be greater when there is a reduction in cross sectional luminal area for flow, for example, when a second interventional device (e.g., a catheter or guidewire) extends within the lumen of a first interventional device. The amount of fluid resistance can be affected by the length of the cross sectional narrowing, for example, due to a depth of axial insertion of the second interventional device within the first interventional device. A second interventional device extending partially through the lumen of a first interventional device will provide a smaller length of cross-sectional narrowing, and accordingly may result in a lower fluid resistance within the lumen of the first catheter, than if the second interventional device were to extend entirely through the lumen of the first interventional device. Thus, fluid resistance can be lowered by at least partially decreasing a depth of axial insertion (i.e., axial overlap) of a second interventional device into the lumen through which fluid is to be injected (e.g., a length of the second interventional device into its concentrically adjacent lumen).

In some embodiments, over certain depths of insertion of a second interventional device within a first interventional device (for example, when the second interventional device is at or near a maximum insertion depth within the first interventional device), the size of the fluid channel between the devices (e.g., the annular lumen between the first interventional device and the second interventional device) can lead to higher than desirable amounts of fluid resistance during a priming procedure. In some embodiments, the depth of insertion of the second interventional device within the first interventional device can be decreased to reduce the pressure needed to prime the catheter and reduce internal interference.

In some embodiments, a catheter in the interventional device assembly can be separated from the other interventional devices for priming to reduce the pressure needed to prime the catheter and reduce internal interference. The catheter being primed may be separated from the interventional devices within the lumen of the catheter by proximally retracting the interventional devices within the lumen of the catheter. For example, the interventional devices within the lumen of the catheter being primed can be proximally retracted from the catheter being primed as far as possible while still maintaining a nested or stacked relationship (e.g., at least about 2 cm or 5 cm or more axial overlap) in order to minimize the pressure needed to prime the catheter and minimize internal interference. In other words, a catheter can be separated from more proximal interventional devices for priming while a distal tip of an adjacent proximal interventional device is still positioned within the lumen of the catheter. Maintaining at least some of the distal tip of an adjacent proximal interventional device within the lumen of the catheter may allow for easier reinsertion and advancement of the proximal interventional device after priming.

In some embodiments, the axial overlap may be between about 2 cm and about 20 cm, between about 2 cm and 10 cm, between about 2 cm and 5 cm, between about 5 cm and 20 cm, between about 5 cm and 10 cm, or any other suitable range. In some embodiments, the axial overlap may be at least about 2 cm, at least about 5 cm, at least about 10 cm, at least about 20 cm, no more than 2 cm, no more than 5 cm, no more than 10 cm, no more than 20 cm, about 2 cm, about 5 cm, about 10 cm, about 20 cm, or any other suitable amount.

In some embodiments, the robotic drive table can be programed to proximally retract the inner interventional device(s) from the catheter being primed as much as possible while still maintaining a nested or stacked relationship. In other embodiments, the robotic drive table can be programmed to separate inner devices from the catheter being primed to a distance sufficient to optimize the length of the unobstructed lumen and result in an amount of fluid resistance lower than a threshold value. After the catheter being primed is separated from the other interventional devices, the catheter can be primed by flushing the catheter with fluid, such as saline, contrast media, or a mixture of saline and contrast media.

After the catheter is primed, it may be returned to an initial position and a next catheter of the interventional device assembly can be separated from the other interventional devices within its lumen for priming. This sequence can be repeated for each catheter of the interventional device assembly. In other embodiments, after a catheter is primed, it may be advanced to a ready or drive position to begin insertion into the patient. While the foregoing describes separating catheters to be primed by retraction of inner interventional devices, an outer catheter may also be separated from inner interventional devices by distally axially advancing the outer catheter relative to the inner interventional devices. An example of a priming process is described with respect to FIGS. 20A-20C.

Figures 20A, 20B, 20C:
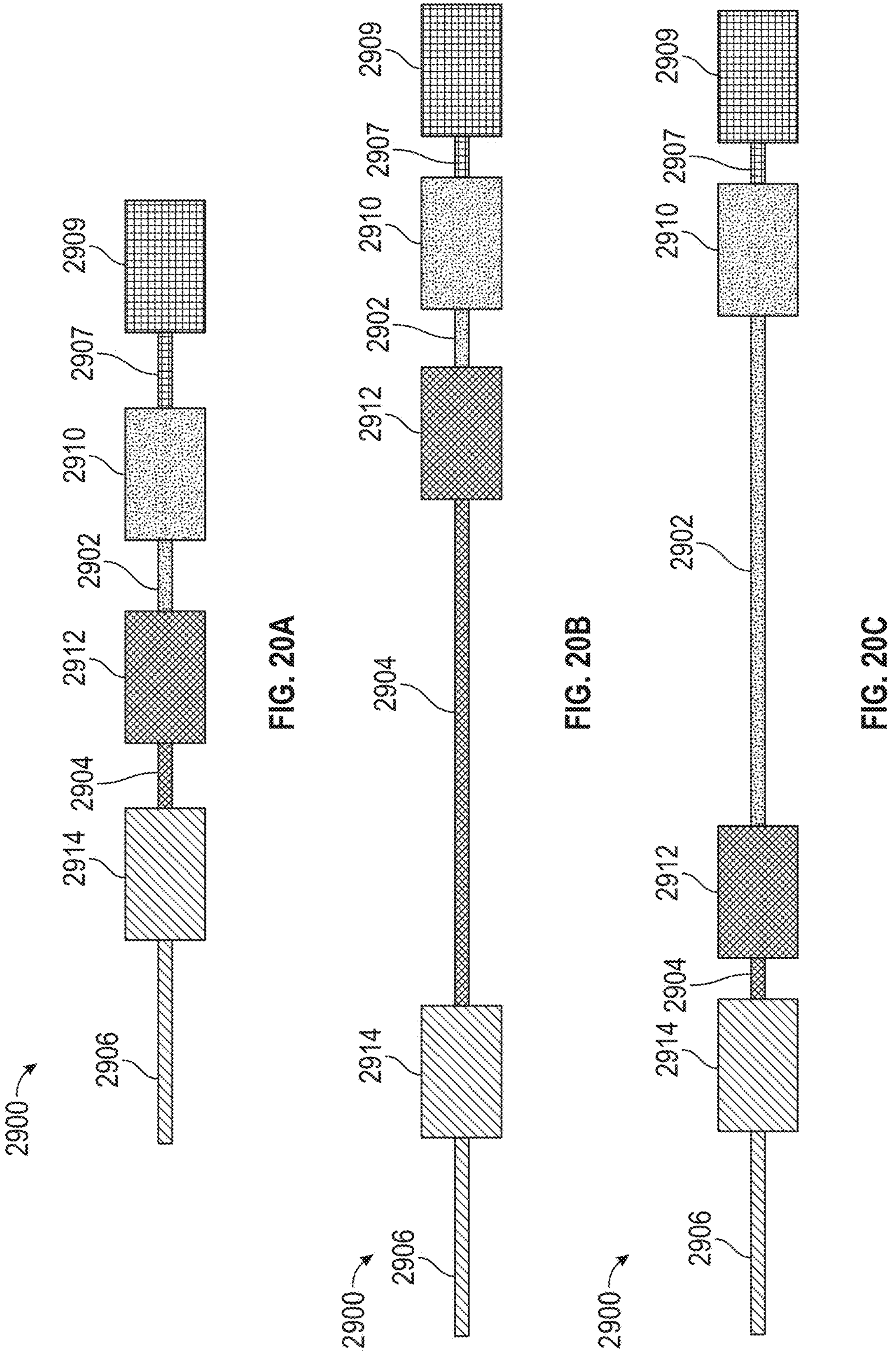
FIGS. 20A-20C depict an example sequence of steps of priming a catheter assembly in a stacked configuration.

FIG. 20A depicts the interventional device assembly 2900 assembled in a concentric stack and axially compressed configuration. As shown in FIG. 20A, the interventional devices can be fully nested within each other. This may be the configuration following unpackaging of the device assembly 2900 and placement onto the robotic drive table. A priming sequence may begin by distally axially advancing the catheter 2906 and hub 2914 relative to the catheter 2904, hub 2912, catheter 2902, hub 2910, guidewire 2907, and hub 2909, for example, as far as possible while maintaining a distal tip of the catheter 2904 within the lumen of the catheter 2906, as shown in FIG. 20B, or to a distance that will result in a desirable amount of fluid resistance for priming. In some embodiments, the catheter 2906 is advanced in response to a control signal from a control system. The catheter 2906 can then be primed by introducing priming fluid using the fluidics system. In some embodiments, priming fluid is introduced in response to a control signal from a control system. Priming the catheter 2906 can include priming the hub 2914. For example, in certain embodiments, the hub 2914 or a hemostasis valve coupled thereto can include fluidics connections to receive priming fluid from the fluidics system. After priming, the catheter 2906 can be returned to its initial position (e.g., the fully axially compressed configuration) as shown in FIG. 20A. In some embodiments, the catheter 2906 is returned to its initial position in response to a control signal from a control system.

After the catheter 2906 is primed and returned to its initial position, the catheter 2904 and hub 2912 can be distally axially advanced relative to the catheter 2902, hub 2910, guidewire 2907 and hub 2909 (also distally axially advancing the catheter 2906 and hub 2914 without changing or minimally changing their relative position with respect to catheter 2904), for example, as far as possible while maintaining a distal tip of the catheter 2902 within the lumen of the catheter 2904, as shown in FIG. 20C, or to a distance that will result in a desirable amount of fluid resistance for priming. In some embodiments, the catheter 2904 and the catheter 2906 are advanced in response to a control signal from a control system. The catheter 2904 can then be primed by introducing priming fluid using the fluidics system. In some embodiments, priming fluid is introduced in response to a control signal from a control system. Priming the catheter 2904 can include priming the hub 2912. For example, in certain embodiments, the hub 2912 or a hemostasis valve coupled thereto can include fluidics connections to receive priming fluid from the fluidics system. After priming, the catheter 2904 and catheter 2906 can be returned to their initial positions (e.g., the fully axially compressed configuration) as shown in FIG. 20A. In some embodiments, the catheter 2904 and the catheter 2906 are returned to their initial position in response to a control signal from a control system.

After the catheter 2904 is primed and returned to its initial position, the catheter 2902 and hub 2910 can be distally axially advanced relative to the guidewire 2907 and hub 2909 (also distally axially advancing the catheter 2906, hub 2914, catheter 2904, and hub 2912 without changing or minimally changing their relative positions with respect to the catheter 2902), for example, as far as possible while maintaining a distal tip of the guidewire 2907 within the lumen of the catheter 2902, or to a distance that will result in a desirable amount of fluid resistance for priming. In some embodiments, the catheter 2902, the catheter 2904, and the catheter 2906 are advanced in response to a control signal from a control system. The catheter 2902 can then be primed by introducing priming fluid using the fluidics system. In some embodiments, priming fluid is introduced in response to a control signal from a control system. Priming the catheter 2902 can include priming the hub 2910. For example, in certain embodiments, the hub 2910 or a hemostasis valve coupled thereto can include fluidics connections to receive priming fluid from the fluidics system. After priming, the catheter 2902 and catheters 2904 and 2906 can be returned to their initial positions (e.g., the fully axially compressed configuration) shown in FIG. 20A. In some embodiments, the catheter 2902, the catheter 2904, and the catheter 2906 are returned to their initial position in response to a control signal from a control system.

In some embodiments, the priming procedure described with respect to FIGS. 20A-20C may be performed in response to a single control signal from a control system. In other embodiments, various steps of the priming procedure may be performed in response to unique control signals. In some embodiments, priming of each unique interventional device can be performed in response to a unique control signal.

In alternative embodiments, each of the catheters can be distally separated from one another simultaneously for priming. For example, the catheter 2902 can be distally separated from the guidewire 2907 while maintaining the distal tip of the guidewire 2907 in the lumen of the catheter 2902, the catheter 2904 can be distally separated from the catheter 2902 while maintaining the distal tip of the catheter 2902 in the lumen of the catheter 2904, and the catheter 2906 can be distally separated from the catheter 2904 while maintaining the distal tip of the catheter 2904 in the lumen of the catheter 2906 simultaneously. However, an embodiment in which only one set of adjacent hubs is separated at a time, as described with respect to FIGS. 20A-20C, can provide a smaller overall length of the assembly at any particular time, which can allow for use with a smaller robotic drive system. While separation of outer catheters from their inner interventional devices is described as distally axially advancing the catheters relative to their inner interventional devices, separation can include proximally retracting the inner interventional devices from the outer catheters.

In alternative embodiments, one or more of the catheter 2902, the catheter 2904, and the catheter 2906 can be advanced to a ready or drive position to begin insertion into the patient after priming (e.g., prior to priming a subsequent catheter). In such embodiments, the catheters may advance to the ready or drive position without returning to their initial position after priming.

As described above, in some embodiments, the catheters 2902, 2904, and 2906 may be assembled into the concentric stack orientation illustrated in FIG. 17 prior to flushing the catheters to remove air by displacing it with a fluid such as saline contrast media, or a mixture of saline and contrast media. This is preferably accomplished in each fluid lumen, such as, for example, the annular lumen between the catheter 2906 and the catheter 2904 and in between each of the additional concentric interventional devices in the concentric stack. Infusing fluid (e.g., saline, contrast media, or a mixture of saline and contrast media) under pressure may displace substantially all of the air but some small bubbles may remain, adhering to the inside wall of an outer catheter (e.g., the guide catheter 2906), the outside wall of an inner catheter (e.g., the procedure catheter 2904), or both.

While fluid is being introduced under pressure into the proximal end of the annular lumen (e.g., into a hub of the outer catheter or a hemostasis valve coupled thereto), the inner catheter may be moved with respect to the outer catheter, to disrupt the holding forces between the microbubbles and adjacent wall and allow the bubbles to be carried downstream and out through the distal opening of the lumen or removed via aspiration. The catheters may be moved axially, rotationally or both with respect to each other. In certain embodiments, the catheters may be reciprocated axially, rotationally, or both with respect to each other. In some embodiments, the catheters may be moved intermittently axially, rotationally, or both. In other embodiments, the catheters may be rotated continuously or in a constant direction.

In some implementations, a first catheter is moved reciprocally with respect to an adjacent catheter or guidewire such as axially over a stroke length in a range of from about 1 mm to about 250 mm, from about 10 mm to about 250 mm, from about 5 mm to about 125 mm, from about 25 mm to about 125 mm, from about 10 mm to about 50 mm, from about 15 mm to about 30 mm, from about 5 mm to about 30 mm, from about 15 mm to about 25 mm, from about 20 mm to about 40 mm, or any other suitable range. In some implementations, a first catheter is moved reciprocally with respect to an adjacent catheter or guidewire such as axially over a stroke length of at least 5 mm, at least 10 mm, at least 15 mm, at least 20 mm, at least 25 mm, at least 30 mm, at least 50 mm, no more than 10 mm, no more than 20 mm, no more than 25 mm, no more than 30 mm, no more than 50 mm, no more than 125 mm, no more than 150 mm, about 5 mm, about 10 mm, about 15 mm, about 20 mm, about 25 mm, about 30 mm, about 50 mm, or any other suitable stroke length.

In some implementations, a first catheter is moved reciprocally with respect to an adjacent catheter or guidewire such as axially at a reciprocation frequency in a range of from about 0.5 Hz to about 1 Hz, from about 1 Hz to about 5 Hz, from about 1 Hz to about 10 Hz, from about 1 Hz to about 25 Hz, from about 5 Hz to about 10 Hz, from about 10 Hz to about 25 Hz, or any other suitable range of frequencies. In some implementations, the first catheter is moved reciprocally with respect to an adjacent catheter or guidewire such as axially at a reciprocation frequency of at least 0.5 Hz, at least 1 Hz, at least 2 Hz, at least 5 Hz, at least 10 Hz, at least 25 Hz, no more than 0.5 Hz, no more than 1 Hz, no more than 2 Hz, no more than 5 Hz, no more than 10 Hz, no more than 25 Hz, about 0.5 Hz, about 1 Hz, about 2 Hz, about 5 Hz, about 10 Hz, about 25 Hz or any other suitable frequency.

In one implementation, a first catheter is moved reciprocally with respect to the adjacent catheter or guidewire such as axially over a stroke length in a range of from about 0.5 inches to about 10 inches, or from about one inch to about 5 inches at a reciprocation frequency of no more than about 5 cycles per second or two cycles per second or less.

In some implementations, a first catheter is moved reciprocally with respect to an adjacent catheter or guidewire such as rotationally over an angle of rotation per stroke in a range of from about 5 degrees to about 180 degrees, from about 5 degrees to about 360 degrees, from about 15 degrees to about 180 degrees, from about 15 degrees to about 150 degrees, from about 15 degrees to about 120 degrees, from about 15 degrees to about 90 degrees, form about 15 degrees to about 60 degrees, from about 15 degrees to about 30 degrees, from about 30 degrees to about 180 degrees, from about 30 degrees to about 150 degrees, from about 30 degrees to about 120 degrees, from about 30 degrees to about 90 degrees, form about 30 degrees to about 60 degrees, from about 60 degrees to about 180 degrees, from about 60 degrees to about 150 degrees, from about 60 degrees to about 120 degrees, from about 60 degrees to about 90 degrees, from about 90 degrees to about 180 degrees, from about 90 degrees to about 150 degrees, from about 90 degrees to about 120 degrees, from about 120 degrees to about 180 degrees, from about 120 degrees to about 150 degrees, from about 150 degrees to about 180 degrees or any other suitable range. In some implementations, a first catheter is moved reciprocally with respect to an adjacent catheter or guidewire such as rotationally over an angle of rotation per stroke of at least 5 degrees, at least 15 degrees, at least 30 degrees, at least 60 degrees, at least 90 degrees, at least 120 degrees, at least 150 degrees, at least 180 degrees, at least 360 degrees, no more than 5 degrees, no more than 15 degrees, no more than 30 degrees, no more than 60 degrees, no more than 90 degrees, no more than 120 degrees, no more than 150 degrees, no more than 180 degrees, no more than 360 degrees, about 5 degrees, about 15 degrees, about 30 degrees, about 60 degrees, about 90 degrees, about 120 degrees, about 150 degrees, about 180 degrees, about 360 degrees, or any other suitable angle.

In some implementations, a first catheter is moved reciprocally with respect to an adjacent catheter or guidewire such as rotationally at a reciprocation frequency in a range of from about 0.5 Hz to about 1 Hz, from about 1 Hz to about 5 Hz, from about 1 Hz to about 10 Hz, from about 1 Hz to about 25 Hz, from about 5 Hz to about 10 Hz, from about 10 Hz to about 25 Hz, or any other suitable range of frequencies. In some implementations, the first catheter is moved reciprocally with respect to an adjacent catheter or guidewire such as rotationally at a reciprocation frequency of at least 0.5 Hz, at least 1 Hz, at least 2 Hz, at least 5 Hz, at least 10 Hz, at least 25 Hz, no more than 0.5 Hz, no more than 1 Hz, no more than 2 Hz, no more than 5 Hz, no more than 10 Hz, no more than 25 Hz, about 0.5 Hz, about 1 Hz, about 2 Hz, about 5 Hz, about 10 Hz, about 25 Hz or any other suitable frequency.

In some implementations, a first catheter is moved reciprocally with respect to an adjacent catheter or guidewire for a number of reciprocations between 1 and 200, between 1 and 100, between 1 and 50, between 1 and 25, between 1 and 15, between 1 and 10, between 1 and 5, between 5 and 25, between 5 and 15, between 5 and 10, or any other suitable range. In some implementations, a first catheter is moved reciprocally with respect to an adjacent catheter or guidewire for at least 1 reciprocation, at least 2 reciprocations, at least 5 reciprocations, at least 10 reciprocations, at least 15 reciprocations, at least 25 reciprocations, at least 50 reciprocations, no more than 5 reciprocations, no more than 10 reciprocations, no more than 15 reciprocations, no more than 25 reciprocations, no more 50 than reciprocations, no more than 100 reciprocations, no more than 200 reciprocations, about 1 reciprocation, about 2 reciprocations, about 5 reciprocations, about 10 reciprocations, about 25 reciprocations, about 50 reciprocations, about 100 reciprocations, about 200 reciprocations, or any other suitable number. One reciprocation can include a movement (axially or rotationally) from a first position to a second position followed by a return from the second position to the first position.

In some implementations, a first catheter is moved reciprocally with respect to an adjacent catheter or guidewire over a length of time in a range of from 1 about second to about 60 seconds, from about 1 second to about 45 seconds, from about 1 second to about 30 seconds, from about 1 second to about 20 seconds, from about 1 second to about 15 seconds, from about 1 second to about 10 seconds, from about 5 seconds to about 45 seconds, from about 5 seconds to about 30 seconds, from about 5 seconds to about 20 seconds, from about 5 seconds to about 15 seconds, from about 5 seconds to about 10 seconds, from about 10 seconds to about 30 seconds, from about 10 seconds to about 20 seconds, or any other suitable range. In some implementations, a first catheter is moved reciprocally with respect to an adjacent catheter or guidewire over a length of time of at least 1 second, at least 5 seconds, at least 10 seconds, at least 15 seconds, at least 20 seconds, at least 30 seconds, at least 45 seconds, at least 60 seconds, no more than 5 seconds, no more than 10 seconds, no more than 15 seconds, no more than 20 seconds, no more than 30 seconds, no more than 45 seconds, no more than 60 seconds, about 5 seconds, about 10 seconds, about 15 seconds, about 20 seconds, about 30 seconds, about 45 seconds, about 60 seconds, or any other suitable length of time.

Reciprocation of adjacent catheters to disrupt microbubbles may be accomplished manually by grasping the corresponding catheter hubs and manually moving the catheters axially or rotationally with respect to each other while delivering pressurized fluid (e.g., saline, contrast media, or a mixture of saline and contrast media). Alternatively, such as in a robotically driven system, a processor may be configured to robotically drive at least one of two adjacent catheter hubs (for example, at least one of hub 2914 and hub 2912) to achieve relative movement between the adjacent catheters thereby disrupting and expelling microbubbles, such as in response to user activation of a flush control. For example, in certain embodiments, two adjacent interventional devices may be moved relative to one another in response to a control signal from a control system. In certain embodiments, delivery of pressurized fluid may be performed in response to a control signal from a control system.

The reciprocation of adjacent catheters may generate shear forces that dislodge the air bubbles. For example, relative movement of the inner and outer surfaces of adjacent catheters may increase the fluid shear rate between the adjacent catheters during priming in comparison to static surfaces. In some embodiments, the shear force can be increased by increasing the flow rate of the solution (e.g., saline, contrast media, or a mixture of saline and contrast media) being provided by the fluidics system. In certain embodiments, both flow rate and relative movement between adjacent catheters are controlled to dislodge air bubbles.

In some embodiments, after each catheter is primed by the fluidics system, an ultrasound bubble detector may be used to confirm that the catheters are substantially free of air bubbles. For example, an ultrasound chip (such as mounted within a hub adjacent a catheter receiving lumen) may be run along the length of the catheters to confirm that no air bubbles remain in the system.

Figure 21A:
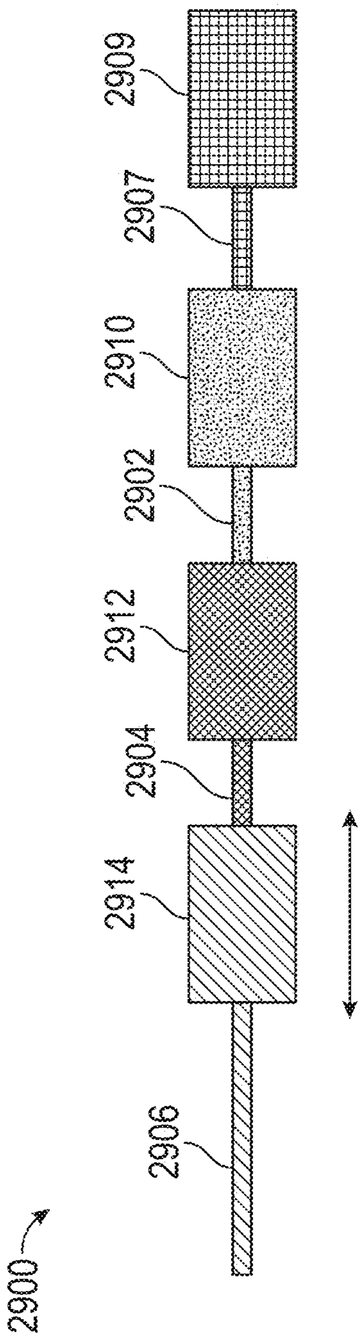
FIGS. 21A-21B depict an example sequence of steps of priming a catheter assembly in a stacked configuration.
Figure 21B:
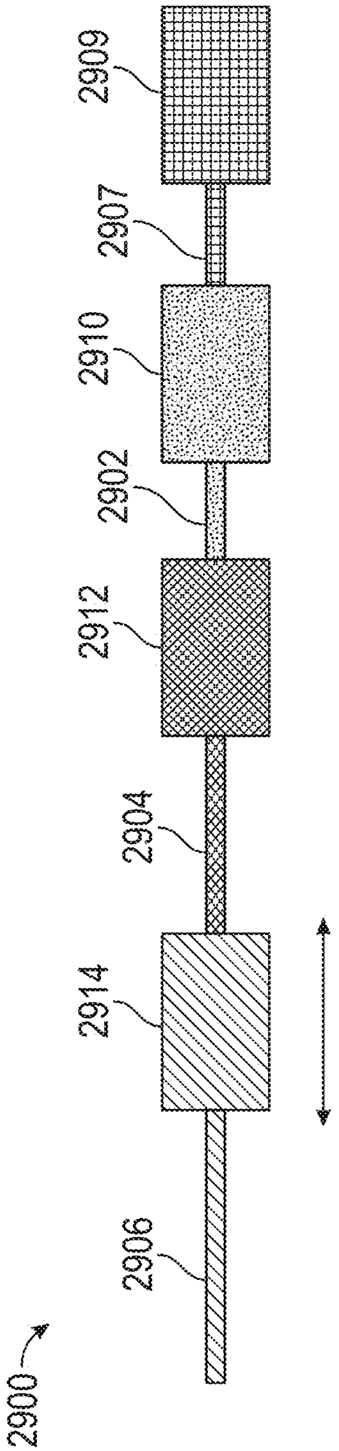

An example of a priming process including reciprocal movement of adjacent catheters is described with respect to FIGS. 21A-21B.

FIG. 21A depicts the interventional device assembly 2900 assembled in a concentric stack configuration. As shown in FIG. 21A, the interventional devices can be fully nested within each other. This may be the configuration following unpackaging of the device assembly 2900 and placement onto the robotic drive table. Alternatively, individual interventional devices of the device assembly 2900 can be assembled into the device assembly 2900 on the drive table.

A priming sequence may begin by priming the catheter 2906. In some embodiments, the catheter 2906 can be primed by introducing fluid (e.g., saline, contrast media, or a mixture of saline and contrast media) under pressure into the lumen of the catheter 2906 while generating reciprocal movement of catheter 2906 and/or hub 2914, axially, rotationally or both, relative to the catheter 2904. Priming the catheter 2906 can include priming the hub 2914. For example, in certain embodiments, the hub 2914 or a hemostasis valve coupled thereto can include fluidics connections to receive priming fluid from the fluidics system. In certain embodiments, the catheter 2906 and/or hub 2914 can be axially agitated back and forth along a longitudinal axis of the catheter 2906 (e.g., between the position of FIG. 21A and the position of FIG. 21B). Axial and/or rotational reciprocal motion of the catheter 2906 and/or hub 2914 can be performed manually or by a robotic drive table. Reciprocal movement may be generated in response to a control signal from a control system. Introducing fluid under pressure may be performed in response to a control signal from a control system.

In some embodiments, priming of the catheter 2906 may be performed by introducing fluid (e.g., saline, contrast media, or a mixture of saline and contrast media) under pressure into the lumen of the catheter 2906 while generating reciprocal movement of the catheter 2904 and/or hub 2912, axially, rotationally or both, relative to the catheter 2906. Axial and/or rotational reciprocal motion of the catheter 2904 and/or hub 2912 can be performed manually or by a robotic drive table. Reciprocal movement may be generated in response to a control signal from a control system. Introducing fluid under pressure may be performed in response to a control signal from a control system.

In some embodiments, priming of the catheter 2906 may be performed by introducing fluid (e.g., saline, contrast media, or a mixture of saline and contrast media) under pressure into the lumen of the catheter 2906 while generating reciprocal movement of both the catheter 2906 (and/or hub 2914) and the catheter 2904 (and/or hub 2912), axially, rotationally or both, relative to one another. Reciprocal movement may be generated in response to a control signal from a control system. Introducing fluid under pressure may be performed in response to a control signal from a control system.

In some embodiments, after priming the catheter 2906, the catheter 2906 can be returned to an initial position as shown in FIG. 21A. In other embodiments, after priming the catheter 2906, the catheter 2906 can be advanced to a ready or drive position to begin insertion into the patient.

In some embodiments, after the catheter 2906 is primed, the catheter 2904 can be primed. Priming the catheter 2904 can include priming the hub 2912. For example, in certain embodiments, the hub 2912 or a hemostasis valve coupled thereto can include fluidics connections to receive priming fluid from the fluidics system. In some embodiments, the catheter 2904 can be primed by introducing fluid (e.g., saline, contrast media, or a mixture of saline and contrast media) under pressure into the lumen of the catheter 2904 while generating reciprocal movement of the catheter 2904 and/or hub 2912, axially, rotationally or both, relative to the catheter 2902. Reciprocal movement may be generated in response to a control signal from a control system. Introducing fluid under pressure may be performed in response to a control signal from a control system.

In some embodiments, priming of the catheter 2904 may be performed by introducing fluid (e.g., saline, contrast media, or a mixture of saline and contrast media) under pressure into the lumen of the catheter 2904 while generating reciprocal movement of the catheter 2902 and/or hub 2910, axially, rotationally or both, relative to the catheter 2904. Axial and/or rotational reciprocal motion of the catheter 2902 and/or hub 2910 can be performed manually or by a robotic drive table. Reciprocal movement may be generated in response to a control signal from a control system. Introducing fluid under pressure may be performed in response to a control signal from a control system.

In some embodiments, priming of the catheter 2904 may be performed by introducing fluid (e.g., saline, contrast media, or a mixture of saline and contrast media) under pressure into the lumen of the catheter 2904 while generating reciprocal movement of both the catheter 2904 (and/or hub 2912) and the catheter 2902 (and/or hub 2910), axially, rotationally or both, relative to one another. Reciprocal movement may be generated in response to a control signal from a control system. Introducing fluid under pressure may be performed in response to a control signal from a control system.

In some embodiments, after priming the catheter 2904, the catheter 2904 can be returned to an initial position as shown in FIG. 21A. In some embodiments, after priming the catheter 2904, the catheter 2904 can be advanced to a ready or drive position to begin insertion into the patient.

In some embodiments, after the catheter 2904 is primed, the catheter 2902 can be primed. Priming the catheter 2902 can include priming the hub 2910. For example, in certain embodiments, the hub 2910 or a hemostasis valve coupled thereto can include fluidics connections to receive priming fluid from the fluidics system. In some embodiments, the catheter 2902 can be primed by introducing fluid (e.g., saline, contrast media, or a mixture of saline and contrast media) under pressure into the lumen of the catheter 2902 while generating reciprocal movement of the catheter 2902 and/or hub 2910, axially, rotationally or both, relative to the guidewire 2907. Reciprocal movement may be generated in response to a control signal from a control system. Introducing fluid under pressure may be performed in response to a control signal from a control system.

In some embodiments, priming of the catheter 2902 may be performed by introducing fluid (e.g., saline, contrast media, or a mixture of saline and contrast media) under pressure into the lumen of the catheter 2902 while generating reciprocal movement of the guidewire 2907 and/or hub 2909, axially, rotationally or both, relative to the catheter 2902. Axial and/or rotational reciprocal motion of the guidewire 2907 and/or hub 2909 can be performed manually or by a robotic drive table. Reciprocal movement may be generated in response to a control signal from a control system. Introducing fluid under pressure may be performed in response to a control signal from a control system.

In some embodiments, priming of the catheter 2902 may be performed by introducing fluid (e.g., saline, contrast media, or a mixture of saline and contrast media) under pressure into the lumen of the catheter 2902 while generating reciprocal movement of both the catheter 2902 (and/or hub 2910) and the guidewire 2907 (and/or hub 2909), axially, rotationally or both, relative to one another. Reciprocal movement may be generated in response to a control signal from a control system. Introducing fluid under pressure may be performed in response to a control signal from a control system.

In some embodiments, after priming the catheter 2902, the catheter 2902 can be returned to an initial position as shown in FIG. 21A. In other embodiments, after priming the catheter 2902, the catheter 2902 can be advanced to a ready or drive position to begin insertion into the patient.

In some embodiments, the priming procedure described with respect to FIGS. 21A and 21B may be performed in response to a single control signal from a control system. In other embodiments, various steps of the priming procedure may be performed in response to unique control signals. In some embodiments, priming of each unique interventional device can be performed in response to a unique control signal.

In the priming sequence described herein with respect to FIGS. 21A and 21B, the catheters are primed in order starting with the catheter 2906, followed by the catheter 2904, and then followed by the catheter 2902. However, it is contemplated that the catheters may be primed in any order. The catheters may be primed in series as described above with respect to FIGS. 21A and 21B. Alternatively, two or more of the catheters or each of the catheters may be primed in parallel.

In certain embodiments, priming the catheters can include decreasing a depth of axial insertion (i.e., axial overlap) of a second interventional device into the lumen of a first interventional device through which fluid is to be injected (e.g., a length of the second interventional device into its concentrically adjacent lumen), as described with respect to FIGS. 20A-20C, and also generating relative reciprocal movement, axially, rotationally or both, between first interventional device and the second interventional device during priming, as discussed with respect to FIGS. 21A and 21B.

In some implementations, priming of a catheter can include vibrating at least a portion of the catheter and/or its associated hub when included. Vibration can be induced, for example, by an electric motor incorporated into a hub of the catheter, or by a separate electric motor or source of vibration put against the catheter when priming. In some implementations, at least a portion of the support table on which the catheters and/or their associated hubs are placed upon can vibrate during priming of any one or more catheters to aid in removal of air and/or microbubbles of air. Such vibration can be performed by an electric motor.

EXAMPLES

Additional embodiments are disclosed in further detail in the following examples, which are not in any way intended to limit the scope of the claims.

Figure 22:
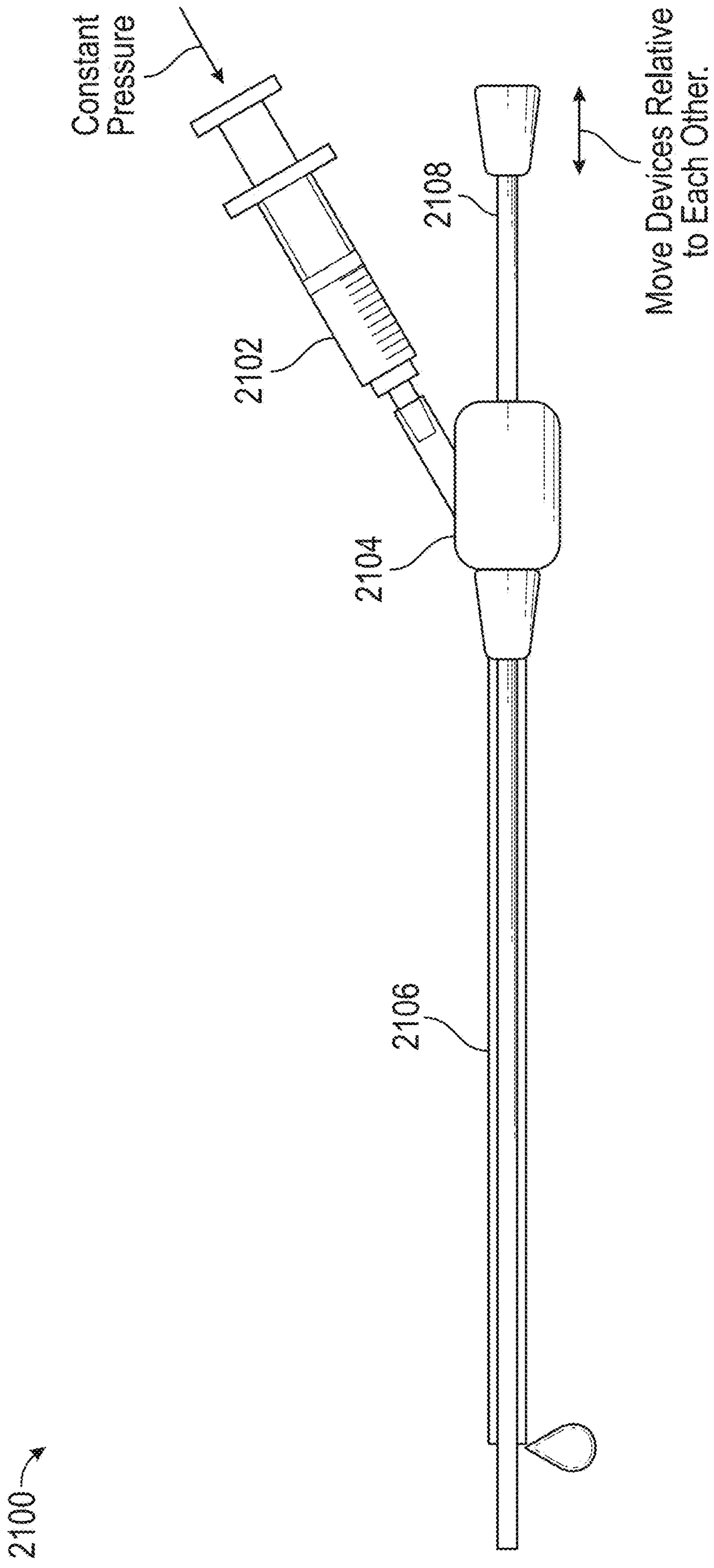
FIG. 22 depicts an example test system for the priming process depicted in FIGS. 21A-21B.
Figure 23A:
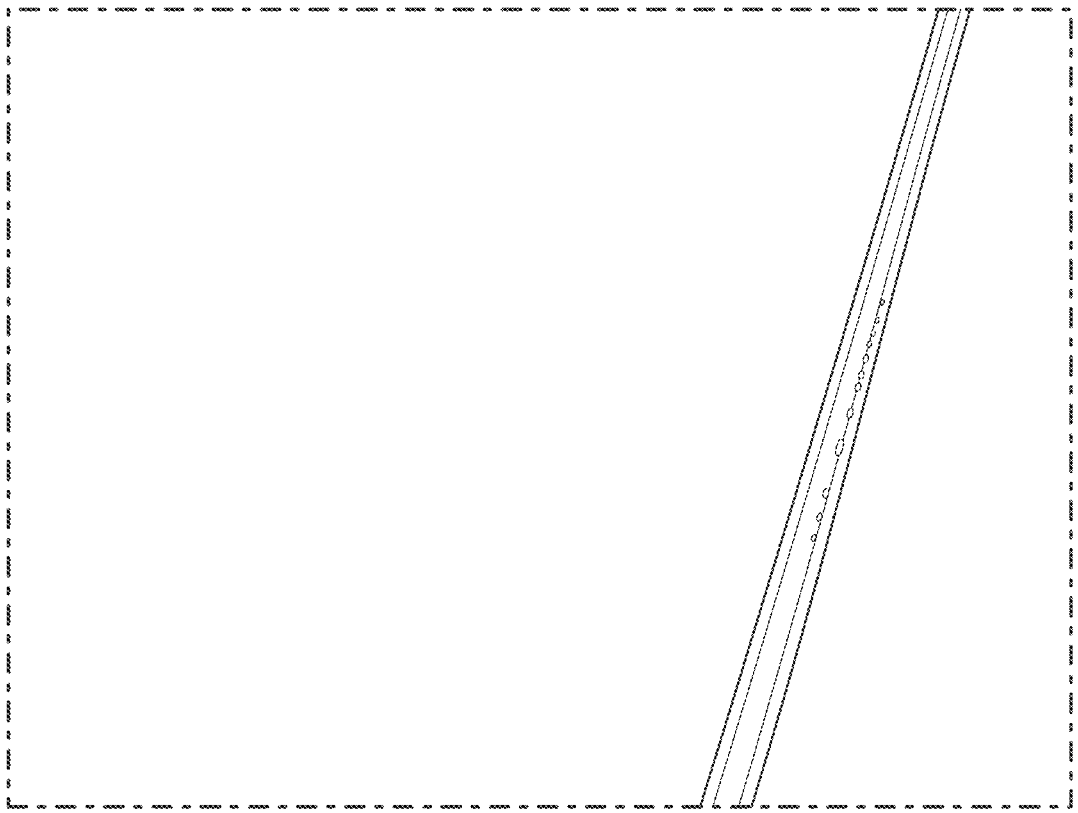
FIG. 23A shows an example of a catheter assembly.
Figure 23B:
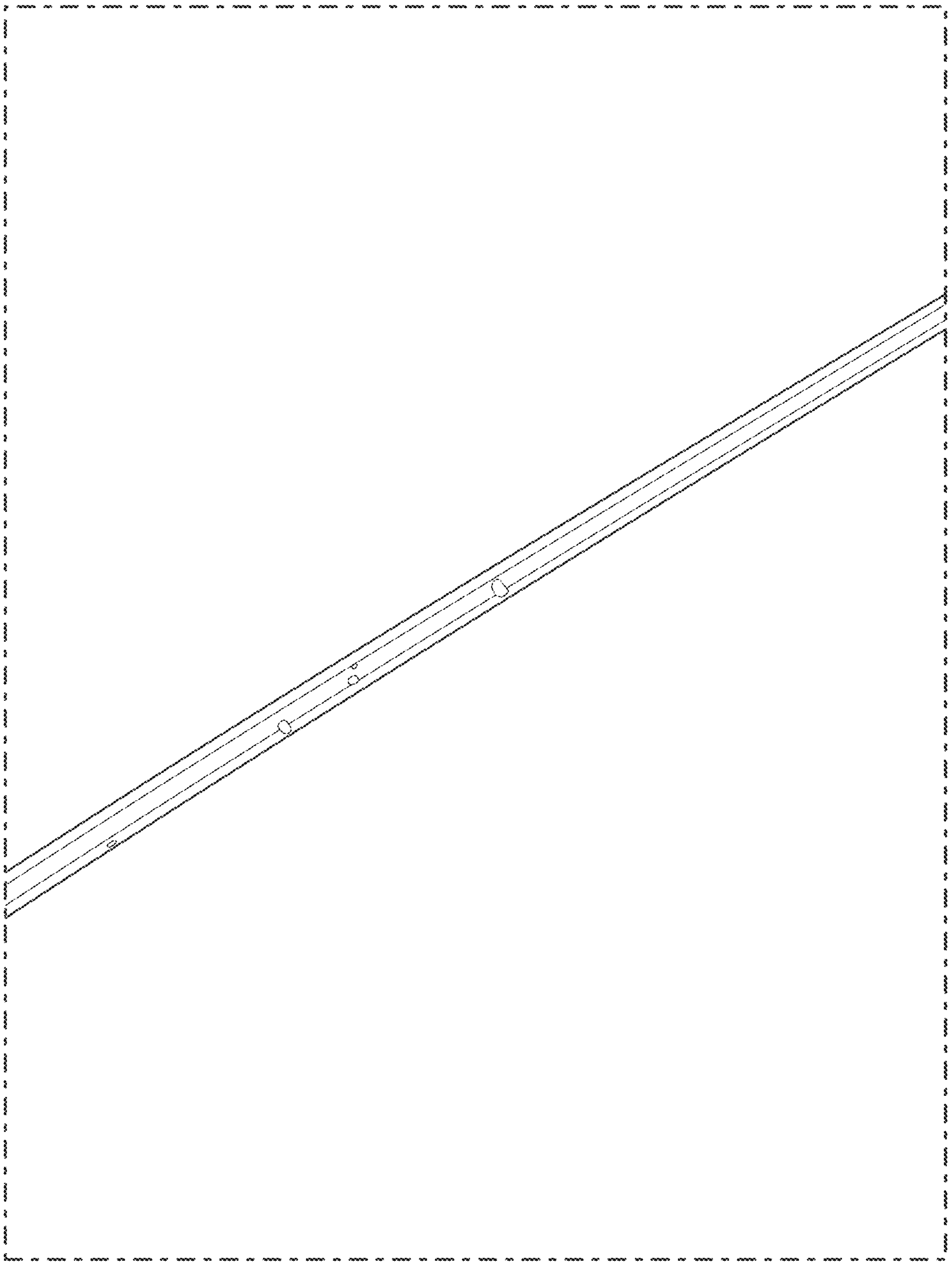
FIG. 23B shows an example of a catheter assembly after a priming procedure.
Figure 23C:
FIG. 23C shows an example of a catheter assembly after a priming procedure including relative movement between adjacent catheters.
Figure 23D:
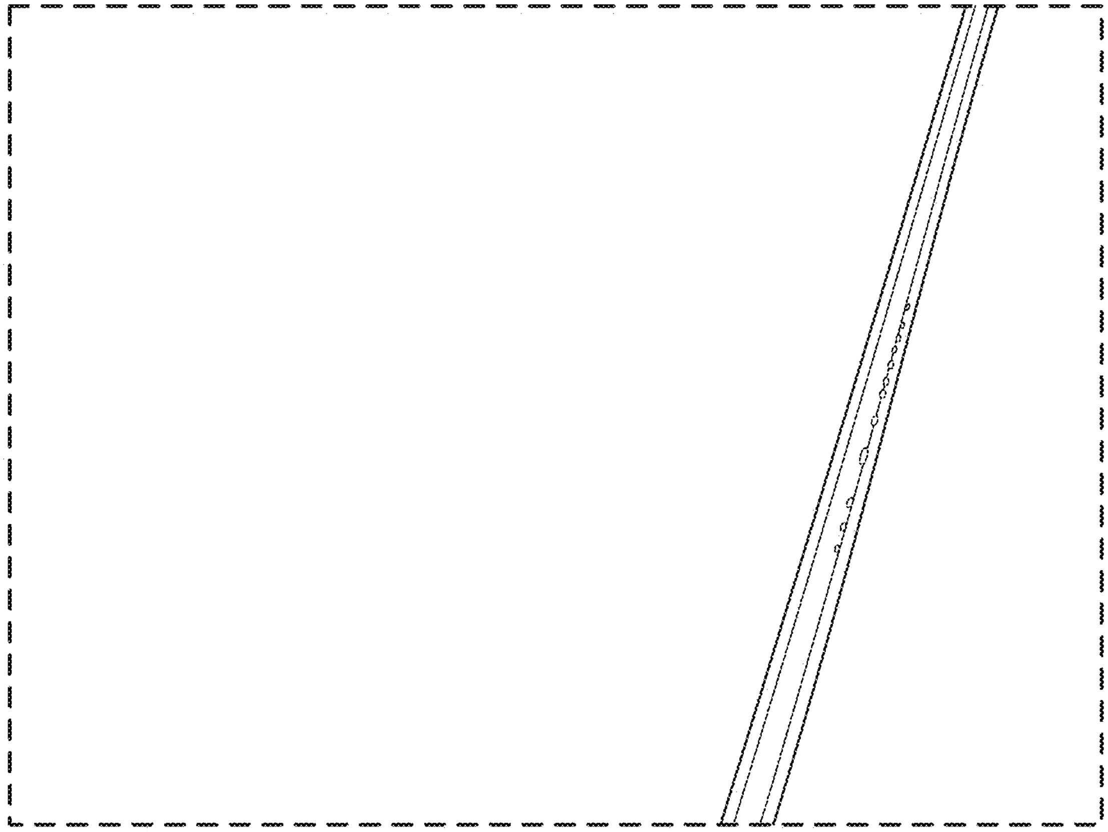
FIGS. 23D-23F illustrate the example catheter assembly of FIGS. 23A-23C.

FIG. 22 is a diagram of a test system that was used for detecting the removal of air bubbles between concentrically stacked catheters. The test system included an inner catheter 2108 positioned within an interior lumen of an outer catheter 2106 in a concentric stack. The outer catheter 2106 was coupled to a rotating hemostasis valve 2104. The hemostasis valve 2104 was coupled to a syringe 2102 so that fluid injected using the syringe would flow through the lumen between the inner catheter 2108 and the outer catheter 2016. In the test system, the inner catheter 2108 had a diameter of about 0.071 inches. The outer catheter 2106 had a diameter of about 0.088 inches. The outer catheter 2106 was transparent to permit visualization of bubbles within the lumen. A distal end of the outer catheter 2108 allowed for small volumes of fluid to exit the outer catheter. FIG. 23A is a photograph showing the catheter 2106 and catheter 2108 in a concentric stack, prior to injection of fluid. FIG. 23D is an illustration thereof.

Example 1

Figure 23E:
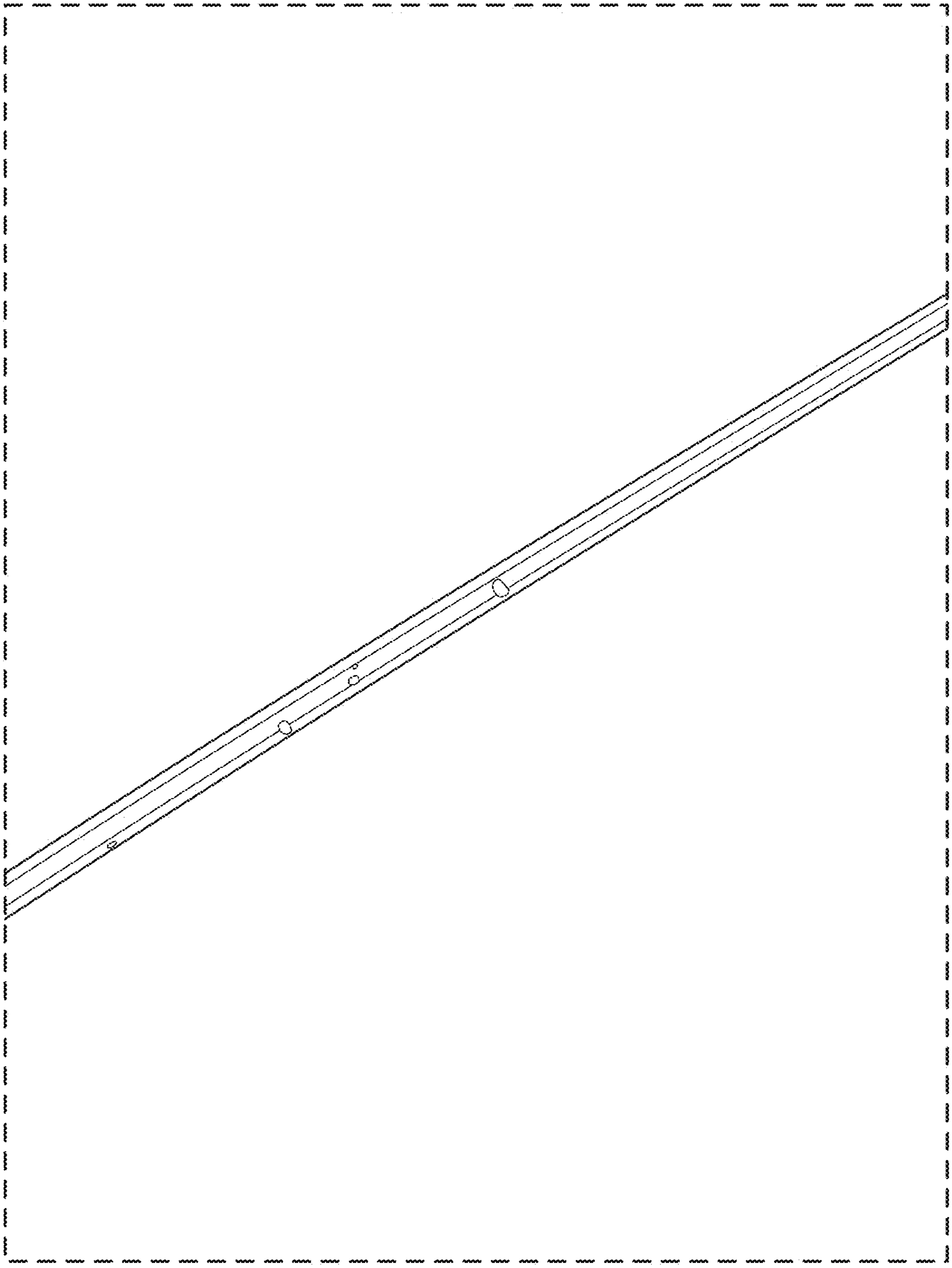

In a first example, the syringe 2102 was used to inject water at a constant pressure of about 150 psi through the hemostasis valve 2104 without moving the catheter 2106 or the catheter 2108. FIG. 23B is a photograph showing the catheter 2106 and catheter 2108 following the injection of water. FIG. 23E is an illustration thereof. As shown in FIG. 23B, bubbles are present within the lumen between the catheter 2106 and the catheter 2108.

Example 2

Figure 23F:
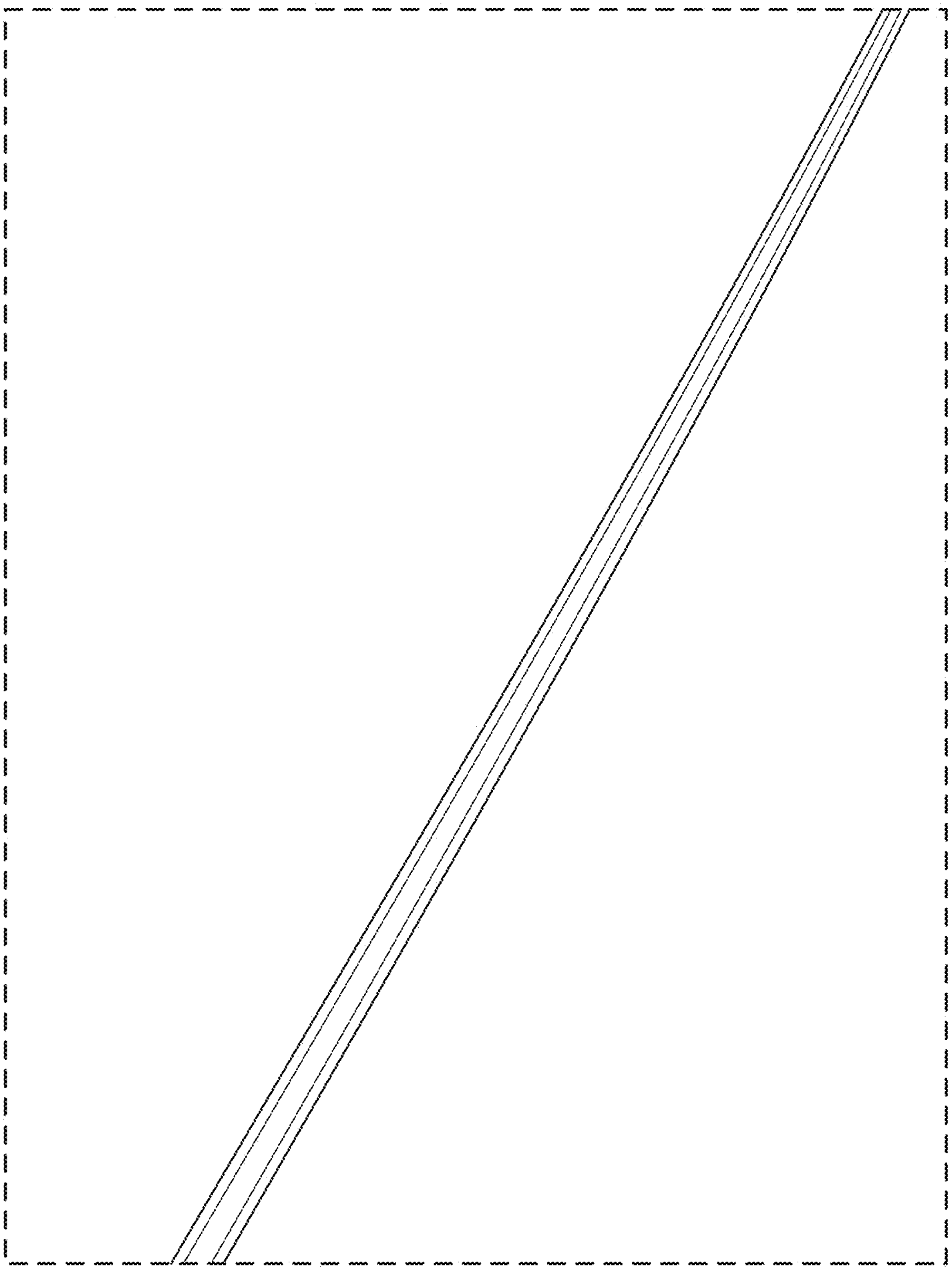

In a second example, the syringe 2102 was used to inject water at a constant pressure of about 150 psi through the hemostasis valve 2104. Shortly after beginning to inject water, axial reciprocal movement of the inner catheter 2108 was performed for about 10 seconds. The reciprocal movement was performed at a frequency of about 1 Hz (or less) and a stroke length of about 20 mm (or more). FIG. 23C is a photograph showing the catheter 2106 and the catheter 2108 following the axial reciprocal movement. FIG. 23F is an illustration thereof. As shown in FIG. 23C, the lumen between the catheter 2106 and the catheter 2108 was substantially free of bubbles.

Example 3

In a third example, an outer catheter having a diameter of about 0.071 inches and an inner catheter having a diameter of about 0.035 inches were used in the test system 2100 instead of the outer catheter 2106 and the inner catheter 2108 described with respect to Examples 1 and 2. A syringe 2102 was used to inject water at a constant pressure of about 150 psi through a hemostasis valve 2104 coupled to the outer catheter. Shortly after beginning to inject water, axial reciprocal movement of the inner catheter was performed for about 10 seconds. The reciprocal movement was performed at a frequency of about 1 Hz (or less) and a stroke length of about 20 mm (or more). Following the axial reciprocal movement, the lumen between the outer and inner catheters was found to be substantially free of bubbles by visual inspection.

Control System

Figure 24:
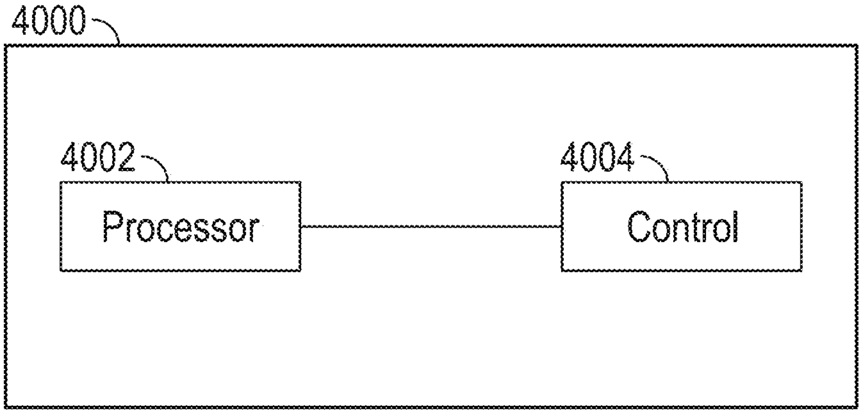
FIG. 24 depicts a schematic of a control system.

FIG. 24 illustrates a schematic view of an example of a control system 4000 that may be used to electronically control the systems and components described herein and/or perform the methods described herein. The control system 4000 may be configured to automatically adjust various motors, hub adapters, hubs, interventional devices, fluidics components (e.g., valves, pumps, etc.), and/or any other components described herein in response to commands input by an operator such as a physician. In response to command inputs by an operator, the control system 4000 may cause a series of responsive events to automatically occur.

In certain embodiments, the control system 4000 can include one or more processors 4002. The one or more processors 4002 can be configured to automatically adjust the various system components described herein in response to commands input by an operator, for example, using one or more controls 4004 of the control system 4000. A single control 4004 is shown in FIG. 24. However, any suitable number of controls may be provided to correspond to various functions of the systems described herein. For example, in certain embodiments, each interventional device may have its own unique control 4004 or set of controls 4004 that can control various functions of the interventional device (e.g., axial movement, rotational movement, supply of fluids (e.g., saline, contrast, etc.), aspiration, etc.).

In certain embodiments, one or more controls 4004 may control priming functions for one or more interventional devices. For example, one or more controls 4004 can be operated to cause the interventional devices to perform a priming procedure, as described for example, with reference to FIGS. 20A-C. For example, one or more controls 4004 can be operated to cause axial movement of one or more interventional devices relative to one or more other interventional devices (e.g., by causing axial movement of corresponding hubs and/or hub adapters). One or more controls 4004 can be operated to cause introduction of fluid into the lumen of an interventional device to prime the interventional device.

In certain embodiments, one or more controls 4004 may be operated to cause the interventional devices to perform a priming procedure, as described for example, with reference to FIGS. 21A-21B. For example, one or more controls 4004 can be operated to cause reciprocal movement (e.g., axial and/or rotational reciprocal movement) of one or more interventional devices relative to one or more other interventional devices (e.g., by causing reciprocal movement of corresponding hubs and/or hub adapters). One or more controls 4004 can be operated to cause introduction of fluid into the lumen of an interventional device to prime the interventional device (e.g., during relative reciprocal movement).

The processor 4002 may receive signals from the one or more controls 4004 and in response, initiate corresponding actions in the components of the systems described herein. For example, the processor 4002 may be configured to generate output signals that cause responsive actions to be performed by the components of the described herein.

While the foregoing describes robotically driven interventional devices and manually driven interventional devices, the devices may be manually driven, robotically driven, or any combination of manually and robotically driven interventional devices, as will be appreciated by those of skill in the art in view of the disclosure herein.

The foregoing represents one specific implementation of a robotic control system. A wide variety of different robotic control system constructions can be made, for supporting and axially advancing and retracting two or three or four or more assemblies to robotically drive interventional devices, as will be appreciated by those of skill in the art in view of the disclosure herein.

While the foregoing describes interventional devices that are driven by a drive table, other suitable robotic drive systems or mechanisms may be used to drive the interventional devices, as will be appreciated by those of skill in the art in view of the disclosure herein.

Various systems and methods are described herein primarily in the context of a neurovascular access or procedure (e.g., neurothrombectomy). However, the catheters, systems (e.g., drive systems), and methods disclosed herein can be readily adapted for any of a wide variety of other diagnostic and therapeutic applications throughout the body, including particularly intravascular procedures such as in the peripheral vasculature (e.g., deep venous thrombosis), central vasculature (pulmonary embolism), and coronary vasculature, as well as procedures in other hollow organs or tubular structures in the body.

What is claimed is:

1. A system for performing a vascular procedure, comprising:
- a robotic drive system; and
- a plurality of hub assemblies operatively coupled to the robotic drive system, the plurality of hub assemblies comprising:
  - a first hub assembly comprising:
    - a first mount;
    - a first hub removably coupled to the first mount; and
    - a procedure catheter coupled to the first hub; and
  - a second hub assembly comprising:
    - a second mount;
    - a second hub removably coupled to the second mount; and
    - a guide catheter coupled to the second hub;
- wherein the robotic drive system is configured to drive the first hub assembly and the second hub assembly to drive the procedure catheter and the guide catheter within a vasculature of a patient while the procedure catheter is positioned within a lumen of the guide catheter;
- wherein the second hub is configured to be uncoupled from the second mount while the guide catheter is positioned within the vasculature of the patient;
- wherein the second hub is configured to be manually manipulated to navigate the guide catheter to a vascular site while the second hub is uncoupled from the second mount; and
- wherein the robotic drive system is configured to withdraw the procedure catheter from the lumen of the guide catheter prior to the second hub being uncoupled from the second mount.

2. The system of claim 1, wherein the robotic drive system further comprises a drive table and a plurality of hub adapters axially movable within the drive table.

3. The system of claim 2, wherein each of the plurality of hub assemblies is positioned to move axially along the drive table and is magnetically coupled to a corresponding one of the plurality of hub adapters.

4. The system of claim 3, wherein the mount of each of the plurality of hub assemblies is configured to magnetically couple to the corresponding one of the plurality of hub adapters.

5. The system of claim 1, wherein at least one of the procedure catheter and the guide catheter is configured to perform the vascular procedure.

6. The system of claim 5, wherein the vascular procedure comprises a neurovascular thrombectomy.

7. The system of claim 1, wherein the plurality of hub assemblies further comprises a third hub assembly, and a fourth hub assembly.

8. The system of claim 7, wherein the third hub assembly comprises a third interventional device and the fourth hub assembly comprises a fourth interventional device, wherein the guide catheter, the procedure catheter, the third interventional device, and the fourth interventional device.

9. The system of claim 7, wherein the plurality of hub assemblies comprise one or more of an access catheter hub assembly having an access catheter and a guidewire hub assembly having a guidewire.

10. The system of claim 7, wherein at least one of the plurality of hub assemblies is configured to receive an additional interventional device therethrough.

11. The system of claim 10, wherein the hub of the at least one of the plurality of hub assemblies is configured to receive the additional interventional device therethrough.

12. A method of performing a vascular procedure, comprising:

coupling a plurality of hub assemblies to a robotic drive system, the plurality of hub assemblies comprising:

a first hub assembly comprising a first mount, a first hub removably coupled to the first mount, and a first interventional device coupled to the first hub; and a second hub assembly comprising a second mount, a second hub removably coupled to the second mount, and a second interventional device coupled to the second hub;

robotically driving the first hub assembly and the second hub assembly to drive the first interventional device and the second interventional device within a vasculature of a patient; and uncoupling the second hub from the second mount while the second is positioned within the vasculature of the patient;

wherein the first interventional device is a procedure catheter and the second interventional device is a guide catheter, wherein the procedure catheter is positioned within a lumen of the guide catheter while driving the first hub assembly and the second hub assembly, wherein the method further comprises withdrawing the procedure catheter from the lumen of the guide catheter prior to uncoupling the second hub from the second mount.

13. The method of claim 12, wherein robotically driving the first hub assembly and the second hub assembly to drive the first interventional device and the second interventional device within the vasculature of the patient comprises driving the first interventional device and the second interventional device to achieve supra-aortic access.

14. The method of claim 12, further comprising manually driving the second hub while the second hub is uncoupled from the second mount to drive the second interventional device to a vascular site.

15. The method of claim 12, further comprising inserting a third interventional device through a lumen of the second interventional device and manually driving the third interventional device into the vasculature of the patient.

16. The method of claim 15, further comprising performing the vascular procedure using the third interventional device.

17. The method of claim 16, wherein the vascular procedure is a neurovascular thrombectomy.

18. The method of claim 16, wherein the third interventional device is a stent retriever or a stent retriever catheter.

19. The method of claim 12, wherein coupling the plurality of hub assemblies to the robotic drive system comprises magnetically coupling the first mount to a first hub adapter through a sterile barrier and magnetically coupling the second mount to a second hub adapter through the sterile barrier.

20. The method of claim 12, further comprising inserting a third interventional device through the lumen of the guide catheter after the second hub is uncoupled from the second mount and manually driving the third interventional device into the vasculature of the patient.

* * * * *